(12) United States Patent
Kosley, Jr. et al.

(10) Patent No.: US 6,479,495 B1
(45) Date of Patent: Nov. 12, 2002

(54) AMINOALKYLPHENOL DERIVATIVES AND RELATED COMPOUNDS

(75) Inventors: Raymond W. Kosley, Jr., Bridgewater, NJ (US); Mark G. Palermo, Oro Valley, AZ (US); Stephen J. Shimshock, Somerville, NJ (US); Veronica Wolf, Sandy, UT (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/459,046

(22) Filed: Dec. 10, 1999

Related U.S. Application Data

(63) Continuation of application No. 09/148,601, filed on Sep. 4, 1998, now abandoned.
(60) Provisional application No. 60/108,158, filed on Sep. 29, 1997.

(51) Int. Cl.$^7$ .................. C07D 295/06; A61K 31/496

(52) U.S. Cl. ................... 514/252.12; 514/252.14; 514/253.01; 514/253.06; 514/253.11; 514/254.05; 514/254.07; 544/330; 544/360; 544/363; 544/370; 544/398

(58) Field of Search ................... 544/398, 330, 544/360, 363, 370; 514/252.12, 252.14, 253.01, 253.06, 253.11, 254.05, 254.07

(56) References Cited

U.S. PATENT DOCUMENTS

| | | | |
|---|---|---|---|
| 2,927,924 A | 3/1960 | Mills | 260/268 |
| 5,051,422 A | 9/1991 | Lumma, Jr. et al. | 514/252 |
| 5,143,910 A | 9/1992 | Onoue et al. | 514/201 |
| 5,681,954 A | 10/1997 | Yamamoto et al. | 544/114 |

FOREIGN PATENT DOCUMENTS

| | | |
|---|---|---|
| EP | 0 500 336 A1 | 8/1992 |
| EP | 624584 | * 11/1994 |

OTHER PUBLICATIONS

W.S. Saari, et all., Journal of Medicinal Chemistry, 26, 1696 (1983), published in the U.S. and entitled "Pyridinylpiperazines, a New Class of Selective $\alpha_2$–Adrenoceptor Antagonists".
Chemical Abstracts, vol. 54, No. 6, Mar. 25, 1960 (Columbus, OH, USA) p. 5678, col. 2, the abstract No. 5679b, Yamazaki, T. "Synthesis in the azabenzoquinolizine group".
Chemical Abstracts, vol. 54, No. 14, Jul. 25, 1960 (Columbus, OH, USA) p. 14280, col. 2, Mills, J. "Phenethyl substituted piperazines".
Chemical Abstracts, vol. 59, No. 11, Nov. 25, 1963 (Columbus, OH, USA) p. 12804, col. 2, Boissier, J.R. et al. "Synthesis and pharmacological study of new piperazine derivatives".
Chemical Abstracts, vol. 62, No. 5, Mar. 1, 1965 (Columbus, OH, USA) p. 5277, col. 1, the abstract No. 5277g, Ratouis, R. et al. "Synthesis and pharmacologial study of new piperazine derivatives".
Chemical Abstracts, vol. 62, No. 12, Jun. 7, 1965 (Columbus, OH, USA) p. 15243, col. 1, the abstract No.15243g, Mull, R.P. et al. "'N,N'–disubstituted compounds with diverse biological activities".
Chemical Abstracts, vol. 62, No. 13, Jun. 21, 1965 (Columbus, OH, USA) p. 16566, col. 2, the abstract No. 15243g, Fuller, R. et al. "Inhibition of rate liver tryptophan hydroxylase in vitro."
Chemical Abstracts, vol. 63, No. 11, Nov. 22, 1965 (Columbus, OH, USA) p. 14880, col. 2, Pyrimidine derivatives. Science Union et Cie.–Societe Francaise de Recherche Medicale activities.
Chemical Abstracts, vol. 97, No. 15, Oct. 11, 1982 (Columbus, OH, USA) p. 728, col. 1, the abstract No. 127638x, Blume, E. et al. "1–(3–pioxolan–2–ylmethyl)azoles, their salts and their use".
Chemical Abstracts, vol. 115, No. 17, Oct. 28, 1991 (Columbus, OH, USA) p. 921, col. 1, the abstract No. 183239v, Katritzky, A.R. et al. "Compounds with potential second order non–linear optical activity".
Chemical Abstracts, vol. 53, No. 9, May 10, 1959 (Columbus, OH, USA) p. 9254, col. 2, Thomae, K. et al. "Tertiary amins".
Chemical Abstracts, vol. 92, No. 19, May 12, 1980 (Columbus, OH, USA) p. 584, col. 1, the abstract No. 16377r, Klause, R. et al. "Neuropsychotropic activity of dopamine analogous 4,7–methano–1H–isoindoles".
Chemical Abstracts, vol. 71, No. 7, Aug. 18, 1969 (Columbus, OH, USA) p. 258, col. 2, the abstract No. 30163p, Mndzhoyan, A.L. et al. "Synthesis of p–alkoxybenzoic acid derivatives".
Chemical Abstracts, vol. 106, No. 7, Feb. 16, 1987 (Columbus, OH, USA) p. 594, col. 1, the abstract No. 49684x, Casagrande, C. et al. "Synthesis and chemical properties of ibopamine and related esters of N–substituted dopamines— synthesis of ibopamine metabolites".
Chemical Abstracts, vol. 77, No. 9, Aug. 28, 1972 (Columbus, OH, USA) p. 468, col. 2, the abstract No. 61607q, Kaiser A. et al. "(3,4–dihydroxyphenethyl)amine derivatives".
Chemical Abstracts, vol. 51, No. 22, Nov. 25, 1957 (Columbus, OH, USA) p. 18343, col. 1, Votava, Z. et al. "Pharmacological research on synthetic uterotonics".

(List continued on next page.)

*Primary Examiner*—Deepak R. Rao
(74) *Attorney, Agent, or Firm*—Joseph Strupczewski

(57) ABSTRACT

Novel aminoalkylphenols, intermediates and processes for the preparation thereof, and methods of relieving memory dysfunction utilizing the aminoalkylphenols or compositions thereof are disclosed.

12 Claims, No Drawings

OTHER PUBLICATIONS

Chemical Abstracts, vol. 56, No. 2, Jan. 22, 1962 (Columbus, OH, USA) p. 1324, col. 2, Kindler, K. et al. "Mechanism of chemical reactions".

Chemical Abstracts, vol. 56, No. 6, Mar. 19, 1962 (Columbus, OH, USA) p. 6012, col. 2, Battersby, A. R. et al. "Synthetic applications of 1,2–dihydroisoquinolines".

Chemical Abstracts, vol. 85, No. 19, Nov. 8, 1976 (Columbus, OH, USA) p. 503, col. 2, the abstract No. 142879x, HEEP, U. et al. "Insect–repellant carbamates".

Chemical Abstracts, vol. 51, No. 20, Oct. 25, 1957 (Columbus, OH, USA) p. 15699, col. 1, Akiya, S. "Synthetic compounds active against Salmonella–dysentery group bacilli".

Chemical Abstracts, vol. 64, No. 4, Feb. 14, 1966 (Columbus, OH, USA) p. 5197, col. 1, Yamada, S. et al. "Solvent effect on the optical rotatory dispersion of N–thiacyl derivatives of amino acids".

Chemical Abstracts, vol. 123, No. 21, Nov. 20, 1995 (Columbus, OH, USA) p. 1174, col. 2, the abstract No. 285700w, Steen, R. et al. "Synthesis of 3–acyl–and 3–carbamoyl flavones".

Chemical Abstracts, vol. 123, No. 3, Jul. 17, 1995 (Columbus, OH, USA) p. 830, col. 2, the abstract No. 32860e, Edgar, V. et al. "New bis(hispidine) derivatives".

* cited by examiner

AMINOALKYLPHENOL DERIVATIVES AND RELATED COMPOUNDS

This application is a continuation of Ser. No. 09/148,601 filed Sep. 4, 1998 now abandoned which claims benefit from Provisional application No. 60/108,158 filed Sep. 29, 1997.

The present invention relates to aminoalkylphenols. More particularly, the present invention relates to aminoalkylphenol derivatives of formula 1

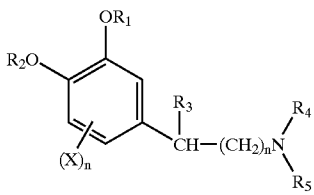

wherein:

$R_1$ is hydrogen, loweralkyl, a group of the formula $CONR_6R_7$, a group of the formula $CH_2COOR_8$, a group of the formula $CH_2CH_2OH$, a group of the formula $CH_2CN$, or a group of the formula $CH_2C≈C—R_9$, a group of the formula

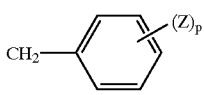

or a group of the formula $Si(R_{11})_3$;

$R_2$ is hydrogen, loweralkyl, a group of the formula $CONR_6R_7$, a group of the formula $SO_2R_{10}$, a group of the formula

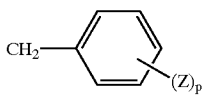

or a group of the formula $Si(R_{11})_3$;

$R_3$ is hydrogen or loweralkyl;
$R_4$ is hydrogen or loweralkyl;
$R_5$ is hydrogen, loweralkyl, a group of the formula

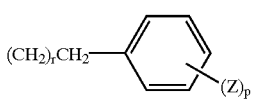

or a group of the formula

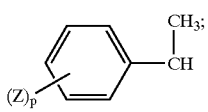

$R_4$ and $R_5$ taken together with the nitrogen atom to which they are attached form a group of the formula

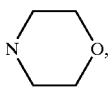

group of the formula

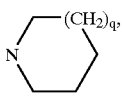

a group of the formula

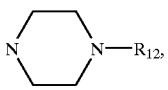

a group of the formula

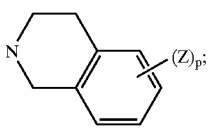

$R_6$ is hydrogen or loweralkyl;
$R_7$ is alkyl of 1 to 10 carbon atoms, or a group of the formula

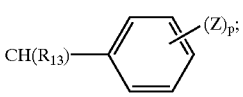

a group of the formula

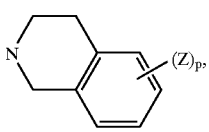

or a group of the formula

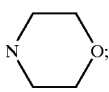

$R_6$ and $R_7$ taken together with the nitrogen atom to which they are attached form a group of the formula

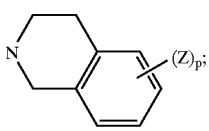

$R_8$ is loweralkyl;
$R_9$ is hydrogen, a group of the formula $C(R_{14}R_{14})OH$, a group of the formula

group of the formula

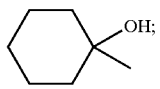

$R_{10}$ is loweralkyl;
$R_{11}$ is loweralkyl;
$R_{12}$ is loweralkyl, hydroxyloweralkyl, a group of the formula $COR_{15}$, a group of the formula

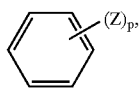

a group of the formula

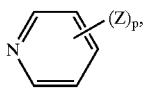

a group of the formula

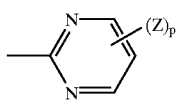

a group of the formula

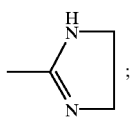

or a group of the formula

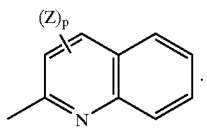

$R_{13}$ is hydrogen or loweralkyl;
$R_{14}$ is hydrogen or loweralkyl;
$R_{14}$ is hydrogen or loweralkyl;
$R_{15}$ is a group of the formula

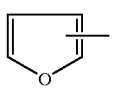

or loweralkyl;
$R_{20}$ is loweralkyl;
X is hydrogen or halogen;

Z is hydrogen, halogen, loweralkyl, hydroxyl, loweralkoxy, trifluoromethyl, nitro or cyano, $R_{20}CO$, or a group of the formula $OCONR_6R_7$;
m is 1 or 2;
n is 0 or 1;
p is 1 or 2;
q is 0, 1 or 2;
r is 0, 1 or 2;
the optical isomers thereof; or the pharmaceutically acceptable salts thereof, which are useful for relieving memory dysfunction and thus indicated in the treatment of Alzheimer's disease, alone, or in combination with adjuvants.

Subgeneric thereto are compounds wherein:
(a) $R_1$ is a group of the formula $CONR_6R_7$;
(b) $R_2$ is loweralkyl;
(c) $R_2$ is a group of the formula $CONR_6R_7$;
(d) $R_1$ is loweralkyl;
(e) $R_4$ and $R_5$ taken together with the nitrogen to which they are attached form a group of the formula

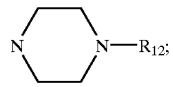

(f) $R_1$ is a group of the formula $CONR_6R_7$ and $R_4$ and $R_5$ together with the nitrogen to which they are attached form a group of the formula

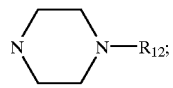

and n is 0; and
(g) $R_2$ is a group of the formula $CONR_6R_7$ and $R_4$ and $R_5$ taken together with the nitrogen to which they are attached form a group of the formula

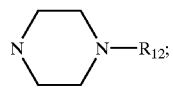

and n is 0.

The present invention also relates to compounds of formula 2

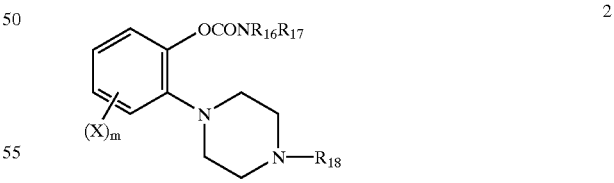

wherein $R_{16}$ and $R_{17}$ are independently hydrogen or alkyl of 1 to 10 carbon atoms and $R_{18}$ is a group of the formula

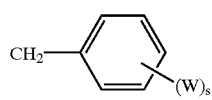

wherein W is hydrogen, loweralkyl, loweralkoxy, hydroxy, halogen or trifluoromethyl, and s is 1 or 2; X is hydrogen or halogen; m is 1 or 2, the optical isomers thereof; or the pharmaceutically acceptable salts thereof; of formula 3

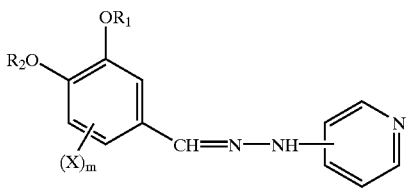

wherein $R_1$ is loweralkyl, benzyl, or a group of the formula $CH_2C\approx CH$; or a group of the formula $CONR_6R_7$ wherein $R_6$ is hydrogen and $R_7$ is loweralkyl; $R_2$ is hydrogen, loweralkyl, a group of the formula $Si(R_{11})$, wherein $R_{11}$ is loweralkyl or $R_2$ is a group of the formula $COR_6R_7$ wherein $R_6$ is hydrogen and $R_7$ is loweralkyl; X is hydrogen or halogen; m is 1 or 2; the optical isomers thereof; or salts thereof; of formula 4

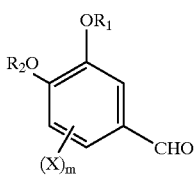

wherein $R_1$ is loweralkyl, a group of the formula $C\approx CH$, a group of the formula $CH_2COOR_8$, a group of the formula

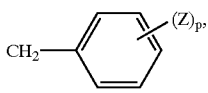

a group of the formula $CONR_6R_7$ or a group of the formula $Si(R_{11})_3$; $R^2$ is a group of the formula $SO_2R_{10}$, a group of the formula

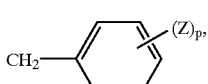

a group of the formula $Si(R_{11})_3$ or a group of the formula $CONR_6R_7$; $R_8$ is loweralkyl; Z is hydrogen, halogen, loweralkyl, hydroxyl, loweralkoxy, trifluoromethyl, nitro or cyano; p is 1 or 2; $R_6$ is hydrogen; $R_7$ is a group of the formula

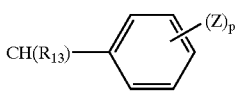

wherein $R_{13}$ is loweralkyl and Z and p are as defined herein; and $R_{11}$ is loweralkyl; X is hydrogen or halogen; m is 1 or 2, or the optical isomers thereof; and formula 5

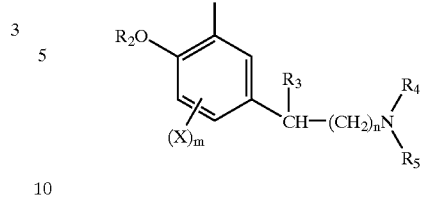

wherein $R_2$ is hydrogen, loweralkyl or a group of the formula $CONR_7R_7$ wherein $R_6$ and $R_7$ are loweralkyl; $R_3$ is hydrogen or loweralkyl; $R_4$ and $R_5$ taken together with the nitrogen atom to which they are attached form a group of the formula

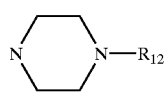

wherein $R_{12}$ is a group of the formula

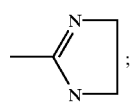

n is 0; X is hydrogen or halogen; m is 1 or 2 or the optical isomers thereof; or pharmaceutically acceptable salts thereof; which are useful as intermediates for the preparation of the aminoalkyl phenols of the present invention and for relieving memory dysfunction.

The invention also includes compounds of formula 43

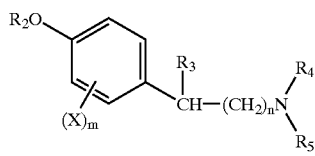

wherein:
  $R_2$ is hydrogen, loweralkyl or a group of the formula $CONR_6R_7$;
  $R_3$ is hydrogen or loweralkyl;
  $R_4$ and $R_5$ taken together with the nitrogen atom to which they are attached form a group of the formula

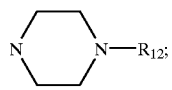

$R_{12}$ is a group of the formula

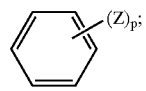

Z is hydrogen, halogen, loweralkyl, hydroxyl, loweralkoxy, trifluoromethyl, nitro, cyano or $COCH_3$;
  m is 1 or 2;
  n is 0 or 1;
  p is 1 or 2;

the optical isomers thereof, or the pharmaceutically acceptable salts thereof.

As used throughout the specification and appended claims, the term "alkyl" refers to a straight or branched chain hydrocarbon radical containing no unsaturation and having 1 to 12 carbon atoms. Examples of alkyl groups are methyl, ethyl, 1-propyl, 2-propyl, 1-butyl, 1-pentyl, 3-hexyl, 4-heptyl, 2-octyl, 3-nonyl, 4-decyl, undecyl, dodecyl, and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like. The term "halogen" refers to a member of the family fluorine, chlorine, bromine, or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "alkoxy" refers to a monovalent substituent which consists of an alkyl group linked through an ether oxygen and having its free valence from the ether oxygen. Examples of alkoxy groups are methoxy, ethoxy, proproxy, 2,2-dimethylethoxy, hexoxy, octoxy, decoxy and the like. The term "lower" as applied to any of the aforementioned groups refers to a group having a carbon skeleton containing up to and including 10 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, those instant compounds characterized by the presence of a carboxyl acid group and an optically active base, or by synthesis from optically active precursors.

The present invention comprehends all optical isomers and racemic forms thereof of the compounds disclosed and claimed herein. The formulas of the compounds shown herein are intended to encompass all possible optical isomers of the compounds so depicted.

The novel aminoalkylphenols of the present invention are prepared by the processes illustrated in the Reaction Schemes. To prepare an aminoalkylphenol 1 wherein $R_3$ is hydrogen or loweralkyl and n is 0, a benzaldehyde 6, or a phenylalkylketone 10, is condensed with an amine 7 in the presence of a reducing agent to provide 8 or 11, respectively. The reductive amination is generally performed in the presence of a mild selective reducing agent such as an alkali metal trialkanoyloxyborohydrideor an alkali metal cyanoborohydride in a suitable solvent. Among alkali metal trialkanoyloxy-borohydrides, there may be mentioned lithium-, sodium- and potassium triacetoxyborohydride. Among alkali metal cyanoborohydrides, there may be mentioned lithium-, sodium- and potassium cyanoborohydride. Among suitable solvents, there may be mentioned halocarbons such as dichloromethane, trichloromethane, 1,2-dichloroethane and 1,1-dichloroethane, or ethereal solvents such as tetrahydrofuran, dioxane and 2-methoxyethyl ether, optionally containing an alkanoic acid such as acetic acid when a trialkanoyloxyborohydride is employed, and an alkanol such as methanol or ethanol in the presence of a mineral acid such as hydrochloride acid or an alkanoic acid such as acetic acid when a cyanoborohydride is employed. Sodium triacetoxyborohydride is the preferred reducing agent; 1,2-dichloroethane is the preferred halocarbon. The reaction of a benzaldehyde 6 and a secondary amine 7 is preferably carried out in the absence of an alkanoic acid such as acetic acid. While the temperature at which the reaction is conducted is not narrowly critical, the reaction is conveniently carried out at ambient temperature.

Alternatively, an aminoalkylphenol 1 wherein $R_3$ is hydrogen and n is 0, is prepared by condensing a benzyl halide 9 with an amine 7 to provide 13. The condensation is accomplished by means of an alkali metal hydride such as sodium hydride in a halocarbon such as chloromethane, dichloromethane, or 1,1- or 1,2-dichloroethane or dimethylformamide, at about ambient temperature, although reduced or elevated temperatures may be employed. The preferred condensation medium is sodium hydride as a dispersion in oil in dichloromethane.

To fabricate an aminoalkylphenol derivative 1 wherein $R_3$ is hydrogen or loweralkyl and n is 1, a haloethylphenol 12 is condensed with an amine 7 to provide 13 by the processes herein described.

To gain access to an aminoalkylphenol derivative 1 wherein $R_3$ is loweralkyl and n is 0, a phenylalkylketone 10 is condensed with an amine 7 to provide 11. The reaction is carried out in the presence of a reducing agent such as titanium (IV) alkoxide in a suitable solvent such as acetonitrile or dichloromethane at about ambient temperature followed by an alkali metal cyanoborohydride in an alkanol, or an alkanoic acid such as acetic acid or a mineral acid such as hydrochloric acid, optimally an alkanoic acid also at ambient temperature. Among titanium (IV) alkoxides there may be mentioned titanium (IV) methoxide, titanium (IV) ethoxide, titanium (IV) 2-propoxide, and titanium (IV) 1-propoxide. Among alkali metal cyanoborohydrides there may be mentioned lithium cyanoborohydride, sodium cyanoborohydride and potassium cyanoborohydride. Among alkanols, there may be mentioned methanol, ethanol, 1-propanol and 2-propanol. The preferred reagents for effecting the reductive condensation are titanium (IV) 2-propoxide, sodium cyanoborohydride, ethanol and dichloromethane.

The aminoalkylphenol derivatives and related compounds thereof of the present invention of formula 1 having the described functionality on the benzene ring and in the side-chain, i.e., compounds of formula 1 wherein $R_1$, $R_2$, $R_3$, $R_4$, $R_5$, X, m and n are as hereinbefore disclosed may be prepared starting from benzaldehydes 6 phenylalkyl ketones 10, benzylhalides 9, or phenylethylhalides 12 having the described functionality intact or from the aminoalkylphenol derivatives 8, 11, or 13 by manipulation of the functionality thereof.

To convert an aromatic hydroxyl group (—OH) to a carbamoyloxy moiety

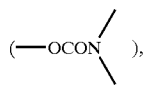

an aminoalkylphenol 1 wherein R1 or $R_2$ is hydrogen is treated-with, for example, a carbamoyl halide 14 of the formula

            14 wherein $R_6$ and $R_7$ are as herein defined and Hal is bromo or chloro in the presence of an acid acceptor such as an alkali metal carbonate, e.g., lithium-, sodium-, potassium- or cesium carbonate in a suitable solvent such as acetonitrile or dichloromethane, or combinations thereof, at about ambient temperature. Cesium carbonate is the preferred acid acceptor.

Alternatively, a tertiary amine such as 1,8-diazabicyclo[5.4.0]undec-7-ene may be used as the acid acceptor and acetonitrile as the solvent in the reaction of a phenol 1 with a carbamoyl halide 14.

The conversion of a hydroxyl group (—OH) to a carbamoyloxy moiety

may also be effected by treating an aminoalkylphenol 1 wherein $R_1$ or $R_2$ is hydrogen with an isocyanate 15

$R_6$ or $R_7$—N=C=O    15

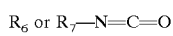

wherein $R_6$ or $R_7$ is as herein defined in the presence of a copper (I) halide, wherein the halide is chloro or bromo, in ethyl acetate, acetonitrile or dichloromethane, or combinations thereof. The introduction of a carbamoyl group

by means of an isocyanate 15 may also be accomplished in an ethereal solvent such as tetrahydrofuran in the presence of an alkali metal carbonate such as potassium carbonate. In addition, the modification of a hydroxyl group (—OH), i.e., the conversion to a carbamoyloxy function

may be effected using an amine 16

HNR$_6$R$_7$    16

wherein $R_6$ and $R_7$ are as defined herein in the presence of 1,1∂-carbonyldiimidazole in tetrahydrofuran.

To prepare aminoalkylphenols of formula 1 wherein $R_1$ is a group of the formula CH$_2$C≉CR$_9$ wherein $R_9$ is as described herein, i.e., to introduce the ethynylalkyl moiety (CH$_2$C≠C—) into the phenoxy system, an ethynylmethoxybenzaldehyde 20, which is fabricated from a benzaldehyde 17 wherein $R_1$ is loweralkyl and X and m are as herein described by sulfonylation of 17 to an alkylsulfonylbenzaldehyde 18 wherein $R_1$ and $R_{15}$ are loweralkyl, dealkylation of 18 to a hydroxybenzaldehyde 19 followed by ethynylalkylation of 19 to ethynylalkoxybenzaldehyde 20, is converted to an aminoalkylbenzene 21 wherein $R_3$, $R_4$, $R_5$ and n are as described herein, which is in turn hydrolyzed to an aminoalkylphenol 22 and carbamoylated to carbamate 23 wherein $R_6$ and $R_7$ are as described herein. The conversion of an ethynylalkoxybenzaldehyde 20 to an aminoalkylbenzene 21 is accomplished by the methods disclosed herein. The hydrolysis of a sulfonyloxybenzene 21 to a phenol 22 is performed in an aqueous alkanol, such as aqueous methanol, containing an alkali metal hydroxide such as sodium hydroxide within a temperature range of about 25° to 75° C., a hydrolysis temperature of about 50° C. being preferred. The carbamoylation of 22 to 23 is effected as herein described. Alternatively, a phenol 22 is converted to carbamate 23 by treatment with an alkali metal carbonate such as potassium carbonate in an ethereal solvent such as tetrahydrofuran followed by an isocyanate of formula 15 at ambient temperature as herein described.

Substituted ethynylmethoxybenzenecarbamates 26 wherein $R_9$ is a group as described herein other than hydrogen are prepared from ethynylmethoxyphenols 22 by protecting the phenolic group thereof, introducing the $R_9$ moiety to yield substituted ethynylmethoxybenzenes 25, removing the protecting group of 25 and elaborating the carbamoyloxybenzene 26 wherein $R_6$ and $R_7$ are as herein described.

The protection of the phenolic group of ethynylmethoxyhydroxybenzene 22 is accomplished by treating the phenol 22 with tri-(2-propyl)silyl chloride of formula 27a ((CH$_3$)$_2$CH)$_3$SiCl    27a in a dipolar aprotic solvent, e.g., dimethylacetamide, dimethylformamide, hexamethylphosphoramide or dimethylsulfoxide, dimethylformamide being preferred, in the presence of an acid acceptor such as a tertiary amine, e.g., di-(2-propyl)ethylamine at ambient temperature.

The substituent ($R_9$), i.e., a group of the formula ($R_{14}R_{14'}$)CHOH wherein $R_{14}$ is as described herein, or a group of the formula

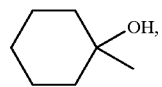

or a group of the formula

is introduced by treating the ethynylmethoxysilyloxybenzene 24 with an alkyllithium such as n-butyllithium in an ethereal solvent such as tetrahydrofuran at a reduced temperature within the range of about –30° to about –50° C. followed by a carbonyl compound of formula 28a ($R_{14}R_{14'}$)C=O    28a wherein $R_{14}$ and $R_{14'}$ are hydrogen or loweralkyl or a compound of the formula

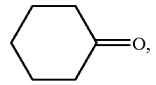

or a compound of the formula

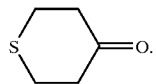

A carbamoyloxy derivative 26 of a substituted ethynylmethoxybenzene 25 is prepared in situ by treatment of 25 with tetra-n-butylammonium fluoride in an ethereal solvent such as tetrahydrofuran at ambient temperature to remove the protecting group followed by an isocyanate of formula 15 in the presence of a lithium halide, preferably lithium chloride.

Similarly, to prepare aminoalkylphenols of formula 1, i.e., compounds of formula 30 wherein Ris as herein described, a hydroxybenzaldehyde 27 is ethynylalkylated to afford ethynylalkoxyaldehyde 28 which is reductively animated to in am inoalkylethynylalkoxybenzene 30 and then alkylated to an ethynylalkoxy carbinol 30. The sequence of reactions is performed by processes herein-described.

To synthesize aminoalkylphenol derivatives of formula 1 wherein $R_1$ is a group of the formula —$OCH_2CH_2OH$, i.e., hydroxyethoxyaminoalkylbenzenes,a hydroxybenzaldehyde 27 is converted to an ester 31 which is reductively aminated to an aminoalkylbenzene 32 and then reduced to hydroxyalkoxybenzene 33. The conversion of phenol 27 to ester 31 is carried out by treating 27 with an alkyl haloacetate of formula 34

$HalCH_2CO_2R_8$   34 wherein $R_8$ is as herein defined and Hal is bromo or chloro in the presence of an acid acceptor such as an alkali metal carbonate in a suitable solvent such as acetone at an elevated temperature of about the reflux temperature of the reaction mixture. The transformation of benzaldehyde 31 to aminoalkylbenzene 32 is accomplished by methods herein described. The reduction of ester 32 is effected by treating the alkoxycarbonylalkoxybenzene32 with an alkali metal aluminum hydride such as lithium aluminum hydride in an ethereal solvent such as tetrahydrofuran at a reaction temperature of about ambient temperature.

To prepare a hydroxyethoxyaminophenol 33 wherein $R_2$ is hydrogen for subsequent conversion to a carbamate 1 wherein $R_2$ is carbamoyl, a hydroxyaldehyde 27 wherein $R_2$ is benzyl is converted to a hydroxyethoxyaminoalkylbenzyloxybenzene 33 wherein $R_2$ is benzyl by the processes described herein for the alkoxyl compounds. The benzyl group of 33 is removed by means of hydrogen at atmospheric pressure in the presence of a metal catalyst such as palladium, preferably palladium on a support, such as carbon, in an alkanoic acid such as acetic acid at ambient temperature. The introduction of the carbamoyl group may be accomplished by the processes herein described.

Removal of functional groups bound to the potential phenolic oxygen atoms of the aminoalkylbenzenes of the present invention, i.e., the formation of aminoalkylphenols of formulas 36 and 37 is effected by hydrolysis, debenzylation and/or demethylation processes. For example, to remove an aminocarbonyl group of a compound of formula 35 wherein $R_1$ is a group of the formula $CONR_6R_7$ wherein $R_6$ and $R_7$ are as hereinbefore described and $R_2$ is hydrogen, loweralkyl or benzyl, a carbamate 35 is treated with an alkali metal hydroxide in an alkanol at ambient temperature. Among alkali metal hydroxides there may be mentioned lithium, sodium or potassium hydroxide. Among alkanols there maybe mentioned methanol, ethanol or 1-propanol. Sodium hydroxide in methanol is the preferred alkali metal hydroxide; methanol is the preferred alkanol.

Similarly, removal of an alkanoyl group from an aminoalkylbenzene 35 wherein $R_2$ is a group of the formula RCO wherein R is loweralkyl and $R_1$ is hydrogen, loweralkyl or benzyl, is also effected by hydrolysis. In this case, the hydrolysis is achieved by treating the ester 35 with alkali metal hydroxide such as sodium hydroxide and an alkanol such as aqueous ethanol at a slightly elevated temperature of about 50° C., although a hydrolysis temperature within the range of about ambient temperature to about the reflux temperature of the reaction medium is suitable.

To remove a benzyl group from a compound of formula 35, i.e., to debenzylate an aminoalkylbenzene 35 wherein $R_2$ is benzyl and $R_1$ is loweralkyl, an aminoalkylbenzene 35 is treated with ferric chloride in a halocarbon such as dichloromethane at the reflux temperature of the reaction mediums or with hydrogen in the presence of a metal catalyst such as palladium in a solvent such as acetic acid or methanol.

To remove an alkoxy group from a compound of formula 35, i.e., to dealkylate an aminoalkylbenzene 35 wherein $R_2$ is loweralkyl, an aminoalkylbenzene 35 is treated with a hydrohalic acid such as hydrobromic acid at an elevated temperature of about 100°.

To prepare an aminoalkylpenol 40 chacterized by the presence of a heterocyclic moiety, i.e., an aminoalkyphenol 40 wherein $R_1$, $R_2$, $R_3$, X, and m are as hereindescribed, a benzlamine 38 is condensed with 2-methylthio-2-imidazoline 39 in a halocarbon such as trichloromethane at about the reflux temperature of the reaction medium.

To prepare the hydrazones 42 a benzaldehyde 6 is condensed with a hydrazine 41. The condensation is carried out in a halocarbon such as dichloromethane, preferably in the Compound of the invention of formula 43

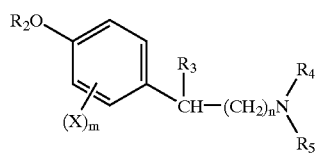

43 wherein the 3-position of the benzene ring is unsubstituted are prepared by processes substanitally similar to those described of the preparation of 3-substituted phenyl compounds of the invention.

To fabricatie and aminoalkybenxene 46 wherein $R_2$, $R_4$ and $R_5$ are as hereinbeforescribed and Y is halo or alkoyl, a phenyl acetic acid 44 is converted to an amide 45 which is reduced to an amine 46 methods described herein.

To prepare aminolkycarbamates 48 and 50 an aminoalkylphenol 47 is converted to cabamate 48 which is transformed to aminoalky 49 and then to carbamate 50 by methods hereindescribed.

REACTION SCHEME A

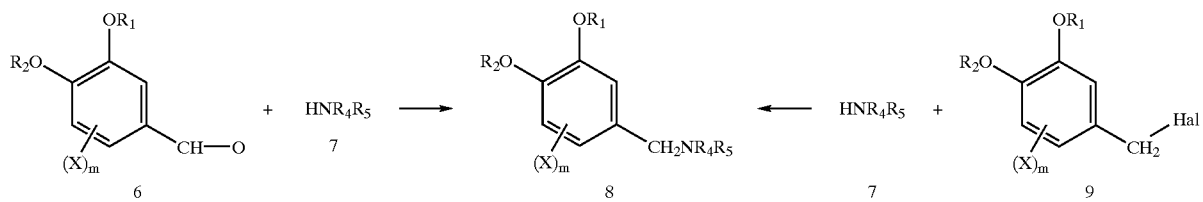

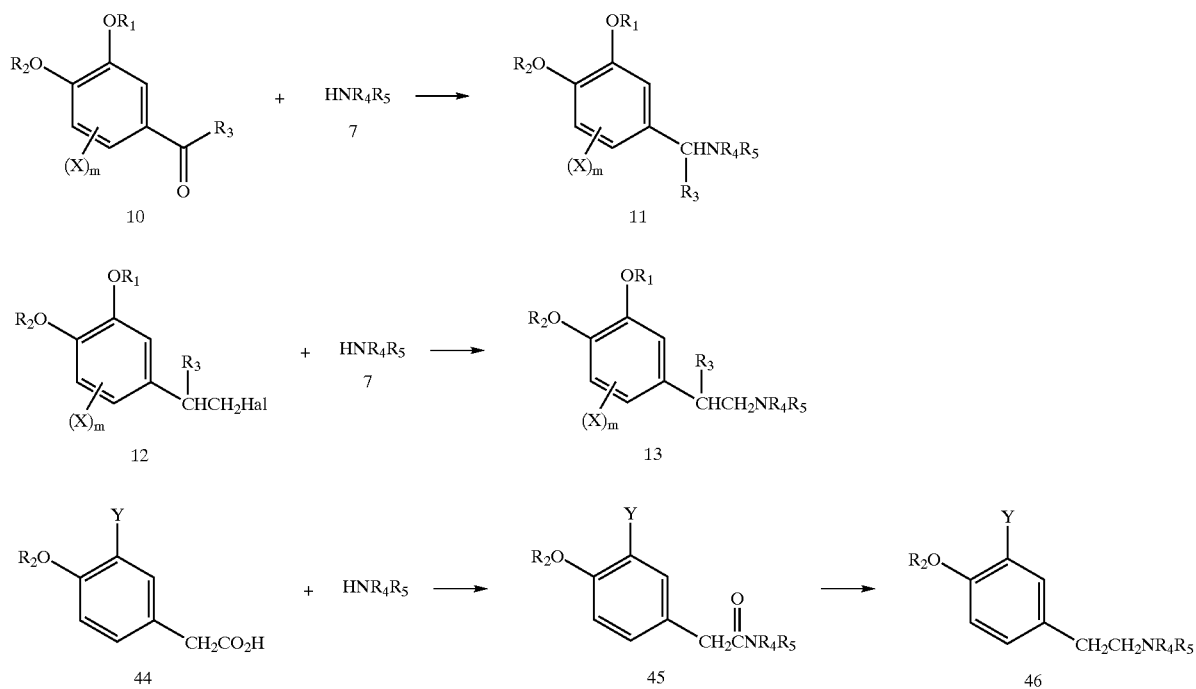
wherein $R_1$, $R_2$, $R_3$, $R_4$, $R_5$, X, Y, and m are as hereinbefore described and Hal is bromo or chloro.
REACTION SCHEME B
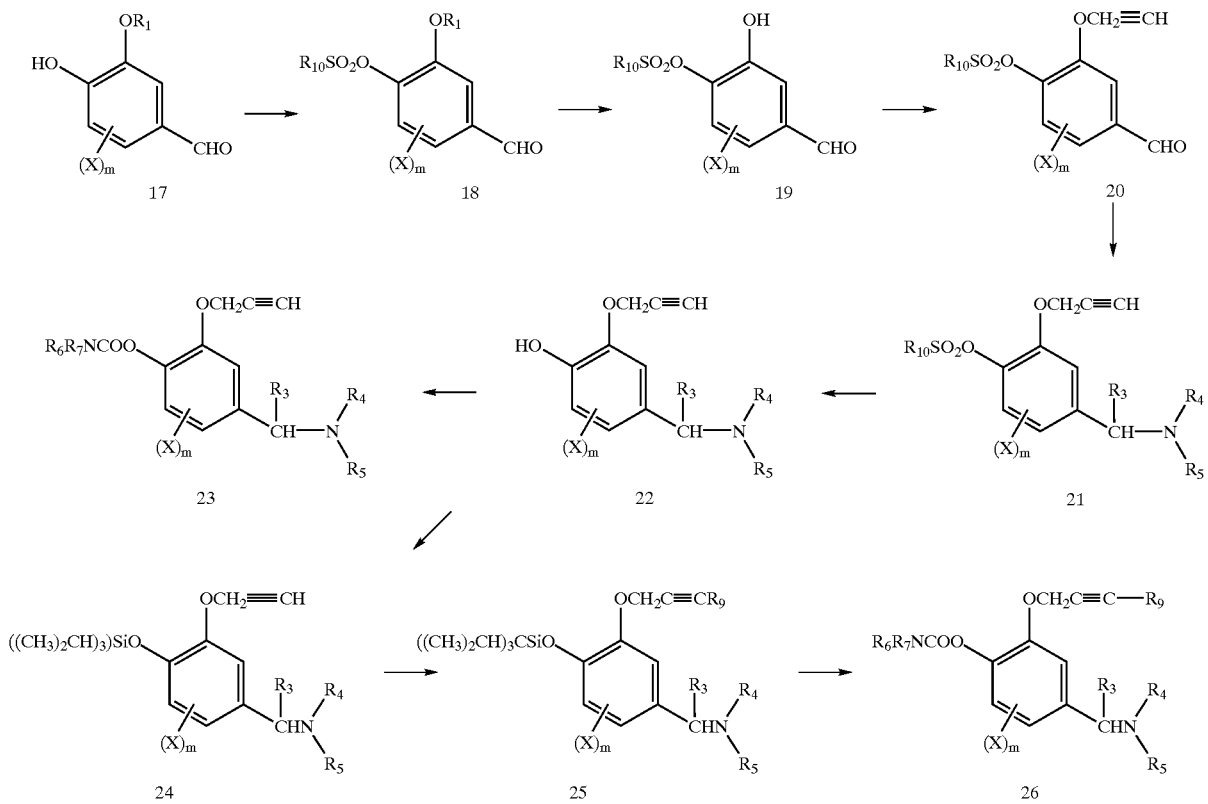

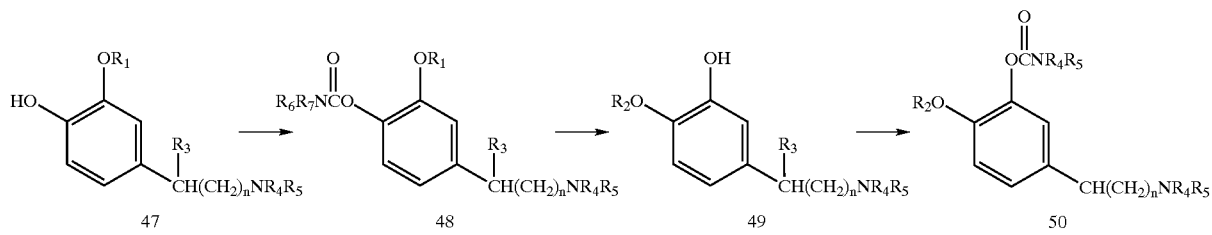
wherein $R_1$, $R_2$, $R_3$, $R_4$, $R_5$, $R_9$, $R_{10}$ and n are as hereinbefore described.
REACTION SCHEME C
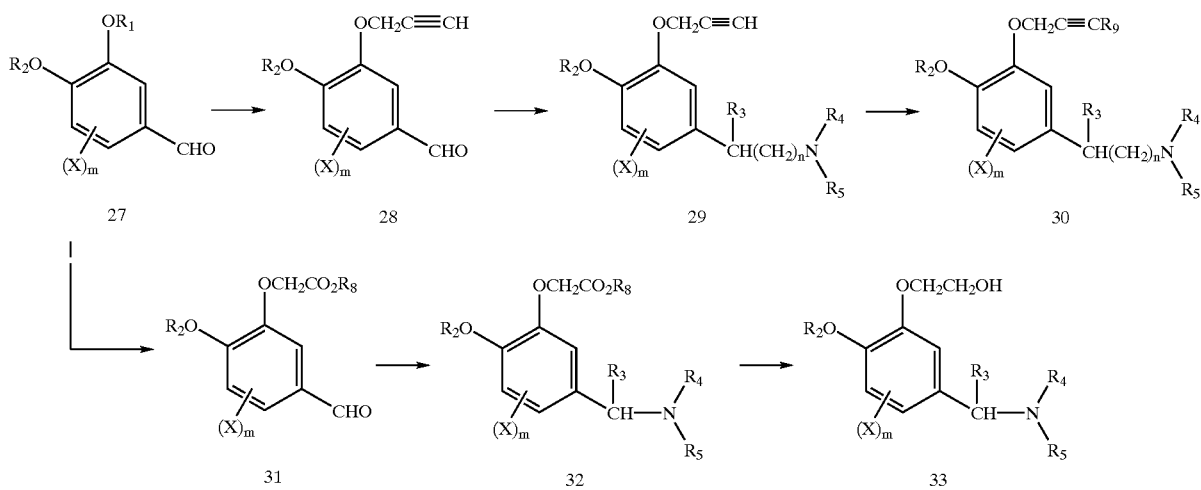
wherein $R_2$ is hydrogen, loweralkyl or benzyl, $R_8$ is loweralkyl, and $R_3$, $R_4$, $R_5$, X, m and n are as hereinbefore described.
REACTIONS CHEM ED
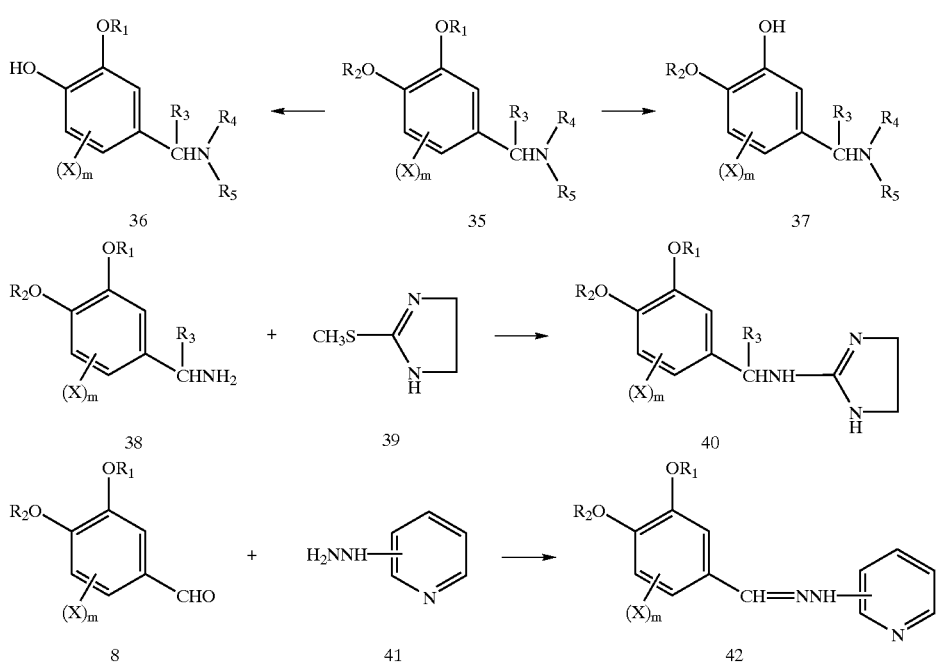
wherein $R_1$, $R_2$, $R_3$, $R_4$, $R_5$, X, m and n are herein described The aminoalkylphenol derivatives and related compounds of the present invention are useful as agents for the relief of memory dysfunction, particularly dysfunctions associated with decreased cholinergic activity such as those found in Alzheimer's disease. Relief of memory dysfunction activity is demonstrated in the in vitro inhibition of acetylcholinesterase assay, an assay for the determination of the ability of a drug to inhibit the inactivation of acetylcholine, a neurotransmitter implicated in the etiology of memory dysfunction and Alzheimer's dementia. In this assay, a modification of a test described G. L. Eliman, et al., Biochemical Pharmacology, 7, 88 (1961), the following reagents are prepared and employed:

1. 0.05M Phosphate Buffer (pH 7.2)

A solution of monobasic sodium phosphate monohydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate in Buffer

The 0.05M Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic acid in Buffer

The 0.05M Phosphate Buffer (pH 7.2) was added to 5.5-dithiobisnitrobenzoic acid to a total volume of 100 ml, i.e., a quantity sufficient (gs) to 100 ml.

4. Stock Solution of Drug

A 2 millimolar stock solution of the test drug is prepared in a quantity sufficient of either acetic acid or dimethyl sulfoxide to volume with 5,5-dithiobisnitrobenzoic acid in Buffer. Stock Solution of Drug is serially diluted (1:10) so that the final cuvette concentration is $10^{-4}$ molar.

Male Wistar rats are decapitated, brains rapidly removed, corpora striata dissected free, weighted and homogenized in 19 volumes (approximately 7 mg protein/ml) of 0.05M Phosphate Buffer (pH 7.2) using a Potter-Elvejhem homogenizer. A 25 µl aliquot of this suspension is added to 1 ml of the vehicle or various concentrations of the test drug and preincubated for 10 minutes at 37° C. Enzyme activity is measured with a Beckman DU-50 spectrophotometer with the following software and instrument settings:

1. Kinetics Soft-Pac™ Module #598273;
2. Program #6 Kindata;
3. Source—Vis;
4. Wavelength—412 nm;
5. Sipper—none;
6. Cuvettes—2 ml cuvettes using auto 6-sampler;
7. Blank—1 for each substrate concentration;
8. Interval time—15 seconds (15 or 30 seconds for kinetics);
9. Total time—5 minutes (5 to 10 minutes for kinetics);
10. Plot—yes;
11. Span—autoscale;
12. Slope—increasing;
13. Results—yes (gives slope); and
14. Factor-1.

Reagents are added to the blank and sample cuvettes as follows:

| 1. | Blank: | 0.8 ml 5.5-Dithiobisnitrobenzoic Acid |
|    |        | 0.8 ml Substrate in Buffer |
| 2. | Control: | 0.8 ml 5.5-Dithiobisnitrobenzoic Acid/Enzyme |
|    |        | 0.8 ml Substrate in Buffer |
| 3. | Drug: | 0.8 ml 5.5-Dithiobisnitrobenzoic Acid/Drug/Enzyme |
|    |        | 0.8 ml Substrate in Buffer |

Blank values are determined for each run to control for non-enzymatic hydrolysis of substrate and these values are automatically subtracted by the Kindata program available on kinetics soft-pac module. This program also calculates the rate of absorbance change for each cuvette.

For $IC_{50}$ Determinations

Substrate concentration is 10 millimolar diluted 1:2 in assay yielding final concentration of 5 millimolar. 5,5-dithiobisnitrobenzoicacid concentration is 0.5 millimolar yielding 0.25 millimolar final concentration.

$$\% \text{ Inhibition} = \frac{\text{Slope Control} - \text{Slope drug} \times 100}{\text{Slope Control}}$$

$IC_{50}$ values are calculated from log-probit analysis

TABLE I

| Compound | Inhibition of Acetyl-cholinesterase Activity $IC_{50}(\mu M)$ |
|---|---|
| 4-(methylaminocarbonyloxy)-3-(propargyloxy) pyrrolidinomethylbenzene | 0.0036 |
| 4-methoxy-3-(propargyloxy)-1-[[4-(pyridin-2-yl) piperazin-1-yl]methyl]benzene | 26.9 |
| 4-[[3-methoxy-4-(methylaminocarbonyloxy) phenylmethyl]-1-pyridin-2-yl)piperazine | 0.536 |
| 4-[[4-methoxy-3-(methylaminocarbonyloxy)] phenylmethyl-1-pyridin-2-yl)piperazine | 2.39 |
| 1-[[3-(methoxy)-4-(methylaminocarbonyloxy) phenyl]methyl]-4-(2-methylphenyl)piperazine | 0.148 |
| 1-[1-(4-N,N-dimethylcarbamoyloxy-3-methoxyphenyl) ethyl]-4-pyridin-2-yl-piperazine | 0.358 |
| N-(2-bromo-4-[dimethylcarbamoyloxy]-5-methoxy)- N'-(pyridin-2-yl)-piperazine | 0.018 |
| Dimethylcarbamic acid-2-methoxy-4--[2-(4-pyridin-2-yl-piperazin-1-yl)ethyl]phenyl ester | 0.515 |
| 1-[[3-(methoxy)-4-(methylaminocarbonyloxy)phenyl] methyl]-4-(2-fluorophenyl)piperazine | 5.06 |
| 1-[1-(4-N,N-dimethylcarbamoyloxy-3-fluorophenyl) ethyl]-4-pyridin-2-yl-piperazine | 14.0 |
| tacrine (reference) | 0.31 |

Relief of memory dysfunction is achieved when the present alkylaminophenol derivatives and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The alkylaminophenol derivatives and related compounds of the present invention are also useful as agents for treating depression. Depression treatment is demonstrated in the in vitro clonidine binding: $\alpha_2$-receptor assay, an assay for the determination of the ability of a drug to bind the clonidine:

$\alpha_2$-receptor, performed by a modification of assays described by D. C. U'Prichard,et al., Molecular Pharmacology,16, 47(1979) and D. C. U'Prichard,et al., Molecular Pharmacology, 13, 454 (1976).

The following reagents are prepared:
1. Tris buffer, pH 7.7
   a. 57.2 g Tris hydrochloride
      16.2 g Tris Base—q.s. to 1 liter (0.5 M Tris buffer, pH 7.7)
   b. Make a 1:10 dilution in distilled $H_2O$ (0.05 M Tris buffer, pH 7.7)
2. Tris buffer containing physiological ions

| a. | Stock Buffer | |
|---|---|---|
| | Sodium chloride | 7.014 g |
| | Potassium chloride | 0.372 g |
| | Calcium chloride buffer | 0.222 g - q.s. to 100 ml in 0.5 Tris |
| | Magnesium chloride | 0.204 g | b. Dilute 1:10 in distilled $H_2O$. This yields 0.05 M Tris hydrochloride pH 7.7; containing sodium chloride (120 mM), potassium chloride (5 mM), calcium chloride (2 mM) and magnesium chloride (1 mM).
3. [4-$^3$H]-Clonidine Hydrochloride (20–30 Ci/mmol) is obtained from New England Nuclear. For $IC_{50}$ determinations: $^3$H-Clonidine is made up to a concentration of 120 nM and 50 μl added to each tube (yields a final concentration of 3 nM in the 2 ml volume assay).
4. Clonidine hydrochloride is obtained from Boehringer Ingelheim. A stock solution of 0.1 mM clonidine is made up to determine nonspecific binding. This yields a final concentration of 1 μM in the assay (20 μl to 2 ml).
5. Test compounds. For most assays, a 1 mM stock solution is made up in a suitable solvent and serially diluted, such that the final concentration in the assay ranges from $10^{-5}$ to $10^{-8}$M. Seven concentrations are used for each assay and higher or lower concentrations may be used, depending on the potency of the drug.

B. Tissue Preparation

Male Wistar rats are sacrificed by decapitation and the cortica tissue rapidly dissected. The tissue is homogenized in 50 volumes of 0.05 M Tris buffer, pH 7.7 (buffer 1b) with the Brinkman Polytron, then centrifuged at 40,000 g for 1 minutes. The supernatant is discarded and the pellet rehomogenized in the original volume of 0.05 M Tris buffer, pH 7.7 and recentrifuged as before. The supemate is discarded and the final pellet rehomogenized in 50 volumes of Buffer 2b. This tissue suspension is then stored on ice. The final tissue concentration is 10 mg/ml. Specific binding is 1% of the total added ligand and 80% of total bound ligand.

C. Assay 100 μl 0.5 M Tris-physiological salts, pH 7.7 (buffer 2a)

| 830 μl | Water |
|---|---|
| 20 μl | Vehicle (for total binding) or 0.1 mM clonidine (for nonspecific binding) or appropriate drug concentration |
| 50 μl | $^3$H-clonidine stock |
| 1000 μl | Tissue suspension |

Tissue homogenates are incubated for 20 minutes at 25° C. with 3 nM $^3$H-clonidine and varying drug concentrations, then immediately filtered under reduced pressure on Whatman GF/B filters. The filters are washed with three five ml volumes of ice-cold 0.05 M Tris buffer, pH 7.7, then transferred to scintillation vials. Ten ml of liquescent counting solution is added to each sample which is then counted by liquid scintillation spectroscopy. Specific clonidine is defined as the difference between total bound and that performed using log-probit analysis. The percent inhibition at each drug concentration is the mean of triplicate determinations.

TABLE II

| Compound | Inhibition of clonidine binding activity $IC_{50}$ (μM) |
|---|---|
| 4-methoxy-3-(propargyloxy)-1-[[4-(pyridin-2-yl)piperazin-1-yl]methyl]benzene | 0.0346 |
| 4-[[3-methoxy-4-(methylaminocarbonyloxy)phenylmethyl]-1-(pyridin-2-yl)piperazine | 4.47 |
| 6,7-dimethoxy-N-[(4-methoxy)-3-(propargyloxy)phenylmethyl)-1,2,3,4-tetrahydroisoquinoline | 0.369 |
| 4-[[4-methoxy-3-(methylaminocarbonyloxy)]phenylmethyl]-1-(pyridin-2-yl)piperazine | 0.800 |
| 4-[[[4-dimethylaminocarbonyloxy)-3-(methoxy)phenyl]methyl]-1-(pyridin-2-yl)-piperazine | 9.11 |
| 2-[3-methoxy-4-(methylaminocarbonyloxy)phenylmethyl]-1-(6,7-dimethoxy)-1,2,3,4-tetrahydroisoquinoline | 3.37 |
| 4-[3-(methoxy)-4-[(1,2,3,4-tetrahydroisoquinolin-2-yl)carbonyloxy]phenylmethyl]-1-pyridin-2-yl)piperazine | 8.02 |
| 1-[[4-(dimethylaminocarbonyloxy)-3-(methoxy)phenyl]methyl]-4-(2-methoxyphenyl)piperazine | 1.54 |
| 1-[[3-(methoxy)-4-(methylaminocarbonyloxy)phenyl]methyl]-4-(2-methylphenyl)piperazine | 0.98 |
| 1-[1-(4-N,N-dimethylcarbamoyloxy-3-methoxyphenyl)ethyl]-4-pyridin-2-yl-piperazine | 5.19 |
| 1-[[3-(methoxy)-4-(methylaminocarbonyloxy)phenyl]methyl]-4-(2-fluorophenyl)piperazine | 2.71 |
| amitriptyline (reference) | 0.039 |

Depression treatment is achieved when the present aminoalkylphenol derivatives and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Acetylcholinesterase inhibitors and clonidine binding inhibitors are known in the art as being useful as relievers of memory dysfunction and as antidepressants, respectively. (See V. Kumar in Alzheimer's Disease: Therapeutic Strategies, E. Giacobini and R. Becker Eds.; Birkhauser, Boston 1994 for memory dysfunction utility and K. F. Tipton in Biochemical and Pharmacological Aspects of Depression, K. F. Tipton and U. B. H. Youdin, Eds., Taylor and Francis, London 1989, for antidepressant utility.

Depression frequently attends memory dysfunction associated with Alzheimer's disease and responds to antidepressant intervention. Thus, the antidepressant component of the pharmacological properties of the compounds of the present invention provide both desirable effects in one chemical entity, providing both therapies in one administration, where indicated. See, for example, W. W. Pendlebury and P. R.

Solomon, Neurobiology of Aging, 15, 287 (1994) at page 287, among others.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fimaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may, also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl, salicylate, or orange flavoring may be added. When the dosage unit is a capsule it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agepts such as benzyl alcohol or thyl parabens; antioxidants such as ascorbic acid or sodium bisulfite; chelating agents such as ethylenediaminetetraaceticacid; buffers such as acetates, citrates or phosphates and agents for the adjustment of tonicity such as sodium chloride or dextrose. The parenteral preparations can be enclosed in ampules, disposable syringes or multiple vials made of glass or plastic.

The following examples are for illustrative purposes only and are not to be construed as limiting the invention in any way whatsoever.

EXAMPLE 1

4-Methoxy-3-propargyloxydimethylaminomethylbenzene Hydrochloride

To a solution of 4-methoxy-3-propargyloxybenzaldehyde (2.05 g) in dry dichloroethane (20 ml) was added a solution of dimethylamine (1.26 g) in 20 ml of dry dichloroethane, with stirring, followed by triacetoxyborohydride (3.44 g). After 0.5 hr, the reaction was poured into cold 10% sodium hydroxide (30 ml) and extracted with chloroform (50 ml). The organic extract was washed with water (50 ml), dried over sodium sulfate, filtered, and the filtrate was concentrated. The residue was dissolved in a minimum volume of chloroform and purified by flash chromatography (silica gel and 5% methanol:chloroform) and eluted with the same solvent system, followed by 10% and 20% methanol:chloroform,respectively. The appropriate fractions were collected and concentrated to give 2.20 g (93%) of product free base. The hydrochloride, prepared by dissolving the free base in chloroform and diethyl ether, adding ethereal hydrogen chloride and collecting the precipitate, had mp 176–180° C.

Analysis: Calculated for $C_{13}H_{18}ClNO_2$: 61.05%; C, 7.09%; H, 5.48%; N, Found: 60.97%; C, 7.02%; H, 5.38%; N.

EXAMPLE 2

4-[3-(2-Methoxy-5-(dimethylamino-1-ylmethyl)phenoxy)propyne-1-yl]tetrahydrothiopyran-4-ol Hydrochloride To a solution of 4-methoxy-3-propargyloxydimethylaminomethylbenzene (14.2 g), azeotropically dried with toluene, in dry tetrahydrofuran (85 ml) was added dropwise a solution of 2.5 M n-butyllithium (25.2 ml) in hexanes at 0° C., with stirring, at a rate such that the internal temperature remained below 5° C. The reaction mixture was stirred for 10 mins at 5 to –5° C. and cooled to –30 to –35° C. To the reaction mixture was added dropwise over 0.5 hr a solution of tetrahydrothiopyran-4-one (7.13 g) in tetrahydrofuran (85 ml) at a rate such that the internal temperature remained below –30° C. The reaction mixture was poured into ice/water (600 ml) and extracted with chloroform (600 ml). The combined organic extracts were washed with water, dried over anhydrous sodium sulfate, filtered, and the filtrate was concentrated. The residue was dissolved in chloroform and purified using high performance liquid chromatography, eluting with 2%, 3%, 5% and 10% of methanol:chloroform, sequentially. The appropriate fractions were collected and concentrated. Toluene was added to the residue, and the solution was concentrated to give 15.0 g (69%) of product free base. A 1 g portion was dissolved in chloroform and diethyl ether and ethereal hydrogen chloride was added to give product, mp 208–210° C.

Analysis: Calculated for $C_{18}H_{26}ClNO_3S$: 58.13%; C, 7.05%; H, 3.77%; N, Found: 57.94%; C, 7.12%; H, 3,67%; N.

EXAMPLE 3

4-Methoxy-3-[(propargyloxy)morpholino-4-yl-methyl]benzene Hydrochloride

To a solution of 4-methoxy-3-propargyloxybenzaldehyde (20 g) in 1,2-dichloroethane (400 ml) was added morpholine-(9.17 g), with stirring, followed by sodium triacetoxyborohydride (29.2 g). The reaction mixture was stirred at ambient temperature for 1 hr, poured onto ice/10% sodium hydroxide solution and extracted with chloroform. The extracts were washed with water, dried over anhydrous sodium sulfate, filtered, and the filtrate was concentrated. The residue was dissolved in chloroform and was flash chromatographed (silica gel), eluting with chloroform followed by 5% methanol/chloroform. The appropriate fractions were collected and concentrated to give 27.5 g (100%) of product free base. A portion (3.00 g) of the free base was dissolved in ether and ethereal hydrogen chloride was added.

The precipitate was collected to give product, mp 176–178° C.

Analysis: Calculated for $C_{15}H_{20}ClNO_3$: 60.50%; C, 6.77%; H, 4.70%; N, Found: 60.43%; C, 6.79%; H, 4.58%; N.

EXAMPLE 4

4-(Methoxy)-3-(propargyloxy)-1-pyrrolidinomethylbenzene Hydrochloride

To a solution of 4-methoxy-3-propargyloxybenzaldehyde (20 g) in 1,2-dichloroethane (400 ml) was added pyrrolidine (7.47 g), with stirring, followed by sodium triacetoxyborohydchde (29.2 g). The reaction mixture was stirred at ambient temperature for 1 hr, poured into ice/10% sodium hydroxide solution and extracted with chloroform. The extracts were washed with water, dried over anhydrous sodium sulfate, filtered, and the filtrate was concentrated. The residue flash chromatographed (silica gel), eluting with chloroform, 1%, 2% and 5% methanol/chloroform. The appropriate fractions were collected and concentrated to give 21 g (85.6%) of product free base. A 3 g portion of the free base was dissolved in ether and ethereal hydrogen chloride was added. The precipitate was collected to give product, mp 163–166° C.

Analysis: Calculated for $C_{15}H_{20}ClNO_2$: 63.94%; C, 7.15%; H, 4.97%; N, Found: 63.72%; C, 7.00%; H, 4.84%; N.

EXAMPLE 5

4-[3-(2-Methoxy-5-(morpholinylmethyl) phenoxylprop-1-yny]tetrahydrothiopyran-4-ol Hydrochloride To a solution of 4-methoxy-3-(propargyloxy)-1-(morpholino-4-yl-methyl)benzene(3.88 g) in dry tetrahydrofuiran (20 ml) in an ice/salt bath was added dropwise 2.5 M n-butyllithium (5.79 ml), with stirring. The solution was stirred for 25 mins, cooled to −40 to −50° C., and a solution of tetrahydrothiopyran-4-one (1.66 g) was added dropwise at −45 to −35° C. over 45 min. The reaction mixture was poured into ice/water, extracted with chloroform and the extracts were washed with water, dried over anhydrous sodium sulfate, filtered, and the filtrate was concentrated. The residue was dissolved in chloroform and chromatographed using high performance liquid chromatography (silica gel), eluting with chloroform, 1%, 2%, 3% and 4% methanol/chloroform, respectively. The appropriate fractions were collected and concentrated to give 3.51 g (65.6%) of product free base. The free base was dissolved in ether and ethereal hydrogen chloride was added. The precipitate was collected to give product, mp 187–189° C.

Analysis: Calculated for $C_{20}H_{28}ClNO_4S$: 58.03%; C, 6.82%; H, 3.38%; N, Found: 57.93%; C, 7.02%; H, 3.26%; N.

EXAMPLE 6

4-Methoxy-3-propargyloxy-1-[(piperdin-1-yl) methyl]benzene Hydrobromide

To a solution of 4-methoxy-3-propargyloxybenzaldehyde (12 g) in 1,2-dichloroethane(125 ml) was added piperidine (6.25 ml), followed by 1,2-dichloroethane (125 ml) and sodium triacetoxyborohydride (20 g). The reaction mixture was stirred at ambient temperature for 1 hr and then poured into 10% sodium hydroxide solution/ice (200 ml). The layers were separated and the aqueous phase was extracted with chloroform (400 ml). The organic extracts were washed with water, dried over anhydrous sodium sulfate, filtered, and the filtrate was concentrated. The residue was flash chromatographed (silica gel), eluting with chloroform and 3% and 5% methanol:chloroform. The appropriate fractions were collected and concentrated to give 13.1 g (80%) of product, free base. A portion (3.59 g) of the residue was dissolved in chloroform and flash chromatographed (silica gel), eluting with chloroform and 3% and 4% methanol:chloroform. The appropriate fractions were collected and concentrated to give 2.67 g of additional free base. The free base was dissolved in diethyl ether, filtered, and ethereal hydrogen bromide was added. The precipitate .was collected to provide product, mp 135–137° C.

Analysis: Calculated for $C_{16}H_{22}BrNO2$: 56.48%; C, 6.52%; H, 4.12%; N, Found: 56.05%; C, 6.71%; H, 3.93%; N.

EXAMPLE 7

3-[[(2-(Hydroxy)-2-methylpent-3-yn-5-yl]oxy]-4-(methoxy)-1-pyrrolidinomethylbenzene Hydrochloride To a solution of 4-(methoxy)-3-(propargyloxy)-1-pyrrolidinomethylbenzene(18.2 g) in dry tetrahydrofuran (50 ml) in an ice/salt bath was added butyllithium (19.7 ml) in hexanes. The solution was stirred at ice bath temperature for about 20 min and cooled to −40 to −45° C. To the solution was added dropwise a solution of acetone (3.16 ml) (dried over a molecular sieve) in dry tetrahydrofuiran (5 ml). The reaction mixture was stirred at −50 to −35° for 35 min, poured into ice/water and the layers were separated. The organic extracts were dried over anhydrous sodium sulfate, filtered, and the filtrate was concentrated. The residue was high performance liquid chromatographed (silica gel), eluting with chloroform, 1%, 2%, and 5% methanol/chloroform. The appropriate fractions were collected and concentrated to give 11.9 g (86%) of product, as the free base. A 2 g sample of the free base was dissolved in ether and ethereal hydrogen chloride was added. The precipitate was collected to provide product, mp 102–104° C.

Analysis: Calculated for $C_{18}H_{26}ClNO_3$: 63.61%; C, 7.71%; H, 4.12%; N, Found: 63.46%; C, 7.55%; H, 3.85%; N.

EXAMPLE 8

4-[3-[2-Methoxy-5-[(piperidin-1-yl)methyl] phenoxylpropyne-1-yl]tetrahydrothiopyran-4-ol Hydrochloride To a solution of 4-methoxy-3-propargyloxy-1-[(piperidin-1-yl)methyl]benzene (2.83 g) in dry tetrahydrofuran (14 ml) at 0° to 5° C. was added dropwise 2.2 M n-butyllithium (5.0 ml) over 20 mins, with stirring. The temperature was lowered to −35 to −30° C., and was stirred at this temperature for 20 mins. To the solution was added dropwise tetrahydrothiopyran-4-one (1.22 g) in dry tetrahydroftiran (14 ml) at −35 to −30° C. The reaction mixture was stirred at this temperature for 0.5 hr, poured into water/ice (200 ml) and the mixture extracted with chloroform. The organic extracts were combined, dried over anhydrous sodium sulfate, filtered, and the filtrate was concentrated. The residue was dissolved in dichloromethane and high performance liquid chromatographed, eluting with dichloromethane (with a trace of ammonium hydroxide), followed by 2%, 3%, 4% and 8% methanol:dichloromethane (with a trace of ammonium hydroxide). The appropriate fractions were collected and concentrated to give 2.46 g (60%) of product, as the free base. The free base was dissolved in diethyl ether, filtered, and the filtrate was concentrated. The residue was dissolved in chloroform and diethyl ether, and ethereal hydrogen chloride was added. The precipitate was collected to give product, mp 185–187° C.

Analysis: Calculated for $C_{21}H_{29}NO_3S \cdot HCl$: 61.22%; C, 7.34%; H, 3.40%; N, Found: 60.94%; C, 7.23%; H, 3.24%; N.

EXAMPLE 9

4-Methoxy-3-propargyloxy-1-[(4-methylpiperazin-1-yl)methyl]benzenedihydrochloride To a solution of 4-methoxy-3-propargyloxybenzaldehyde (19.9 g) in 1,2-dichloroethane (210 ml) was added 1-methylpiperazine (11.7 ml), followed by 1,2-dichloroethane (210 ml) and sodium triacetoxyborohydride (32.5 g). The reaction mixture was stirred at ambient temperature for 2 hrs, poured into 10% sodium hydroxide/ice (1000 ml) and extracted with chloroform. The combined organic extracts were washed with water, dried over anhydrous sodium sulfate, filtered, and the filtrate was concentrated. The residue was dissolved in chloroform and high performance liquid chromatographed, eluting with chloroform, followed by 2%, 4%, 5% and 10% methanol:chloroform. The appropriate fractions were collected and combined to give 15.8 g (52.3%) of product, as the free base. The free base was dissolved in diethyl ether and ethereal hydrogen chloride was added. The precipitate was collected to give product, mp 220–223° C. (dec).

Analysis: Calculated for $C_{16}H_{24}N_2O_2$: 55.34%; C, 6.97%; H, 8.07%; N, Found: 55.24%; C, 7.01%; H, 7.91%; N.

EXAMPLE 10

4-Methoxy-3-propargyloxy-1-[[(methyl)(phenethyl) amino]methyl]benzene Citrate To a solution of 4-methoxy-3-propargyloxybenzaldehyde (19.9 g) in 1,2-dichloroethane (210 ml) was added N-methylphenethylamine (15.3 ml), sodium triacetoxyborohydride (33.3 g) and 1,2-dichloroethane (210 ml), with stirring. The reaction mixture was stirred at ambient temperature, under nitrogen, for 1 hr, poured into 10% sodium hydroxide/ice (1000 ml) and extracted with chloroform. The organic extracts were combined and washed with water, dried over anhydrous sodium sulfate, filtered, and the filtrate was concentrated. The residue was dissolved in chloroform and high performance liquid chromatographed, eluting with chloroform, followed by 2.5% methanol:chloroform. The appropriate fractions were collected and concentrated to give 15.3 g (47%) of product, as the free base. The free base was dissolved in diethyl ether and ethereal citric acid was added. The precipitate was collected to give product, mp 45–65° C.

Analysis: Calculated for $C_{26}H_{31}NO_9$: 62.27%; C, 6.23%; H, 2.79%; N, Found: 61.66%; C, 6.51%; H, 2.74%; N.

EXAMPLE 11

4-Methanesulfonyloxy-3-(propargyloxy) benzaldehyde

To a stirred suspension of sodium hydride (2.52 g) in dry dimethylformamide (56 ml) at a water bath temperature of 20° C. was added, dropwise, a solution of 3-hydroxy-4-methanesulfonyloxybenzaldehyde (14.0 g) in dimethylformamide(56 ml) at a rate such that the reaction temperature remained below 25° C. The reaction mixture was stirred for 5 mins, cooled in an ice/salt bath to 0–5° C., and a solution of propargyl bromide (7 ml) in dimethylformamide (56 ml) was added dropwise. The mixture was stirred at 0–5° for 0.5 hr, poured into ice/water and extracted with chloroform. The layers were separated, sodium carbonate was added to the aqueous phase and the aqueous phase was extracted with chloroform. The combined chloroform extracts were dried over anhydrous sodium sulfate, filtered, and the filtrate was concentrated. The residue was dissolved in ethyl acetate, washed with cold 10% sodium hydroxide solution, filtered and concentrated. The residue was dried at 80° C. under high vacuum to give 7.0 g (43.8%) of product. Recrystallizationfrom ethanol gave the analytical sample, mp 81–83° C.

Analysis: Calculated for: $C_{11}H_{10}O_5S$: 51.96%; C, 3.96%; H, Found: 51.80%; C, 3.81%; H.

EXAMPLE 12

4-[3-[2-Methoxy-5-(4-methylpiperazin-1-ylmethyl) phenoxy]prop-1-ynyl]tetrahydrothiopyran-4-ol Dihydrochloride Dihydrate To a solution of 4-methoxy-3-propargyloxy-1-[(4-methylpiperazin-1-yl)methyl]benzene (5.69 g) in dry tetrahydrofuran (25 ml) at 0° to 5° C. was added 2.2 M n-butyllithium (9.50 ml) over 30 mins at a rate such that the internal temperature remained below 0° C. The reaction mixture was stirred at 0° C. for 20 mins, chilled to −30° to −35° C., and after stirring at this temperature for 20 mins, tetrahydrothiopyran-4-one (2.29 g) in dry tetrahydrdfuran (25 ml) was added over 15 mins. The reaction mixture was stirred at −30° to −35° C. for 30 mins, poured into ice/water (250 ml), and the mixture was extracted with chloroform. The combined organic extracts were dried over anhydrous sodium sulfate, filtered, and the filtrate was concentrated. The residue was dissolved in methylene chloride and high performance liquid chromatographed, eluting with methylene chloride (with a trace of ammonium hydroxide), followed by 2.5% methanol:methylene chloride (with a trace of ammonium hydroxide). The appropriate fractions were collected and concentrated to give 4.37 g (52%) of product, as the free base. The free base was dissolved in ether and ethereal hydrogen chloride was added. The precipitate was collected to give product, mp 230–232° C. (dec.).

Analysis: Calculated for $C_{21}H_{36}Cl_2N_2O_5S$: 50.50%; C, 7.26%; H, 5.61%; N, Found: 50.97%; C, 7.12%; H, 5.52%; N.

EXAMPLE 13

4-[3-[2-Methoxy-5-[[(methyl)-2-phenethyl] aminomethyl]phenoxy]prop-1-ynyl] tetrahydrothiopyran-4-ol Hydrochloride Hydrate To a solution of 4-methoxy-3-propargyloxy-1-(N-(methyl-N-(phenethylamino)methyl]benzene(4.81 g) in dry tetrahydrofuran(21 ml) at 0° to 5° C. was added 2.2 M n-butyllithium (7.0 ml) over 30 mins at a rate such that the internal temperature remained below 0° C. The reaction mixture was stirred at 0° C. for 20 mins, chilled to –30° to –37° C., stirred at that temperature for 20 mins and tetrahydrothiopyran-4-one (1.70 g) in dry tetrahydrofuran (20 ml) was then added over 10 mins. The reaction mixture was stirred at –30° to –35° C. for 30 mins, poured into ice/water and the mixture was extracted with chloroform. The organic extracts were combined, dried over anhydrous sodium sulfate, filtered, and the filtrate was concentrated. The residue was high performance liquid chromatographed, eluting with niethylene chloride (with a trace of ammonium hydroxide), followed by 2.5% methanol:methylene chloride (with a trace of ammonium hydroxide). The appropriate fractions were collected and concentrated to give 4.73 g (72%) of product, as the free base. The free base was dissolved in diethyl ether and ethereal hydrogen chloride was added. The precipitate was collected to give product, mp 70–75° C.

Analysis: Calculated for $C_{25}H_{34}ClNO_4S$: 62.55%; C, 7.14%; H, 2.92%; N, Found: 63.02%; C, 6.96%; H, 2.93%; N.

EXAMPLE 14

4-[3-[2-Methoxy-5-(pyrrolidin-1-yl-methyl) phenoxy]prop-1-ynyl]cyclohexan-4-ol Citrate To a solution of 4-methoxy-3-propargyloxy-1-[(pyrrolidin-4-yl)methyl]benzene (8.96 g) in dry tetrahydrofuran (50 ml) at 0° to 5° C. was added dropwise, with stirring, 2.25 M n-butyllithium (16 ml) over a 0.5 hr. The mixture was stirred at this temperature for 0.5 hr, cooled to –45° C., and a solution of cyclohexanone (3.50 ml) in dry tetrahydrofuiran (50 ml) was added dropwise. The reaction mixture was stirred at –45° to –40° C. for 1 hr, poured into ice/water (250 ml) and extracted with chloroform. The organic extracts were combined, dried over anhydrous sodium sulfate, filtered, and the filtrate was concentrated. The residue was dissolved in methylene chloride and high performance liquid chromatographed, eluting with methylene chloride (with a trace of ammonium hydroxide), followed by 1%, 3%, 5%, 10% methanol:methylenechloride (with a trace of ammonium hydroxide). The appropriate fractions were collected and concentrated to give 5.55 g (44%) of product, as the free base. The free base was dissolved in diethyl ether and ethereal citric acid was added. The precipitate was collected to give product, mp 55–80° C.

Analysis: Calculated for $C_{27}H_{37}NO_{10}$: 60.55%; C, 6.96%; H, 2.62%; N, Found: 60.86%; C, 7.23%; H, 2.54%; N.

EXAMPLE 15

4-(Methanesulfonyloxy)-3-(propargyloxy)-1-(pyrrolidin-1-yl)methylbenzene Citrate To a solution of 4-(methanesulfonyloxy)-3-(propargyloxy) benzaldehyde (6.7 g) in 1,2-dichloromethane (135 ml) was added pyrrolidine (1.88 g) followed by sodium triacetoxyborohydride (7.37 g), with stirring. The reaction mixture was stirred at ambient temperature for 1.5 hrs and poured into ice/water/ dichloromethane. The layers were separated and the organic layer was washed with water and concentrated to give 6.37 g (94.9%) of product, as the free base. A 500 mg sample of product free base was dissolved in chloroform and flash column chromatographed (silica gel), eluting with chloroform, followed by 1%, 2%, and 5% methanol/ chloroform. The appropriate fractions were collected and evaporated. The residue was dissolved in ether and ethereal citric acid was added. The precipitate was collected to provide product, mp 33–59°.

Analysis: Calculated for $C_{21}H_{27}NO_4S$: 50.29%; C, 5.43% H, 2.79%; N, Found: 50.5 1%; C, 5.64%; H, 2.92%; N,

EXAMPLE 16

3-Methoxy-4-(triisopropylsiloxy)benzaldehyde, (pyridyl-2-yl)hydrazone Hydrochloride To a solution of 3-methoxy-4-triisopropylsilylbenzaldehyde (4.97 g) in 1,2-dichloroethane (34 ml) was added 2-hydrazinopyridine (1.77 g), followed by 1,2-dichloroethane (8.0 ml) and sodium triacetoxyborohydride (5.13 g) and 1,2-dichloroethane (13 ml), with stirring. The reaction mixture was stirred at ambient temperature for 3 hrs, poured into ice/water (200 ml) and extracted with chloroform. The organic extracts were combined, washed with sodium bicarbonate, dried over anhydrous sodium sulfate, filtered, and the filtrate was concentrated to provide 5.79 g (90.0%) of product, as the free base. The product free base was dissolved in chloroform/diethyl ether. Ethereal hydrogen chloride was added. The precipitate was collected to give product, mp 200–223° C. (dec).

Analysis: Calculated for $C_{22}H_{34}ClN_3O_2Si$: 60.60%; C, 7.86%; H, 9.64%; N, Found: 60.36%; C, 7.88%; H, 9.58%; N.

EXAMPLE 17

4-(Methylaminocarbonyloxy)-3-(propargyloxy)1-(pyrrolidinomethyl)benzene Citrate

To a suspension of 4-hydroxy-3-(propargyloxy) (pyrrolidinomethyl)benzene (0.351 g) in tetrahydrofuran (6 ml) and milled potassium carbonate (0.42 g) cooled in an ice bath was added methyl isocyanate (0.13 ml) by syringe. The suspension was stirred at 0–5° C. for 0.5 hr, allowed to warm to ambient temperature and stirred for an additional 0.5 hr. The suspension was filtered onto a silica gel column packed in chloroform and eluted with chloroform followed by 1% methanol/chloroform, 2%, 5%, and 10% methanol/ chloroform. The appropriate fractions were collected and concentrated to give 0.146 g (34%) of product, as the free base. The free base was dissolved in chloroform/ether, and ethereal citric acid was added. The precipitate was collected to give product, mp 52–66° C.

Analysis: Calculated for $C_{22}H_{28}N_2O_{10}$: 55.00%; C, 5.87%; H, 5.83%; N, Found: 54.84%; C, 6.00%; H, 5.98%; N.

EXAMPLE 18

4-(Methanesulfonyloxy)-3-methoxy-[(pyrrolidin-1-yl)-methyl]benzene Citrate

To a solution of 4-methanesulfonyloxy-3-methoxybenzaldehyde (5.0 g) in 1,2-dichloroethane (100 ml) was added pyrrolidine (1.65 ml) followed by sodium triacetoxyborohydride (5.5 g), with stirring. The reaction mixture was stirred for 1.5 hrs at ambient temperature, poured into ice/water/10% sodium hydroxide solution. The layers were separated, and the organic phase was washed with water and concentrated. The residue was dissolved in ether, extracted with 10% hydrochloric acid. The extract was neutralized with 10% sodium hydroxide solution, buffered with sodium bicarbonate, and extracted with ethyl acetate. The organic extract was washed with water, dried over anhydrous sodium sulfate, filtered, and the filtrate was concentrated to give 4.9 g (79%) of product, as the free base. The free base (300 mg) was dissolved in ether and ethereal citric acid was added. The precipitate was collected and dried at ambient temperature to give product, mp 43–62° C.

Analysis: Calculated for $C_{19}H_{27}NO_{11}S$: 47.79%; C, 5.70%; H, 2.93%; N, Found: 47.86%; C, 6.19%; H, 3.22%; N.

EXAMPLE 19

3-Methoxy-4-(methylaminocarbonyloxy)benzaldehyde, (pyridyl-2-yl)hydrazone

To a solution of 4-hydroxy-3-methoxybenzaldehyde, (pyridyl-2-yl)hydrazone (0.99 g) in tetrahydrofuran (10 ml) was added a solution of 1,1'-carbonyldiimidazole (0.99 g) in tetrahydrofuran (10 ml) by syringe, with stirring. The mixture was stirred at ambient temperature for 2.5 hrs, glacial acetic acid (4.0 ml) was added, followed by methylamine (0.40 ml), and the reaction mixture was stirred at ambient temperature for 6 hrs. The reaction mixture was poured into ice/water (300 ml) and extracted with ethyl acetate. The organic extracts were combined, dried over anhydrous sodium sulfate, filtered, and the filtrate was concentrated. The residue was dissolved in dichloromethane and methanol and flash chromatographed (silica gel), eluting with dichloromethane, followed by 1% methanol :dichloromethane (with a trace of ammonium hydroxide). The appropriate fractions were collected and concentrated. Recrystallization of the residue from ethanol gave 0.23 g (98%) of product, mp 202–204° C.

Analysis: Calculated for $C_{11}H_{16}N_4O_3$: 59.99%; C, 5.37%; H, 18.66%; N, Found: 59.76%; C, 5.48%; H, 18.74%; N.

EXAMPLE 20

4-Hydroxy-3-methoxybenzaldehyde, (pyridyl-2-yl)hydrazone

To a solution of 3-methoxy-4-(triisopropylsiloxy)benzaldehyde, (pyridyl-2-yl)hydrazone (3.94 g) in dry tetrahydrofuran (150 ml) was added tetrabutylammonium fluoride (3.70 ml) by syringe, with stirring. The reaction mixture was stirred at ambient temperature for 45 mins, tetrabutylammonium fluoride (3.70 ml) was added and the solution was stirred at ambient temperature for 1 hr and poured into ice/water. The mixture was extracted with chloroform. The organic extracts were combined, dried over anhydrous sodium sulfate, filtered, and the filtrate was concentrated. The residue was dissolved in dichloromethane and flash column chromatographed (silica gel, 3% methanol:dichloromethane)(with a trace of ammonium hydroxide). The appropriate fractions were collected and concentrated to give 2.19 g (90%) of product. Recrystallization from ethyl acetate gave the analytical sample, mp 126–130° C.

Analysis: Calculated for $C_{13}H_{13}N_3O_2$: 64.19%; C, 5.39%; H, 17.27%; N, Found: 64.1 0%; C, 5.25%; H, 16.95%; N,

EXAMPLE 21

3-Propargyloxy-1-(pyrrolidin-1-yl)methyl-3-(triisopropylsiloxy)benzene

To a solution of 3-hydroxy-1-(pyrrolidin-1-yl)methyl-3-hydroxybenzene (0.95 g) in dry dimethylformamide (5 ml) was added by syringe, with stirring, diisopropylbutylamine (1.1 ml) followed by triisopropylsilyl chloride (0.97 ml). The reaction mixture was stirred at ambient temperature for 1 hr, ice (10 g) was added and after stirring for 10 mins, the mixture was poured into ice/water and extracted with ethyl acetate. The extract was washed with water, saturated sodium chloride solution, dried over anhydrous sodium sulfate, filtered, and the filtrate was concentrated. The residue was flash column chromatographed (silica gel) eluting with dichloromethane, 1%, 2% and 5% methanol/dichloromethane. The appropriate fractions were collected and concentrated to give 0.65 g of product. Additional fractions were collected, concentrated and chromatographed over silica gel. Concentration of the appropriate fractions gave 0.15 g of product. Total yield 0.80 g (50%).

Analysis: Calculated for $C_{23}H_{31}NO_2Si$: 71.27%; C, 9.62%; H, 3.61%; N, Found: 70.48%; C, 9.78%; H, 3.55%; N.

EXAMPLE 22

4-Methoxy-3-propargyloxy-1-[[N-(methyl)-(3,4 dimethoxyphenethyl)amino]methyl]benzene Citrate Monohydrate To a solution of 4-methoxy-3-propargyloxybenzaldehyde (5.07 g) in 1,2-dichloroethane(50 ml) was added N-methylveratrylamine (4.9 ml) followed by sodium triacetoxyborohydride (8.48 g), with stirring. The reaction mixture was stirred at ambient temperature for 1 hr, 1,2-dichloroethane (50 ml) was added, and the reaction mixture stirred at ambient temperature for 0.5 hr. The reaction mixture was poured into ice/10% sodium hydroxide solution (250 ml) and extracted with chloroform. The organic extracts were combined, washed with water, dried over anhydrous sodium sulfate, filtered, and the filtrate was concentrated. The residue was dissolved in dichloromethane and high performance liquid chromatographed, eluting with 2% methanol:dichloromethane. The appropriate fractions were collected and concentrated to give 8.27 g (84%) of product, as the free base. The free base was dissolved in diethyl ether, and ethereal citric acid was added. The precipitate was collected to give product, mp 40–80° C.

Analysis: Calculated for $C_{28}H_{37}NO_{12}$: 58.02%; C, 6.43%; H, 2.42%; N, Found: 58.19%; C, 6.21%; H, 2.27%; N.

EXAMPLE 23

4-Methoxy-3-(propargyloxy)benzaldehyde, (pyridin-4-yl)hydrazone Hydrochloride To a solution of 4-methoxy-3-propargyloxybenzaldehyde (1.34 g) in 1,2-dichloroethane(20 ml) was added 4-hydrazinopyridine (0.77 g), 1,2-dichloroethane (8 ml) and sodium triacetoxyborohydride (2.25 g), with stirring. The reaction mixture was stirred at ambient temperature for 2 hrs, poured into 10% sodium hydroxide/water(200 ml) and extracted with chloroform. The combined organic extracts were washed with water, dried over anhydrous sodium sulfate, filtered, and the filtrate was concentrated. The residue was dissolved in methanol:dichloroethane and flash column chromatographed (silica gel, dichloroethane), eluting with dichloroethane, followed by 3%, 5%, 10% and 2,0% methanol:dichloroethane. The appropriate fractions were collected and combined to give 1.43 g (71.9%) of product, free base. The free base was dissolved in diethyl ether/chloroform and ethereal hydrogen chloride was added. The precipitate was collected to give product, mp 200–210° C. (dec).

Analysis: Calculated for $C_{16}H_{16}ClN_{23}O_2$: 60.48%; C, 5.08%; H, 13.22%; N, Found: 59.93%; C, 4.94%; H, 13.16%; N.

EXAMPLE 24

4-[3-[2-(Methylaminocarbonyloxy)-5-(pyrrolidin-1-yl-methyl)phenoxy]prop-1-ynyl] tetrahydrothiopyran-4-ol Citrate To a solution of 4-[3-[5-(pyrrolidin-1-yl-methyl)-2-(triisopropylsiloxy)phenoxy]prop-1-ynyl] tetrahydrothiopyran-4-ol (0.54 g) in tetrahydrofuran (5 ml) was added 1M tetra-n-butylammonium fluoride (0.41 ml), with stirring. The mixture was stirred for 15 mins at ambient temperature, lithium chloride (250 mg) was added and the suspension was stirred for 15 mins and methyl isocyanate (73.4 mg) was added by syringe. The reaction mixture was stirred at ambient temperature for 1 hr, poured into ice/water, extracted with chloroform, and the extracts were washed with water, dried over anhydrous sodium sulfate, filtered, and the filtrate was concentrated. The residue was dissolved in chloroform and flash column chromatographed (silica gel), eluting with chloroform, 1%, 2%, 5%, and 10% methanol/chloroform. The appropriate fractions were collected and concentrated. The residue was dissolved in chloroform/ether and ethereal citric acid was added. The precipitate was collected to give 0.215 g (33.6%) of product, mp 68–99° C.

Analysis: Calculated for $C_{27}H_{36}N_2O_{11}Si$: 54.35%; C, 6.08%; H, 4.70%; N, Found: 54.73%; C, 6.02%; H, 5.21%; N.

EXAMPLE 25

3-Methoxy-4-(triisopropylsiloxy)benzaldehyde, (pyridyl-4-yl)hydrazonehydrochloride To a solution of 3-methoxy-4-triisopropylsilylbenzaldehyde(3.55 g) in 1,2-dichloroethane (46 ml) was added 4-hydrazinopyridine (1.26 g), with stirring. The reaction mixture was stirred at ambient temperature for 10 mins, sodium triacetoxyborohydride (3.66 g) was added, and the reaction mixture was stirred at ambient temperature for 3.6 hrs. The reaction mixture was poured into 10% sodium hydroxide/ice (500 ml) and extracted with dichloromethane. The organic extracts were combined, washed with water, dried over anhydrous sodium sulfate, filtered, and the filtrate was concentrated. The residue was dissolved in dichloromethane and flash chromatographed (silica gel, 3% methanol:dichloromethane) (with a trace of ammonium hydroxide), eluting with 3% methanol:dichloromethane. The appropriate fractions were collected and concentrated to give 1.93 g (42%) of product, as the free base. The free base was dissolved in methanol/diethyl ether and ethereal hydrogen chloride was added. The precipitate was collected to give product, mp 256–262° C.

Analysis: Calculated for $C_{22}H_{34}ClN_3O_2Si$: 60.60%; C, 7.86%; H, 9.64%; N, Found: 60.26%; C, 7.76%; H, 9.62%; N.

EXAMPLE 26

4-Hydroxy-3-methoxybenzaldehyde, (pyridyl-4-yl) hydrazone

To a solution of 3-methoxy-4-(triisopropylsiloxy) benzaldehyde, (pyridyl-4-yl)hydrazone (1.01 g) in tetrahydrofuran (38 ml) was added 1M tetra-n-butylammonium fluoride in tetrahydrofuran (1.89 ml), with stirring. Tetrahydrofuran (30 ml) was added to the reaction mixture, and the suspension was stirred at ambient temperature for 1.5 hrs, poured into ice/water (100 ml) and extracted with chloroform. The organic extracts were combined, dried over anhydrous sodium sulfate, filtered, and the filtrate was concentrated. The residue was recrystallized from ethyl alcohol to give 0.33 g (54%) of product, mp 126–130° C.

Analysis: Calculated for $C_{13}H_{13}N_3O_2$: 64.19%; C, 5.39%; H, 17.27%; N, Found: 63.90%; C, 5.38%; H, 17.09%; N.

EXAMPLE 27

4-Methoxy-3-(propargyloxy)-1-[[4-(pyridin-2-yl) piperazin-1-yl]methyl]benzene Hydrochloride Monohydrate To a solution of 4-methoxy-3-(propargyloxy) benzaldehyde(1.02 g) in dry 1,2-dichloroethane (22 ml) was added 1-(2-pyridyl)piperazine (0.80 ml), with stirring, and the solution was stirred at ambient temperature for 10 mins. Sodium triacetoxyborohydride (1.73 g) was added, and the reaction mixture was stirred at ambient temperature for 3 hrs, poured into 10% sodium hydroxide/ice and extracted with dichloromethane. The organic extracts were combined, washed with water, dried over anhydrous sodium sulfate, filtered, and the filtrate was concentrated. The residue was dissolved in dichloromethane and flash chromatographed (silica gel), eluting with 3% methanol:dichloromethane followed by 4% methanol:dichloromethane. The appropriate fractions were collected and concentrated to give 1.41 g (78%) of product, as the free base. The free base was dissolved in diethyl ether and ethereal hydrogen chloride was added. The precipitate was collected to give product, mp 175–185° C.

Analysis: Calculated for $C_{20}H_{26}ClN_3O_3$: 61.30%; C, 6.69%; H, 10.72%; N,: Found: 61.63%; C, 6.45%; H, 10.54%; N.

EXAMPLE 28

1-(Aminomethyl)-3-methoxy-4-(triisopropylsiloxy) benzene Maleate

To a solution of 3-methoxy-4-(triisopropylsiloxy) benzonitrile(5.08 g) in methanol (100 ml) was added cobalt (II) chloride (4.30 g), with stirring, during which time the temperature increased 5° C. The reaction mixture was chilled to 5° C. in an ice bath. After 10 mins, sodium borohydride (6.30 g) was added very slowly, in small portions, over 40 mins as the internal temperature rose to between 10° to 15° C. 'After the addition was completed, the reaction mixture was stirred at 5° to 10° C. for 30 min, allowed to warm to ambient temperature and stirred for 2.5 hrs. The mixture was poured into ice/water (400 ml), cold hydrochloric acid (50 ml) (pH=2) was added, followed by ethyl acetate (1000 ml), 10% sodium hydroxide solution (70 ml) and sodium bicarbonate (pH=7). The suspension was filtered through celite and the filtrate was separated. The organic layer was dried over anhydrous sodium sulfate, filtered, and the filtrate was concentrated. The residue was dissolved in dichloromethane and flash chromatographed (silica gel) and 1% methanol:dichloromethane) (containing a trace of ammonium hydroxide) eluting with 1% followed by 3% and 5% methanol:dichloromethane(with a trece of ammonium hydroxide). The appropriate fractions were collected and concentrated to give 2.19 g (43%) of product, as the free base. The free base was dissolved in diethyl ether and ethereal maleic acid was added. The precipitate was collected to give product, mp 132–134° C.

Analysis: Calculated for $C_{21}H_{35}NO_6Si$: 59.27%; C, 8.29%; H, 3.29%; N, Found: 58.14%; C, 8.36%; H, 3.18%; N.

EXAMPLE 29

3-Cyanomethoxy-4-methoxy-1-[(pyrrolidin-1-yl)methyl]benzene

To a solution of 3-cyanomethoxy-4-methoxybenzaldehyde (10.0 g) in 1,2-dichloroethane (400 ml) was added pyrrolidine (6.6 ml), with stirring, followed by sodium triacetoxyborohydride (22 g). The reaction mixture was stirred at ambient temperature for 1 hr and poured into ice/water 10% sodium hydroxide solution. The mixture was extracted with ethyl acetate, washed with water, saturated sodium chloride solution, dried over anhydrous sodium sulfate, filtered, and the filtrate was concentrated. The residue was dissolved in dichloromethane and high performance liquid chromatographed, eluting with dichloromethane, 1%, 2% and 5% methanol/dichloromethane. The appropriate fractions were collected and concentrated to give 8.7 g (63.5%) of product as an oil.

Analysis: Calculated for $C_{14}H_{18}N_2O_2$: 68.27%; C, 7.37%; H, 11.37%; N, Found: 67.84%; C, 7.28%; H, 11.11%; N.

EXAMPLE 30

3-[2-Methoxy-5-[[4-(pyridin-2-yl)piperazin-1-yl]methyl]phenoxy(prop-1-ynyl)tetrahydrothiopyran-4-ol Hydrochloride Monohydrate To a solution of 4-methoxy-3-(propargyloxy)-1-[[4-(pyridin-2-yl)-piperazin-1-yl]methyl]benzene (1.81 g) dissolved in tetrahydrofuran (7.0 ml) at 0 to –5° C. was added 2.2 M n-butyllithium (2.4 ml), with stirring. The reaction mixture was stirred at 0 to –5° C. for 1 hr, cooled to –30 to –40° C. and stirred at –30° to –40° C. for 30 mins. Tetrahydrofuran-4-one (0.58 g) dissolved in tetrahydrofuran (7.0 ml) was added via syringe, and the mixture was stirred at –30 to –35° C. for 1.5 hr. The reaction mixture was poured into ice/water (50 ml) and extracted with chloroform. The organic extracts were combined, dried over anhydrous sodium sulfate, filtered, and the filtrate was concentrated. The residue was dissolved in dichloromethane and flash chromatographed (silica gel), eluting with dichloromethane, followed by 1, 2, 3, and 5% methanol:dichloromethane. The appropriate fractions were collected and concentrated to give 0.65 g (28%) of product, as the free base. The free base was dissolved in dichloromethane/diethyl ether and ethereal hydrogen chloride was added. The precipitate was collected to provide product, mp 190–201° C.

Analysis: Calculated for $C_{25}H_{34}ClN_3O_4S$: 59.10%; C, 6.75%; H, 8.27%; N, Found: 58.99%; C, 6.48%; H, 8.09%; N.

EXAMPLE 31

3-Ethoxycarbonylmethoxy-4-methoxy-1-pyrrolidinomethylbenzene Hydrochloride

To a solution of 3-ethoxycarbonylmethoxy-4-methoxybezaldehyde (10 g) in 1,2-dichloroethane (200 ml) was added pyrrolidine (3.51 ml), with stirring, followed by sodium triacetoxyborohydride(13.3 g). The reaction mixture was stirred at ambient temperature for approximately 50 mins, poured into ice, 10% sodium hydroxide solution and extracted with ethyl acetate. The extracts were washed with water, saturated sodium chloride solution, dried over anhydrous sodium sulfate, filtered, and the filtrate was concentrated. The residue was dissolved in dichloromethane and high performance liquid chromatographed. The appropriate fractions were collected and concentrated to give 7.98 g (79.8%) of product, as the free base. The free base was dissolved in chloroform/ether and ethereal hydrogen chloride was added. The precipitate was collected and recrystallized from 2-propanol to give product, mp 152–154° C.

Analysis: Calculated for $C_{16}H_{24}ClNO_4$: 58.27%; C, 7.33%; H, 4.25%; N, Found: 58.15%; C, 7.34%; H, 4.15%; N.

EXAMPLE 32

3-(2-Hydroxyethoxy)-3-(methoxy)pyrrolidinomethylbenzene

To 1M lithium aluminum hydride (12.6 ml) in tetrahydrofuran was added dry tetrahydrofuran(65 ml), followed by a solution of 3-ethoxycarbonylmethoxy-4-methoxy-1-pyrrolidinomethylbenzene (1.15 g) in dry tetrahydrofuran (65 ml), dropwise, with stirring. The reaction mixture was stirred at ambient temperature for 50 mins and then cooled in an ice bath. Water (12.6 ml) was slowly added dropwise and the mixture was poured into degassed ice/water, shaken with ammonium chloride solution and treated with sodium carbonate solution and extracted with ethyl acetate. The organic extracts were washed with water, saturated sodium chloride solution, dried over anhydrous sodium sulfate, filtered and the filtrate was concentrated to give 0.43 g (44%) of product. Recrystallization from cyclohexane gave the analytical sample, mp 55–57° C.

Analysis: Calculated for $C_{14}H_{21}NO_3$: 66.91%; C, 8.42%; H, 5.57%; N, Found: 66.70%; C, 8.35%; H, 5.45%; N.

EXAMPLE 33

2-(3,4-Dimethoxyphenylmethylamino)imidazoline Hydroiodide

To a stirred suspension of 2-methylthio-2-imidazoline hydroiodide (2.00 g) in chloroform (9.0 ml) was added veratrylamine (1.3 ml). The reaction mixture was heated under reflux for 2 hrs and stirred at ambient temperature overnight. The precipitate was collected and dried to give 1.86 g (97%) of product. Recrystallizationfrom ethanol provided the analytical sample, mp 178–180° C.

Analysis: Calculated for $C_{12}H_{18}IN_3O_2$: 39.68%; C, 5.00%; H, 11.57%; N, Found: 39.63%; C, 4.97%; H, 11.28%; N.

EXAMPLE 34

3-[2-Methoxy-5-[[N-(3,4-dimethoxyphenylethyl)]-[N-(methyl)]aminomethyl]phenoxyl](prop-1-ynyl)tetrahydrothiopyran-4-ohydrochloride A solution of 4-methoxy-3-propargyloxy-1-[[N-(methyl)-N-(3,4-dimethoxyphenylethyl)amino]methyl]benzene (0.928 g) in dry tetrahydrofuran (4.5 ml) was chilled in an ice salt bath to 0° to –5° C. 2.2 M n-butyllithium (1.1 ml) was added very slowly via syringe. The mixture was stirred for 45 mins, chilled to –30° C. to –50° C. and tetrahydrothiopyran-4-one (0.276 g) in dry tetrahydrofuran (2.0 ml) was added. After the addition was complete, the reaction mixture was stirred at –30 to –50° C. for 1 hr, poured into ice/water (50 ml) and extracted with dichloromethane. The combined organic extracts were dried over anhydrous sodium sulfate, filtered, and the filtrate was concentrated. The residue was dissolved in a minimal volume of 2% methanol:dichloromethane (with a trace of ammonium hydroxide) and flash chromatographed (silica gel), eluting with 2% and 5% methanol:dichloromethane/trace of ammonium hydroxide. The appropriate fractions were collected and concentrated to give 0.670 g (55%) of product, as the free base. The free base was dissolved in chloroform/diethyl ether and ethereal hydrogen chloride was added. The precipitate was collected to provide product, mp 55–80° C. (dec).

Analysis: Calculated for $C_{27}H_{36}ClNO_5S$: 62.11%; C, 6.95%; H, 2.68%; N, Found: 61.77%; C, 6.76%; H, 2.67%; N.

EXAMPLE 35

4-[[3-Methoxy-4-(methylaminocarbonyloxy)]phenylmethyl]-1-(pyridin-2-yl)piperazine Hydrochloride Monohydrate To a solution of 3-methoxy-4-(methylaminocarbonyloxy)benzaldehyde (1.98 g) in 1,2-dichloroethane (40 ml) was added 1-(2-pyridyl)piperazine (1.5 ml), followed by sodium triacetoxyborohydride (3.04 g), with stirring. The reaction mixture was stirred at ambient temperature for 3 hrs, poured into ice/saturated sodium carbonate solution (100 ml) and extracted with dichloromethane. The combined organic extracts were washed with water, dried over anhydrous sodium sulfate, filtered, and the filtrate was concentrated. The residue was dissolved in dichloromethane and flash chromatographed (silica gel) (with a trace of ammonium hydroxide), eluting with 1% methanol:dichloromethane (containing a trace of ammonium hydroxide), followed by 2% and 5% methanol:dichloromethane (with ammonium hydroxide). The appropriate fractions were collected and concentrated to give 1.67 g (50%) of product, as the free base. The free base was dissolved in diethyl ether and ethereal hydrogen chloride was added. The precipitate was collected to provide product, mp 120–140° C.

Analysis: Calculated for $C_{19}H_{21}ClN_4O_4$: 55.54%; C, 6.62%; H, 13.63%; N, Found: 55.27%; C, 6.47%; H, 13.28%; N.

EXAMPLE 36

6,7-Dimethoxy-N-[(4-methoxy)-3-(propargyloxy)phenylmethyl]-1,2,3,4-tetrahydroisoquinoline Hydrochloride To a solution of 4-methoxy-3-(propargyloxy)benzaldehyde (2.37 g) in 1,2-dichloroethane (25 ml) was added a solution of 6,7-dimethoxy-1,2,3,4-tetrahydroisoquinoline (2.40 g) in 1,2-dichloroethane (5.0 ml), followed by sodium triacetoxyborohydride (3.94 g), with stirring. The reaction mixture was stirred at ambient temperature for 5 hrs, poured into ice/saturated sodium carbonate solution (100 ml) and extracted with dichloromethane. The combined organic extracts were washed with water, dried over anhydrous sodium sulfate, filtered, and the filtrate was concentrated. The residue was dissolved in dichloromethane and flash chromatographed (silica gel), and eluting with 1%, methanol:dichloromethane containing a trace of ammonium hydroxide, followed by 2% and 3% methanol:dichloromethane. The appropriate fractions were collected and concentrated to give 1.51 g (33%) of product, as the free base. The free base was dissolved in diethyl ether and ethereal hydrogen chloride was added. The precipitate was collected to provide product, mp 220–222° C. (dec).

Analysis: Calculated for $C_{22}H_{26}ClNO_4$: 65.42%; C, 6.49%; H, 3.47%; N, Found: 65.28%; C, 6.57%; H, 3.36%; N.

EXAMPLE 37

4-Benzyloxy-3-[(ethoxycarbonyl)methoxy]benzaldehyde

To a solution of 4-benzyloxy-3-hydroxybenzaldehyde (0.5 g) in acetone (12.5 ml) was added milled potassium carbonate (1.20 g) and ethyl bromoacetate (0.48 ml), with stirring. The reaction mixture was heated under reflux for ~1 hr, with stirring, poured into ice/water and extracted with ethyl acetate. The extracts were washed with water, saturated sodium chloride solution, dried over anhydrous sodium sulfate, filtered, and the filtrate was concentrated. The residue was dissolved in dichloromethane and flash chromatographed (silica gel), eluting with dichloromethane, followed by 1% methanol:dichloromethane). The appropriate fractions were collected and combined to give 0.63 g (98%) of product, mp 36–43° C.

Analysis: Calculated for $C_{18}H_{18}O_5$: 68.78%; C, 5.77%; H, Found: 68.95%; C, 5.76%; H.

EXAMPLE 38

4-[[4-Methoxy-3-(methylaminocarbonyloxy)]phenylmethyl]-1-(pyridin-2-yl)piperazine Dihydrochloride To a solution of 4-methoxy-3-(methylaminocarbonyloxy)benzaldehyde (2.00 g) in 1,2-dichloroethane (40 ml) was added 1-(2-pyridyl)-piperazine (1.50 ml), followed by sodium triacetoxyborohydride (3.04 g), with stirring. The reaction mixture was stirred at ambient temperature for 3 hrs, poured into ice/saturated sodium carbonate solution (100 ml) and extracted with chloroform. The combined organic extracts were washed with water, dried over anhydrous sodium sulfate, filtered, and the filtrate was concentrated. The residue was dissolved in dichloromethane and flash chromatographed (silica gel), eluting with 1% followed by 3% and 5% methanol:dichloromethane, containing a trace of ammonium hydroxide. The appropriate fractions were collected and combined to give 2.73 g (80%) of product, as the free base. The free base was dissolved in chloroform/diethyl ether and ethereal hydrogen chloride was added. The precipitate was collected to give 'product, mp 235–237° C. (dec).

Analysis: Calculated for $C_{19}H_{26}Cl_2N_4O_3$: 53.15%; C, 6.10%; H, 13.85%; N, Found: 52.76%; C, 6.16%; H, 12.84%; N.

EXAMPLE 39

4-[[4-Benzyloxy-3-(ethoxycarbonylmethoxy)phenyl]methyl]-1-(pyridin-2-yl)piperazine Dihydrochloride To a solution of 4-benzyloxy-3-(ethoxycarbonylmethoxy)benzaldehyde (0.2 g) in dichloroethane (4 ml) was added (pyridin-2-yl)piperazine (0.12 ml) and sodiumtriacetoxy borohydride (0.25 g), with stirring. The reaction mixture was stirred at ambient temperature for 1.5 hrs, poured into ice/saturated sodium bicarbonate solution and extracted with ethyl acetate. The extracts were washed with water, saturated sodium chloride solution, dried over anhydrous sodium sulfate, filtered, and the filtrate was concentrated. The residue was dissolved in dichloromethane and flash chromatographed (silica gel), eluting with dichloromethane, 1% and 2% methanol/dichloromethane. The appropriate fractions were collected and concentrated. The residue was dissolved in ether and ethereal hydrochloric acid was added. The suspension was filtered and the filter cake dried for 2 hrs at ambient temperature. Recrystallization from ethanol provided 0.143 g (42.1%) of product, mp 151–191° C.

Analysis: Calculated for $C_{27}H_{33}Cl_2N_3O_4$: 60.68%; C, 6.22%; H, 7.86%; N, Found: 60.42%; C, 5.99%; H, 7.77%; N.

EXAMPLE 40

4-[[4-(Dimethylaminocarbonyloxy)-3-(methoxylphenyl]methyl]-1-(pyridin-2-yl)piperazine To a solution of 4-(dimethylaminocarbonyloxy)-3-methoxybenzaldehyde (0.5 g) in dichloroethane (20 ml) was added (pyridin-2-yl)piperazine (0.62 ml) followed by sodium triacetoxyborohydride (1.28 g), with stirring. The mixture was stirred at ambient temperature for 1 hr, poured into ice/aqueous sodium carbonate solution and extracted with ethyl acetate. The extracts were washed with water, saturated sodium chloride solution, dried over anhydrous sodium sulfate, filtered, and the filtrate was concentrated. The residue was crystallized from ether. The crystals were collected by filtration and dried overnight at ambient temperature to provide 0.47 g (38.6%) of product, mp 140–145° C.

Analysis: Calculated for $C_{20}H_{26}N_4O_3$: 64.85%; C, 7.07%; H, 15.12%; N, Found: 64.68%; C, 6.99%; H, 15.02%; N.

EXAMPLE 41

3-Methoxy-4-[2-(phenyl)ethylaminocarbonyloxy]benzaldehyde

To a solution of vanillin (2.01 g), milled potassium carbonate (3.63 g) and tetrahydrofuran (60 ml), chilled in an ice bath at 0° to −5° C. for 15 mins, was added alpha-2-methylbenzylisocyanate (2.37 ml) via syringe, with stirring. The reaction mixture was stirred at 0° to −5° C. for 15–20 mins at ambient temperature for 2 hrs, and then filtered. The residue was dissolved in a minimal volume of chloroform and flash chromatographed (silica gel), eluting with 5% methanol:chloroform. The appropriate fractions were collected and evaporated to give 3.65 g (92%) of product. Recrystallization from 2-propanol gave the analytical sample, mp 133–138° C.

Analysis: Calculated for $C_{11}H_{17}NO_4$: 68.22%; C, 5.72%; H, 4.68%; N, Found: 68.17%; C, 5.73%; H, 4.63%; N.

EXAMPLE 42

2-[3-Methoxy-4-(methylaminocarbonyloxy)phenylmethyl]-1-(6,7-dimethoxy)-1,2,3,4-tetrahydroisoquinoline Hydrochloride To a suspension of 3-methoxy-4-(methylaminocarbonyloxy)benzaldehyde (3.50 g) in 1,2-dichloroethane (67 ml) was added 6,7-dimethoxy-1,2,3,4-tetrahydroisoquinoline (3.23 g) and sodium triacetoxyborohydride (5.32 g). The reaction mixture was stirred at ambient temperature for 22 hrs, poured into saturated ice/sodium carbonate solution (100 ml) and extracted with chloroform. The combined organic extracts were washed with water and saturated sodium chloride solution, dried over anhydrous sodium sulfate, filtered, and the filtrate was concentrated. The residue was dissolved in dichloromethane and flash chromatographed (silica gel) eluting with dichloromethane followed by 1% methanol:dichloromethane. The appropriate fractions were collected and concentrated to give 3.52 g (54%) of product, as the free base. To the free base in chloroform/diethyl ether was added ethereal hydrogen chloride. The precipitate was collected to give product, mp 205–208° C. (dec).

Analysis: Calculated for $C_{21}H_{27}ClN_2O_5$: 59.64%; C, 6.44%; H, 6.62%; N, Found: 59.47%; C, 6.44%; H, 6.34%; N.

EXAMPLE 43

4-[[4-(Benzyloxy)-3-(2-hydroxyethoxy)]phenylmethyl]-1-(pyridin-2-yl)piperazine To a solution of 1M lithium aluminum hydride (2.47 ml) in tetrahydrofuran was added dropwise a solution of 4-[[4-benzyloxy)-3-(ethoxycarbonylmethoxy)]phenylmethyl]-1-(pyridine-2-yl)piperazine(1.14 g) in dry tetrahydrofuran(20 ml), with stirring. The reaction mixture was stirred for 3 hrs at ambient temperature, cooled in an ice bath and water (1 ml), 10% sodium hydroxide solution (1 ml) and water (3 ml) were added slowly dropwise. The mixture was stirred for several mins, filtered and the filtrate was poured into ice/water and extracted with ethyl acetate. The extracts were washed with water, saturated sodium chloride solution, dried over anhydrous sodium sulfate, filtered and the filtrate was concentrated. The residue was dissolved in dichloromethane and flash chromatographed on silica gel, eluting with dichloromethane, followed by 1%, 2%, and 5% methanol/dichloromethane. The appropriate fractions were collected and concentrated to give 0.87 g (85%) of product, mp 90–95° C.

Analysis: Calculated for $C_{25}H_{29}N_3O_3$: 71.58%; C, 6.97%; H, 10.02%; N, Found: 71.69%; C, 6.95%; H, 9.95%; N.

EXAMPLE 44

N-(2-Bromo-5-hydroxy-4-methoxy)benzyl-N'-(pyridin-2-yl)-piperazine

Sodium hydride (80%) (1.38 g) was added to a solution of 4-bromo-5-bromomethyl-2-methoxyphenol (2.61 g) and N-(2-pyridinyl)-piperazine (1.61 ml) in dichloromethane (150 ml) at 0° C. The reaction mixture was warmed to ambient temperature overnight, with stirring, quenched with water, and the mixture was concentrated in vacuo. The residue was dissolved in ethyl acetate and washed with brine. The aqueous layer was separated and extracted with ethyl acetate and washed with brine. The aqueous layer was extracted with ethyl acetate, and the combined organic extracts were dried over anhydrous sodium sulfate, filtered, and the filtrate was concentrated. The residue was flash column chromatographed (silica gel), eluting with 0–5% methanol/dichloromethane. The appropriate fractions were collected and concentrated to afford 1.88 g (56%) of product. Recrystallization from ethyl acetate/heptane gave the analytical sample, mp 122–124° C.

Analysis: Calculated $C_{17}H_{20}BrN_3O_2$: 53.98%; C, 5.33%; H, 11.11%; N, Found: 54.05%; C, 5.34%; H, 10.84%; N.

EXAMPLE 45

2-[4-(Dimethylaminocarbonyloxy)-3-(methoxy)phenylmethyl]-6,7-dimethoxy-1,2,3,4-tetrahydroisoquinoline To a solution of 4-(dimethylaminocarbonyloxy)-3-(methoxy)benzaldehyde (1.02 g) in 1,2-dichloroethane (16 ml) was added 6,7-dimethoxytetrahydroisoquinoline(0.97 g) and sodium triacetoxyborohydride (1.35 g), with stirring. The mixture was stirred at ambient temperature for 1 hr, poured onto ice/sodium carbonate solution and extracted with ethyl acetate. The extracts were washed with water, saturated sodium chloride solution, dried over anhydrous sodium sulfate, filtered, and the filtrate was concentrated. The residue was dissolved in dichloromethane and flash column chromatographed (silica gel), eluting with dichloromethane, 1% and 2% methanol dichloromethane. The appropriate fractions were collected and concentrated to give 0.92 g (50.3%/o) of product. Recrystallization from ethyl acetate gave the analytical sample, mp 126–128° C.

Analysis: Calculated for $C_{22}H_{21}N_2O_5$: 65.98%; C, 7.05%; H, 6.99%; N, Found 65.85%; C, 7.02%; H, 6.75%; N.

EXAMPLE 46

4-[3-(Methoxy)-4-[(1,2,3,4-tetrahydroisoquinolin-2-yl)carbonyloxy]phenylmethyl]-1-(pyridin-2-yl)piperazine To a solution of [3-methoxy-4-(1,2,3,4-tetrahydroisoquinolin-2-yl) carbonyloxy]benzaldehyde (0.76 g) in 1,2-dichloroethane, (10 ml) was added 1-(2-pyridyl)piperazine (0.37 ml) followed by sodium triacetoxyborohydride (0.78 g), with stirring. The suspension was stirred at ambient temperature for 3.5 hrs, poured into ice/saturated sodium carbonate solution (50 ml) and extracted with dichloromethane. The combined organic extracts were washed with water, saturated sodium chloride solution, dried over anhydrous sodium sulfate, filtered, and the filtrate was concentrated. The residue was dissolved in dichloromethane and flash column chromatographed (silica gel, dichloromethane) (with a trace of ammonium hydroxide), eluting with dichloromethane containing a trace of ammonium hydroxide, followed by 1% methanol:dichloromethane (with ammonium hydroxide). The appropriate fractions were collected and concentrated to give 0.72 g (64%) of product. Recrystallization from ethyl acetate gave the analytical sample, 125–127° C.

Analysis: Calculated for $C_{21}H_{30}N_4O_3$: 70.72%; C, 6.59%; H, 12.22%; N, Found: 70.65%; C, 6.77%; H, 11.90%; N.

EXAMPLE 47

4-[[4-Hydroxy-3-(methoxy)]phenylmethyl]-1-(pyridin-2-yl)piperazinedihydrochloride To a solution of 20% sodium hydroxide (50 ml) was added 4-[[3-methoxy-4-(methylaminocarbonyloxy]phenylmethyl]-1-(pyridin-2-yl)piperazine (2.43 g) in methanol (50 ml), with stirring. The reaction mixture was stirred at ambient temperature for 25 hrs and ice/saturated sodium bicarbonate solution-(100 ml) was added. The mixture was extracted with chloroform. The combined organic extracts were washed with water and brine, dried over anhydrous sodium sulfate, filtered, and the filtrate was concentrated to give 1.26 g (62%) of product, free base. The free base was recrystallized from ethyl acetate and treated with ethereal hydrogen chloride to give the analytical sample, mp 120–190° C.

Analysis: Calculated for $C_{11}H_{23}Cl_2N_3O_2$: 54.85%; C, 6.23%; H, 11.29%; N, Found: 55.27%; C, 6.79%; H, 11.36%; N.

EXAMPLE 48

2-[3-Hydroxy-4-(methoxy)phenylmethyl]-1-(6,7-dimethoxy)-1,2,3,4-tetrahydroisoquinoline Hydrochloride To a solution of 20% sodium hydroxide (40 ml) was added a solution of 2-[4-methoxy-3-(methylaminocarbonyloxy)phenylmethyl]-1-(6,7-dimethoxy)-1,2,3,4-tetrahydroisoquinoline (2.23 g) in methanol (40 ml), with stirring. The reaction mixture was stirred at ambient temperature for 17 hrs, ice/saturated sodium carbonate solution (100 ml), was added and the mixture was extracted with chloroform. The combined organic extracts were washed with water and brine, dried over anhydrous sodium sulfate, filtered, and the filtrate was concentrated to give 1.23 g (60%) of product, free base. The free-base was dissolved in diethyl ether and ethereal hydrogen chloride was added. The precipitate was collected and recrystallized from 2-propanol to give the analytical sample, mp 160–163° C. (dec).

Analysis: Calculated for $C_{19}H_{24}ClNO_4$: 62.38%; C, 6.61%; H, 3.83%; N, Found: 62.72%; C, 6.58%; H, i 3.90%; N.

EXAMPLE 49

1-[[4-(Dimethylaminocarbonyloxy)-3-(methoxy)phenyl]methyl]-4-(2-methoxyphenyl)piperazine Dihydrochloride To a solution of 4-(dimethylaminocarbonyloxy)-3-(methoxy)benzaldehyde (0.5 g) in 1,2 dichloroethane (9 ml) was added 2-methoxyphenylpiperazine (0.47 g) and sodium triacetoxyborohydride (0.66 g), with stirring. The reaction mixture was stirred at ambient temperature for 3 hrs, poured into ice/sodium carbonate solution and the layers separated. The organic layer was washed with water, saturated sodium chloride solution, dried over anhydrous sodium sulfate, filtered, and the filtrate was concentrated. The residue was dissolved in dichloromethane and flash column chromatographed (silica gel), eluting with dichloromethane, 1%, 2%, and 5% methanol/dichloromethane. The appropriate fractions were collected and concentrated. The residue was dissolved in chloroform and flash chromatographed (silica gel), eluting with chloroform, 1% methanol/chloroform and 2% methanol/chloroform. The appropriate fractions were collected and concentrated to give 0.53 g (59.4%) of product, as the free base. The free base was dissolved in chloroform/ethyl and ethereal hydrogen chloride was added. The precipitate was collected and recrystallized from 2-propanol to give product, mp 196–206° C.

Analysis: Calculated for $C_{22}H_{31}Cl_2N_3O_4$: 55.93%; C, 6.61%; H, 8.89%; N, Found: 56.12%; C, 6.58%; H, 8.90%; N.

EXAMPLE 50

1-[[4-(Dimethylaminocarbonyloxy)-3-(methoxy)phenyl]methyl-4-(4-methoxyphenyl)piperazine Dihydrochloride To a solution of 4-(dimethylaminocarbonyloxy)-3-methoxybenzaldehyde (0.5 g) in 1,2-dichloroethane (9 ml) was added 4-methoxyphenylpiperazine (0.5 g) and sodium triacetoxyborohydride (0.66 g), with stirring. The reaction mixture was stirred at ambient temperature for 13 hrs, poured into ice/sodium carbonate solution, and extracted with ethyl acetate. The extract was washed with water, saturated sodium chloride solution, dried over anhydrous sodium sulfate, filtered, and the filtrate was concentrated. The residue was dissolved in dichloromethane and flash chromatographed (silica gel), eluting with dichloromethane, 1% and 2% methanol/dichloromethane. The appropriate fractions were collected and concentrated. The residue was dissolved in chloroform and flash chromatographed (silica gel), eluting with chloroform, 1% methanol/chloroform and 2% methanol/chloroform. The appropriate fractions were collected and concentrated to give 0.57 g (63%) of product, as the free base. The free base was dissolved in chloroform/ether and ethereal hydrogen chloride was added. The precipitate was collected and recrystallized from 2-propanol to give the analytical sample, mp 193–199° C.

Analysis: Calculated for $C_{22}H_{31}Cl_2N_3O_4$: 55.93%; C, 6.61%; H, 8.89%; N, Found: 56.05%; C, 7.00%; H, 8.73%; N.

EXAMPLE 51

1-[[4-(Dimethylaminocarbonyloxy)-3-(methoxy) phenyl]methyl-4-(3-methoxyphenyl)piperazine Hydrochloride Hydrate To a solution of 4-(dimethylaminocarbonyloxy)-3-(methoxy)benzaldehyde (0.5 g) in 1,2-dichloromethane (9 ml) was added 1-(3-methoxyphenyl)piperazine (0.48 g) in 1,2-dichloroethane (1 ml) and sodium triacetoxyborohydride (0.66 g), with stirring. The reaction mixture was stirred at ambient temperature for 16 hrs, poured into ice/sodium carbonate solution and extracted with ethyl acetate. The extracts were washed with water, saturated sodium chloride solution, dried over anhydrous sodium sulfate, filtered, and the filtrate was concentrated. The residue was flash chromatographed (silica gel), eluting with chloroform, 1% and 2% methanol:chloroform. The appropriate fractions were collected and concentrated. The residue was flash chromatographed as above. The residue was dissolved in chloroform/ether and ethereal hydrogen chloride was added. The precipitate was collected to give the analytical sample, mp 144–153° C.

Analysis: Calculated for $C_{22}H_{32}ClN_3O_5$: 58.21%; C, 7.11%; H, 9.26%; N, Found: 58.20%; C, 7.11%; H, 9.09%; N.

EXAMPLE 52

2-[[4-Hydroxy-3-(methoxy)phenyl]methyl]-6,7-dimethoxy)-1,2,3,4-tetrahydroisoquinoline Hydrochloride To a solution of 20% sodium hydroxide (34 ml) was added a solution of 2-[[3-methoxy-4-(methylaminocarbonyloxy)phenyl]methyl]-(6,7-dimethoxy)-1,2,3,4-tetrahydroisoquinoline (1.88 g) in methanol (34 ml), with stirring. The reaction mixture was stirred at ambient temperature for 23 hrs, poured into ice/saturated sodium carbonate solution (50 ml) and extracted with chloroform. The combined organic extracts were washed with water and saturated sodium chloride solution, dried over anhydrous sodium sulfate, filtered, and the filtrate was concentrated to give 0.52 g (32%) of product, free base. The free base was dissolved in ether and treated with ethereal hydrogen chloride. The precipitate was collected and recrystallized from acetonitrile to give product, mp 210–218° C. (dec).

Analysis: Calculated for $C_{19}H_{24}ClNO_4$: 62.38%; C, 6.61%; H, 3.83%; N, Found: 61.90%; C, 6.70%; H, 4.35%; N.

EXAMPLE 53

4-[[4-(Hydroxy)-3-(2-hydroxyethyl)]phenylmethyl]-1-(pyridin-1-yl)piperazine Dihydrochloride Hydrate To 10% palladium-on-carbon (35 mg) in glacial acetic acid (1 ml) was added a solution of 4-[[4-(benzyloxy)-3-(2-hydroxyethyl)]phenylmethyl]-1-(pyridine-2-yl)piperazine (176 mg) in glacial acetic acid (1 ml). The mixture was stirred under 1 atm of hydrogen for 6 hrs. The suspension was filtered and concentrated. The residue was dissolved in chloroform and flash chromatographed (silica gel), eluting with chloroform, 1% methanol, 2% methanol and 5% methanol/chloroform. The appropriate fractions were collected and concentrated to give 119 mg (86%) of product, as the free base. The free base was dissolved in chloroform/ether and ethereal hydrogen chloride was added. The precipitate was collected, dried for 2 hrs at ambient temperature and recrystallized from isopropyl alcohol to give product, mp 120–167° C.

Analysis: Calculated for $C_{18}H_{27}Cl_{12}N_3O_4$: 51.43%; C, 6.47%; H, 10.00%; N, Found: 51.86%; C, 6.71%; H, 9.94%; N.

EXAMPLE 54

4-[[[4-(Methylaminocarbonyloxy)-3-(methoxy)] phenyl]methyl]-1-(pyrimidin-2-yl)piperazine Hydrochloride To a mixture of 4-(methylaminocarbonyloxy)-3-(methoxy)benzaldehyde (0.94 g) in 1,2-dichloroethane (16 ml) was added a solution of pyrazin-2-yl-piperazine (0.85 g) in dichloroethane (2 ml) and sodium triacetoxyborohydride (1.32 g), with stirring. The reaction mixture was stirred for 3 hrs at ambient temperature, poured into ice/sodium carbonate solution and extracted with ethyl acetate. The extracts were washed with water, saturated sodium chloride solution, dried over anhydrous sodium sulfate, filtered, and the filtrate was concentrated. The residue was dissolved in chloroform and flash chromatographed (silica gel), eluting with chloroform and 1%, 2% and 5% methanol:chloroform. The appropriate fractions were collected and concentrated to give 0.87 g (54%) of product, as the free base. The free base was dissolved in chloroform/etherand ethereal hydrogen chloride was added. The precipitate was collected and recrystallized from ethanol to give the analytical sample of the product, mp 231–235° C.

Analysis: Calculated for $C_{18}H_{24}ClN_5O_3$: 54.89%; C, 6.14%; H, 17.78%; N, Found: 54.64%; C, 6.38%; H, 17.42%; N.

EXAMPLE 55

Dimethylcarbamic Acid 2-methoxy-4-[2-(4-pyridin-2-yl-piperazin-1-yl)ethyl]phenyl Ester Hydrochloride To a solution of 2-methoxy-4-[2-(4-pyridin-2-yl-piperazin-1-yl)ethyl)phenol (1.0 g) and cesium carbonate (1.0 g) in 25% acetonitrile/dichloromethane was added dimethylcarbamyl chloride (0.7 g), and the reaction mixture was stirred for 18 hrs, under nitrogen. The reaction mixture was diluted with ethyl acetate, and washed with brine, dried over anhydrous sodium sulfate, and concentrated. The residue was flash chromatographed (silica) eluting with 2% methanol/dichloromethane. The appropriate fractions were collected and concentrated. The residue was dissolved in ethyl acetate and ethereal hydrogen chloride was added. The precipitate was collected to give product 0.9 g (73%), mp 192–193° C.

Analysis: Calculated for $C_{21}H_{29}ClN_4O_3$: 59.92%; C, 6.94%; H, 13.31%; N, Found: 59.63%; C, 6.98%; H, 13.20%; N.

EXAMPLE 56

N-(4-Benzyloxy-2-bromo-5-methoxy)benzyl-N'-(pyridin-2-yl)piperazine

Sodium hydride -80% dispersion in oil (0.35 g) was added to a 0° C. solution of (4-benzyloxy-2-bromo-5-methoxy) benzyl bromide and N-(pyridin-2-yl)piperazine (1.4 ml) in dichloromethane (150 ml). The reaction mixture was stirred at ambient temperature for 24 hrs, quenched with water and the layers separated. The organic layer was washed with brine and the aqueous layers were extracted with dichloromethane. The organic extracts were dried over anhydrous sodium sulfate, filtered, and the filtrate was concentrated. The residue was flash column chromatographed (silica gel), eluting with 0–10% ethyl acetate/chloroform. The appropriate fractions were collected to afford 2.2 g (61%) of product. Recrystallization from dichloromethane/heptane gave the analytical sample, mp 130–132° C.

Analysis: Calculated for $C_{24}H_{26}BrN_3O_2$.0.5 $H_2O$: 60.38%; C, 5.70%; H, 8.80%; N, Found: 60.67%; C, 5.54%; H, 8.57%; N.

EXAMPLE 57

1-[[3,4-Dimethoxy)phenyl]methyl]-4-(2-dimethylaminocarbonyloxyphenyl)piperazine Hydrochloride To a suspension of 1-[[3,4-dimethoxy)phenyl]methyl]-4-(2-hydroxyphenyl)piperazine (0.4 g), 1,8-diazabicyclo[5.4.0]undec-7-ene(0.206 g) and acetonitrile (3.5 ml) in an ice bath was added dimethylcarbamyl chloride (0.14 g), with stirring. The reaction mixture was stirred at ice bath temperature for 2.5 hrs, allowed to warm to ambient temperature for 2.5 hrs, cooled again in an ice bath and poured into ice/sodium bicarbonate solution. The layers were separated and extracted with ethyl acetate. The organic extract was washed with water, brine, dried over anhydrous sodium sulfate, filtered, and the filtrate was concentrated. The residue was dissolved in chloroform and flash chromatographed (silica gel), chloroform, 1%, 2%, 3% and 4% methanol/chloroform. The appropriate fractions were collected and concentrated to give 0.26 g (49%) of product, as the free base. The free base was dissolved in chloroform/etherand ethereal hydrogen chloride was added. The precipitate was collected and recrystallized from 2-propanol to give product analytical sample, mp 213–215° C.

Analysis: Calculated for $C_{22}H_{30}ClN_3O_4$: 60.61%; C, 6.94%; H, 9.64%; N, Found: 60.46%; C, 6.93%; H, 9.57%; N,

EXAMPLE 58

N-(2,6-Dibromo-3-hydroxy-4-methoxy)benzyl-N'-(pyridin-2-yl)piperazine

Sodium hydride –80% dispersion in oil (4.0 g) was added to a 0° C. solution of (2.6-dibromo-3-hydroxy-4-methoxy) benzylbromide and N-(pyridin-2-yl)piperazine (5.40 g) in dichloromethane (150 ml). The reaction mixture was stirred at ambient temperature for 72 hrs, quenched with water, the layers separated, and washed with brine. The aqueous layers were extracted with dichloromethane. The organic extracts were dried over anhydrous sodium sulfate, and concentrated. The residue was flash chromatographed (silica gel, 0–20%) eluting with 0–20% ethyl acetate/dichloromethane. The appropriate fractions were collected and concentrated to afford 5.32 g (56%) of product. Recrystallization from dichloromethane/heptane gave the analytical sample, mp 158–160° C.

Analysis: Calculated for $C_{17}H_{19}Br_2N_3O_2$: 44.66%; C, 4.19%; H, 9.19%; N, Found: 44.46%; C, 3.95%; H, 9.01%; N.

EXAMPLE 59

Morpholine-4-carboxylic Acid 2-methoxy-4-[2-(4-pyridin-2-yl-piperazin-1-yl)ethyl]phenyl Ester Hydrochloride To a solution of 2-methoxy-4-[2-(4-pyridin-2-yl-piperazin-1-yl)ethyl]phenol (1.5 g) and cesium carbonate (1.6 g) in 25% acetonitrile/dichloromethane was added 4-morpholinecarbonyl chloride (1.4 g), with stirring, under nitrogen. The reaction mixture was stirred for 18 hrs under nitrogen, diluted with ethyl acetate, and the layers were separated. The organic layer was washed with brine, dried over anhydrous sodium sulfate and concentrated. The residue was flash chromatographed (silica), eluting with 2% methanoludichloromethane. The appropriate fractions were collected and concentrated. The residue was dissolved in ethyl acetate and ethereal hydrochloride was added. The precipitate was collected and recrystallized from ethyl ethanol/ether to give 0.9 g (75%) of product, mp 185–186° C.

Analysis: Calculated for $C_{23}H_{31}ClN_4O_4$: 59.67%; C, 6.75%; H, 12.10%; N, Found: 59.17%; C, 6.87%; H, 11.77%; N.

EXAMPLE 60

4-[[3-Methoxy)-4-(methylaminocarbonyloxy)]phenyl]methyl]-1-(4-fluorophenyl)piperazine Hydrochloride Monohydrate To a solution of 3-methoxy-4-(methylaminocarbonyloxy) benzaldehyde (1.01 g) in 1,2-dichloroethane (19 ml) was added 1-(4-fluorophenyl)piperazine (0.81 g) and sodium triacetoxyborohydride (1.54 g), with stirring. The reaction mixture was stirred at ambient temperature for 3 hrs, poured into ice/saturated sodium carbonate solution (75 ml) and the mixture was extracted with dichloromethane. The organic extracts were washed with water and saturated sodium chloride solution, dried over anhydrous sodium sulfate, filtered, and the filtrate was concentrated. The residue was dissolved in dichloromethane and flash chromatographed (silica gel), eluting with dichloromethane and 1% methanol:dichloromethane. The appropriate fractions were collected and concentrated. The residue was dissolved in chloroform and ethereal hydrogen chloride was added. The precipitate was collected and recrystallized from 2-propanol to give 0.51 g (30%) of product, mp 200–202° C.

Analysis: Calculated for $C_{21}H_{28}Cl_2FN_3O_2$: 56.14%; C, 6.36%; H, 9.82%; N, Found: 56.25%; C, 6.30%; H, 9.66%; N.

EXAMPLE 61

1-(Hydroxyethyl)-4-[[4(-methylaminocarbonyloxy)-3-(methoxy)phenyl)]methyl]piperazine Dihydrochloride To a suspension of 3-(methoxy)-4-(methylaminocarbonyloxy)benzaldehyde (1.0 g) in dichloroethane (16 ml) was added a solution of 2-hydroxyethylpiperazine (0.72 g) in dichloroethane (2 ml) and sodium triacetoxyborohydride (1.40 g), with stirring. The reaction mixture was stirred for 3 hrs at ambient temperature, poured into ice/sodium carbonate solution and extracted with ethyl acetate. The extracts were washed with water, saturated sodium chloride solution, dried over anhydrous sodium sulfate, filtered, and the filtrate was concentrated. The residue was dissolved in chloroform and flash chromatographed (silica gel), eluting with chloroform and 1%, 2%; 5%, 10% and 20% methanol/chloroform. The appropriate fractions were collected and concentrated to give 0.37 g (24%) of product, as the free base. The free base was dissolved in chloroform/ether and ethereal hydrogen chloride was added. The precipitate was collected and recrystallized from ethanol to give product, mp 211–214° C. (dec).

Analysis: Calculated for $C_{16}H_{17}Cl_2N_3O_4$: 48.49%; C, 6.87%; H, 10.60%; N, Found: 48.09%; C, 6.91%; H, 10.27%; N.

EXAMPLE 62

1-[[3-(Methoxy)-4-(methylaminocarbonyloxy) phenyl]methyl]-4-(4-trifluoromethylphenyl) piperazine Hydrochloride To a suspension. of 3-methoxy-4-(methylaminocarbonyloxy)benzaldehyde (1.0 g) in 1,2-dichloroethane (19 ml) was added 1-(trifluoromethylphenylpiperazine) (0.89 ml), and sodium triacetoxyborohydride (1.52 g), with stirring. The reaction mixture was stirred at ambient temperature for 3.5 hrs, poured into ice/saturated sodium carbonate solution (50 ml) and extracted with dichloromethane. The combined organic extracts were washed with water and brine, dried over anhydrous sodium sulfate, filtered, and the filtrate was concentrated. The residue was dissolved in chloroform and flash chromatographed (silica), eluting with chloroform and 1% methanol:chloroform. The appropriate fractions were combined and concentrated. The residue was rechromatographed as above. The appropriate fractions were collected and concentrated to give 0.708 g (32%) of product, free base. The free base was dissolved in diethyl ether and ethereal hydrogen chloride was added. The precipitate was collected and recrystallized from 2-propanol to give product, mp 215–220° C. (dec).

Analysis: Calculated for $C_{21}H_{25}ClF_3N_3O_3$: 54.85%; C, 5.48%; H, 9.14%; N, Found: 54.92%; C, 5.53%; H, 8.98%; N.

EXAMPLE 63

1-[[3-(Methoxy-4-(methylaminocarbonyloxy) phenyl]methyl]-4-(2-chlorophenyl)piperazine Hydrochloride To a suspension of 3-methoxy-4-(methylaminocarbonyloxy)benzaldehyde (1.08 g) in 1,2-dichloroethane (10 ml) was added 1-(2-chlorophenyl) piperazine (1.01 g), in 1,2-dichloroethane (10 ml) and sodium triacetoxyborohydride (1.64 g), with stirring. The reaction mixture was stirred at ambient temperature for 3.5 hrs, poured into ice/saturated sodium carbonate solution (50 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica), eluting with dichloromethane, 1% and 2% methanol:dichloromethane. The appropriate fractions were collected and concentrated. The residue was rechromatographed as above using chloroform instead of dichloromethane. The residue was dissolved in diethyl ether and ethereal hydrogen chloride was added. The precipitate was collected to give 0.66 g (30%) of product, mp 210–213° C. (dec).

Analysis: Calculated for $C_{20}H_{24}ClN_3O_3$: 56.34%; C, 5.91%; H, 9.86%; N, Found: 56.33%; C, 5.97%; H, 10.07%; N.

EXAMPLE 64

N-(2-Bromo-4-hydroxy-5-methoxy)benzyl-N'-(pyridin-2-yl)piperazine

Anhydrous ferric chloride (10.5 g) was added to a solution of N-(4-benzyloxy-2-bromo-5-methoxy)benzyl-N'-(pyridin-2-yl)piperazine(4.0 g) in dichloromethane (100 ml) at ambient temperature. The reaction mixture was heated under reflux for 24 hrs, allowed to cool and filtered. The filter cake was washed with dichloromethane. The filter cake was suspended in 5% sodium hydroxide solution and refiltered. The filtrate was neutralized with hydrochloric acid and extracted with dichloromethane. The organic extracts were dried over anhydrous sodium sulfate and concentrated. The residue was flash chromatographed (silica gel), eluting with dichloromethane 0–5% methanol/dichloromethane. The appropriate fractions were collected and concentrated to afford 1.95 g (60%) of product. Recrystallization from ethyl acetate/heptane gave the analytical sample, mp 167–168° C.

Analysis: Calculated for $C_{17}H_{20}BrN_3O_2$: 53.98%; C, 5.33%; H, 11.11%; N, Found: 53.96%; C, 5.33%; H, 10.79%; N.

EXAMPLE 65

N-(2,6-Dibromo-3-[dimetliylcilrbanioyloxy]-4-inetlioxy)benzyl-N'-(pyridin-2-yl)-piperazine Cesium carbonate (1.10 g) was added to a solution of N-(2,6-dibromo-3-hydroxy-4-methoxy)benzyl-N'-(pyridin-2-yl)-piperazine (1.00 g) in dichloromethane (20 ml) at ambient temperature. The mixture was stirred for 30 mins at ambient temperature, dimethylcarbamoyl chloride (1.00 ml) was added and the reaction mixture was stirred for 24 hrs at ambient temperature. The reaction mixture was quenched with water, diluted with brine, and extracted with dichloromethane. The organic extracts were dried over anhydrous sodium sulfate, filtered, and the filtrate was concentrated. The residue was flash chromatographed (silica gel), 0–1% methanol/ethyl acetate. The appropriate fractions were collected and concentrated to afford 1.31 g (95%) of product. Recrystallization from dichloromethane petroleum ether afforded the analytical sample, mp 147–148° C.

Analysis: Calculated for $C_{21}H_{24}Br_2N_4O_3$: 45.47%; C, 4.58%; H, 10.61%; N, Found: 45.47%; C, 4.57%; H, 10.34%; N.

EXAMPLE 66

N-(2-Bromo-5-[dimetliylcarbamoyloxy]-4-methoxy) benzyl-N'-(pyridin-2-yl)-piperazine Cesium carbonate (0.75 g) was added to a solution of N-(2-bromo-5-hydroxy-4-methoxy)benzyl-N'-(pyridin-2-yl)-piperazine (0.58 g) in dichloromethane (15 ml) at ambient temperature. The mixture was stirred for 30 min at ambient temperature and dimethylcarbamoyl chloride (0.50 ml) was added. The reaction mixture was stirred for 24 hrs at ambient temperature, quenched with water, diluted with brine, and extracted with dichloromethane. The organic extracts were dried over anhydrous sodium sulfate, filtered, and the filtrate was concentrated. The residue was flash chromatographed (silica gel), eluting with 0–5% methanol:ethyl acetate. The appropriate fractions were collected and concentrated to afford 0.64 g (93%) of product. Recrystallization from dichloromethane/petroleum ether gave the analytical sample, mp 167–168° C.

Analysis: Calculated for $C_{20}H_{25}BrN_4O_3$: 53.46%; C, 5.61%; H, 12.47%; N, Found: 53.41%; C, 5.56%; H, 12.18%; N.

EXAMPLE 67

N-(2-Bromo-4-[dimethylcarbamoyloxy]-5-methoxy)benzyl-N'-(pyridin-2-yl)-piperazine Cesium carbonate (0.66 g) was added to a solution of N-(2-bromo-4-hydroxy-5-methoxy)benzyl-N'-(pyridin-2-yl)-piperazine (0.50 g) in dichloromethane (15 ml) at ambient temperature. The mixture was stirred for 30 mins at ambient temperature and dimethylcarbamoyl chloride (0.60 ml) was added. The reaction mixture was stirred for 24 hrs at ambient temperature, quenched with water, diluted with brine, and extracted with dichloromethane. The organic extracts were dried over anhydrous sodium sulfate, filtered, and the filtrate was concentrated. The residue was flash chromatographed (silica gel), eluting with 0–2% methanol/ethyl acetate. The appropriate fractions were collected and concentrated to afford 0.53 g (90%) of product. Recrystallization from dichloromethane/petroleum ether gave the analytical sample, mp 145–147° C.

Analysis: Calculated for $C_{20}H_{25}BrN_4O_3$: 53.46%; C, 5.61%; H, 12.47%; N, Found: 53.32%; C, 5.61%; H, 12.26%; N.

EXAMPLE 68

N-(4-Benzyloxy-2-chloro-5-methoxy)benzyl-N'-(pyridin-2-yl)-piperazine

Sodium hydride –80% dispersion in oil (1.25 g) was added to a solution of 4-benzyloxy-2-chloro-5-methoxybenzyl chloride (3.85 g) and N-(pyridin-2-yl)-piperazine (2.60 g) in dichloromethane (125 ml) at ambient temperature. The reaction mixture was stirred at ambient temperature for 24 hrs, quenched with water, diluted with brine, and extracted with dichloromethane. The organic extracts were dried over anhydrous sodium sulfate, filtered, and the filtrate was concentrated. The residue was flash chromatographed (silica gel), 0–1% methanol/ethyl acetate. The appropriate fractions were collected and evaporated to afford 3.26 (g) (59%) of product, mp 120–122° C.

Analysis: Calculated for $C_{24}H_{26}ClN_3O_2$: 68.00%; C, 6.18%; H, 9.91%; N, Found: 67.85%; C, 6.17%; H, 9.65%; N.

EXAMPLE 69

1-[[3-(Methoxy)-4-(methylaminocarbonyloxy)pheny]methyl-4-(2-methoxyphenyl)-piperazine Hydrochloride Monohydrate To a suspension of 3-methoxy-4-(methylaminocarbonyloxy)benzaldehyde (5.48 g) in 1,2-dichloroethane (95 ml) was added 1-(2-methoxyphenyl) piperazine (5.03 g) in 1,2-dichloroethane (8.0 ml) and sodium triacetoxyborohydride (8.33 g), with stirring. The reaction mixture was stirred at ambient temperature for 3 hrs, poured into ice/saturated sodium carbonate solution (200 ml) and extracted with dichloromethane. The combined organic extracts were washed with water, dried over anhydrous sodium sulfate, filtered, and the filtrate was concentrated. The residue was dissolved in dichloromethane and high performance liquid chromatographed, eluting with 2% methanol:dichloromethane. The appropriate fractions were collected and concentrated to give 6.62 g (66%) of product, free base. The free base was dissolved in ether and ethereal hydrogen chloride was added. The precipitate was collected to give the analytical sample, mp 138–155° C.

Analysis: Calculated for $C_{21}H_{30}ClN_3O_5 \cdot HCl \cdot H_2O$: 57.33%; C, 6.87%; H, 9.55%; N, Found: 57.57%; C, 6.76%; H, 9.24%; N.

EXAMPLE 70

1-[[3-Methoxy)-4-(methylaminocarbonyloxy)phenyl]methyl]-4-(2-hydroxyphenyl)-piperazine Dihydrochloride To a suspension of 3-(methoxy)-4-(methylaminocarbonyloxy) benzaldehyde (1.0 g), 2-(hydroxyphenyl)piperazine (0.98 g) and dichloroethane (16 ml) was added sodium triacetoxyborohydride (0.32 g), with stirring. The reaction mixture was stirred at ambient temperature for 2 hrs, poured into ice/sodium carbonate solution and extracted with ethyl acetate. The extracts were washed with water, brine, dried over anhydrous sodium sulfate, filtered, and the filtrate was concentrated. The residue 3vas dissolved in chloroform and flash chromatographed (silica gel), eluting with chloroform, 1%, 2% and 5% methanol/chloroform. The appropriate fractions were combined and concentrated. The residue was dissolved in chloroform, and was high performance liquid chromatographed on silica gel, eluting with chloroform, 1% methanol and 2% methanol/chloroform/trace. ammonium hydroxide to provide 1.44 g (81.2%) of product, as the free base. The appropriate fractions were collected and concentrated. The free base was dissolved in chloroform ether and ethereal hydrogen chloride was added. The precipitate was collected and recrystallized from ethanol to give product, mp 152–154° C.

Analysis: Calculated for $C_{20}H_{27}Cl_2N_3O_4$: 54.06%; C, 6.12%; H, 9.46%; N, Found: 53.78%; C, 6.43%; H, 9.16%; N.

EXAMPLE 71

1-[[3-(Methoxy)-4-(methylaminocarbonyloxy)phenyl]methyl]-4-(2-fluorophenyl)-piperazine Hydrochloride Monohydrate To a solution of 3-methoxy-4-(methylaminocarbonyloxy)benzaldehyde (1.00 g) in 1,2-dichloroethane (19 ml) was added 1-(2-fluorophenyl)piperazine (0.55 ml), and sodium triacetoxyborohydride (1.53 g), with stirring. The reaction mixture was stirred overnight at ambient temperature, poured into ice/saturated sodium carbonate solution (75 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica gel) eluting with dichloromethane and 1% methanol:dichloromethane. The appropriate fractions were collected and concentrated to give 0.44 g (24%) of product, free base. The free base was dissolved in ether and ethereal hydrogen chloride was added. The precipitate was collected to afford product, mp 204–208° C. (dec).

Analysis: Calculated for $C_{20}H_{27}ClFN_3O_4$: 56.14%; C, 6.36%; H, 9.82%; N, Found: 56.48%; C, 6.15%; H, 9.69%; N.

EXAMPLE 72

1-[[3-(Methoxy)-4-(methylaminocarbonyloxy) phenyl]methyl]-4-(2-methylphenyl)-piperazine Hydrochloride Monohydrate To a solution of 3-methoxy-4-(methylaminocarbonyloxy) benzaldehyde (1.00 g) in 1,2-dichloroethane (19 ml) was added 1-(2-fluorophenyl)piperazine (0.55 ml) and sodium triacetoxyborohydride (1.54 g), with stirring. The reaction mixture was stirred at ambient temperature for 3 hrs, poured into ice/saturated sodium carbonate solution (75 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica gel) eluting with dichloromethane, followed by 1% methanol:dichloromethane. The appropriate fractions were collected and concentrated to give 0.64 g (36%) product, free base. The free base was dissolved in diethyl ether and ethereal hydrogen chloride was added. The precipitate was collected to give product, mp 185–190° C.

Analysis: Calculated for $C_{21}H_{30}ClN_3O_5$: 59.50%; C, 7.13%; H, 9.91%; N, Found: 59.60%; C, 6.97%; H, 10.00%; N.

EXAMPLE 73

1-[1-(3-Fluoro-4-methoxyphenyl)ethyl]-4-pyridin-2-yl-piperazine Hydrochloride

To a stirred solution of 2-fluoro-4-methoxyacetophenone (4.0 g) and 1-(2-pyridyl)piperazine (3.6 ml) in acetonitrile (50 ml) was added titanium (IV) isopropoxide (11 ml) under nitrogen, with stirring. The reaction mixture was stirred for 1 hr. Sodium cyanoborohydride (1.0 g) with absolute ethanol (50 ml) were added. After 24 hrs, the reaction mixture was diluted with ethyl acetate and quenched with a saturated solution of sodium sulfate, filtered, dried over anhydrous sodium sulfate, filtered, and the filtrate was concentrated. The residue was flash chromatographed (silica gel), eluting with 2% acetone/2% methanol/dichloromethane. The appropriate fractions were collected and concentrated. The residue was dissolved in ether and ethereal hydrogen chloride was added. The precipitate was collected and recrystallized from acetonitrile/propanol to afford product, mp 231–232° C.

Analysis: Calculated for $C_{18}H_{23}ClN_3O$: 61.45%; C, 6.59%; H, 11.94%; N, Found: 61.11%; C, 6.64%; H, 11.86%; N.

EXAMPLE 74

1-[1-(4-N,N-Dimethylcarbamoyloxy-3-fuorophenyl) ethyl]-4-pyridin-2-yl-piperazine To a solution of 1-[1-(3-fluoro-4-hydroxyphenyl)ethyl]-4-pyridin-2-yl-piperazine(0.4 g) and cesium carbonate (0.4 g) in 25% acetonitrile/dichloromethanewas added dimethylcarbamyl chloride (0.3 g), under nitrogen, with stirring. The reaction mixture stirred for 28 hrs, diluted with ethyl acetate, washed with water, dried over anhydrous so dium sulfate, filtered and the filtrate was concentrated. The residue was flash chromatographed (silica gel), eluting with 2% methanol/dichloromethane. The appropriate fractions were collected and concentrated to afford 0.30 g (85%) of product, mp 116 to 117° C.

Analysis: Calculated for $C_{20}H_{25}FN_4O_2$: 64.50%; C, 6.77%; H, 15.04%; N, Found: 64.27%; C, 6.75%; H, 14.49%; N.

EXAMPLE 75

2-Fluoro-4-[1-(4-pyridin-2-yl-piperazin-1-yl)ethyl] phenolhydrochloride Hemihydrate A solution of 1-[1-(3-fluoro-4-methoxyphenyl)ethyl]-4-pyridinyl-2-yl-piperazine (1.1 g) in 48% hydrobromic acid (15 ml) was heated to 1 00C for 4 hrs, under nitrogen. The reaction mixture was diluted with ethyl acetate, neutralized with saturated sodium carbonate solution, dried over anhydrous sodium sulfate, filtered, and the filtrate was concentrated. The residue was flash chromatographed (silica gel), eluting with 4% methanol/dichloromethane. The appropriate fractions were collected and concentrated to provide 0.10 g (25%) of product, as the free base. The free base was dissolved in ether and acidified with ethereal hydrogen chloride to afford product, mp 182–183° C.

Analysis: Calculated for $C_{17}H_{20}FN_3O.HCl.1/2\ H_2O$: 58.87%; C, 6.39%; H, 12.12%; N, Found: 58.46%; C, 6.39%; H, 11.76%; N.

EXAMPLE 76

1-[[3-Methoxy)-4-(methylaminocarbonyloxy) phenyl]methyl]-4-(2,4-difluorophenyl)piperazine Hydrochloride To a suspension of 3-(methoxy)-4-(methylaminocarbonyloxy)benzaldehyde (1.26 g), (2,4-difluorophenyl)piperazine (1.42 g) and 1,2-dichloroethane (22 ml), was added sodium triacetoxyborohydride (1.67 g), with stirring. The reaction mixture was stirred for 2 hrs at ambient temperature, poured into ice/sodium carbonate solution and extracted with ethyl acetate. The extracts were washed with water and brine, dried over anhydrous sodium sulfate, filtered, and the filtrate was concentrated. The residue was dissolved in dichloromethane and flash chromatographed (silica gel), eluting with dichloromethane, 1%, 2% and 5% methanol/dichloromethane. The appropriate fractions were combined and concentrated to provide 1.96 g (83%) of product, as the free base. The free base was dissolved in chloroform and flash chromatographed on silica gel, eluting with chloroform, 1%, 2% and 3% methanol/chloroform to provide 1.96 g (83%) of product, as the free base. The appropriate fractions were collected and concentrated. The reside was dissolved in chloroform/ether. Ethereal hydrogen chloride was added. The precipitate was collected and recrystallized from ethanol to provide product, mp 192–195° C.

Analysis: Calculated for $C_{20}H_{24}ClF_2N_3O_3$: 56.14%; C, 5.65%; H, 9.82%; N, Found: 55.88%; C, 5.71%; H, 9.62%; N.

EXAMPLE 77

1-[1-(4-Hydroxy-3-methoxyphenyl)ethyl]-4-pyridin-2-yl-piperazine Hemihydrate

A solution of 1-[1-4-acetoxy-3-methoxyphenyl)ethyl]-4-pyridinyl-2-yl-piperazine(2.0 g) in 50% sodium hydroxide solution (5 ml) and 50% ethanol (40 ml) was heated to 50° C. for 4 hrs, under nitrogen. The reaction mixture was diluted with ethyl acetate (150 ml), neutralized with 10% hydrochloric acid, dried over anhydrous sodium sulfate, filtered, and the filtrate was concentrated. The residue was flash chromatographed (silica gel), eluting with 4% methanol/dichloromethane. The appropriate fractions were collected and concentrated to provide 0.5 g (40%) of product, mp 45–46° C.

Analysis: Calculated for $C_{18}H_{23}N_3O_2.1/2\ H_2O$: 67.06%; C, 7.50%; H, 13.03%; N, Found: 67.68%; C, 7.52%; H, 12.73%; N.

EXAMPLE 78

1-[1-(4-N,N-Dimethylcarbamoyloxy-3-methoxyphenyl)ethyl]-4-pyridin-2-yl-piperazine Dihydrochloride To a solution of 1-[1-(4-hydroxy-3-methoxyphenyl)ethyl]-4-pyridin-2-yl-piperazine(0.6 g) and cesium carbonate (0.6 g) in 25% acetonitrile/dichloromethane (50 ml) was added dimethylcarbamyl chloride (0.4 g) under nitrogen, with stirring. The reaction stirred for 18 hrs, was diluted with ethyl acetate, washed with water, dried over anhydrous sodium sulfate, filtered, and the filtrate was concentrated. The residue was flash chromatographed (silica gel), eluting with 2% methanol/dichloromethane. The appropriate fractions were collected and concentrated to afford 0.2 g (15%) of product, mp 155–156° C.

Analysis: Calculated for $C_{21}H_{30}ClN_4O_3$: 55.14%; C, 6.61%; H, 12.25%; N, Found: 55.08%; C, 6.89%; H, 12.05%; N.

EXAMPLE 79

1-[[3-Methoxy)-4-(methylaminocarbonyloxy)phenyl]methyl)-4-(2-cyanophenyl)-piperazine Hydrochloride To a suspension of 3-(methoxy)-4-(methylaminocarbonyloxy)benzaldehyde (0.93 g), (cyanophenyl)piperazine (0.98 g) and dichloroethane (16 ml) was added sodium triacetoxyborohydride (1.32 g), with stirring. The reaction mixture was stirred for 2 hrs at ambient temperature, poured into ice/sodium carbonate solution and extracted with ethyl acetate. The extracts were washed with water, brine, dried over anhydrous sodium sulfate, filtered, and the filtrate was concentrated. The residue was dissolved in chloroform and flash chromatographed (silica gel), eluting with chloroform, 1% and 2% methanol/chloroform. The appropriate fractions were collected and concentrated. The residue was rechromatographed on silica gel eluting with chloroform and 1%, 2% methanol/chloroform. The appropriate fractions were collected and concentrated to provide 0.98 g (58%) of product, as the free base. The free base was dissolved in chloroform/ether. Ethereal hydrogen chloride was added. The precipitate was collected and recrystallized from ethanol to provide product, mp 218–222° C. (dec).

Analysis: Calculated for $C_{21}H_{25}ClN_4O_3$: 60.50%; C, 6.04%; H, 13.44%; N, Found: 60.30%; C, 6.07%; H, 13.28%; N.

EXAMPLE 80

1-[[3-(Methoxy)-4-(methylaminocarbonyloxy)phenyl]methyl]-4-(phenyl)piperazine Hydrochloride To a solution of 3-methoxy-4-(methylaminocarbonyloxy)benzaldehyde (1.0 g) in 1,2-dichloroethane (20 ml) was added 1-phenylpiperazine, (0.73 ml) and sodium triacetoxyborohydride (1.52 g). The reaction mixture was stirred at ambient temperature overnight, poured into saturated sodium carbonate solution (75 ml) and extracted with dichloromethane. The combined organic extracts were washed with water and brine, dried over anhydrous sodium sulfate, filtered, and the filtrate was concentrated. The residue was dissolved in dichloromnethane and flash chromatographed (silica gel), eluting with dichloromethane and 1% methanol:dichloromethane . The appropriate fractions were collected and concentrated to give 1.24 g (73%) of product, as the free base. Ethereal hydrogenchloride was added to the free base. The solid was collected to give product, mp 210–215° C. (dec).

Analysis: Calculated for $C_{20}H_{26}ClN_3O_3$: 61.30%; C, 6.69%; H, 10.72%; N, Found: 60.91%; C, 6.65%; H, 10.30%; N.

EXAMPLE 81

1-[1-(4-Hydroxy-3-methoxyphenyl)ethyl]-4-(2-methoxyphenyl)piperazine Dihydrochioride Hemihydrate A solution of 1-[1-(4-acetoxy-3-methoxyphenyl)ethyl]-4-(2-methoxyphenyl)piperazine(2.7 g) in 50% sodium hydroxide solution (5 ml) and 50% ethanol (40 ml) was heated to 50° C. for 4 hrs, under nitrogen. The reaction mixture was diluted with ethyl acetate (150 ml), neutralized with 110% hydrochloric acid, dried over anhydrous sodium sulfate, filtered, and the filtrate was concentrated. The residue was flash chromaographed (silica gel), 2% acetone, 2% methanol/dichloromethane. The appropriate fractions were collected and concentrated. The residue was dissolved in ethyl acetate (150 ml) and e thereal hydrogen chloride was added. The precipitate was collected to provide 0.5 g (25%) of product, mp 130–13 1° C.

Analysis: Calculated for $C_{20}H_{26}N_2O_3.2HCl.1/2\ H_2O$: 56.61%; C, 6.89%; H, 6.60%; N, Found: 56.12%; C, 6.75%; H, 6.29%; N.

EXAMPLE 82

1-[1-(4-N,N-Dimethylcarbamoyloxy-3-methoxyphenyl)ethyl]-4-(2-methoxyphenyl)piperazine Hemihydrate To a solution of 1-[1-(4-hydroxy-3-methoxyphenyl)ethyl]-4-(2-methoxyphenylpiperazine (0.3 g) and cesium carbonate (0.3 g) in 25% acetonitrile/dichloromethane(15 ml) was added dimethylcarbamyl chloride (0.2 g), under nitrogen. The reaction mixture stirred for 18 hrs, diluted with ethyl acetate (150 ml), washed with water, dried over anhydrous sodium sulfate, filtered, and the filtrate was concentrated. The residue was flash chromatographed (silica gel), eluting with 2% methanol/dichloromethane. The appropriate fractions were collected and concentrated to give 70 mg (20%) of product, mp 55–56° C.

Analysis: Calculated for $C_{23}H_{31}N_3O_4.1/2\ H_2O$: 65.38%; C, 7.63%; H, 9.94%; N, Found: 65.41%; C, 7.44%; H, 9.44%; N.

EXAMPLE 83

1-[1-4-Hydroxy-3-methoxyphenyl)ethyl]-4-(2-fluorophenyl)piperazinedihydrochloride Hemihydrate A solution of 1-[1-(4-acetoxy-3-methoxyphenyl)ethyl]-4-(2-flutorophenyl)piperazine(2.5 g) in 50% sodium hydroxide solution (5 ml) and 50% ethanol (40 ml) was heated to 50° C. for 4 hrs, under nitrogen. The reaction mixture was diluted with ethyl acetate (150 ml), neutralized with 10% hydrochloric acid, dried over anhydrous sodium sulfate, filtered, and the filtrate was concentrated. The residue was flash chromatographed (silica gel), eluting with 2% acetone/ 2% methanol/dichloromethane. The appropriate fractions were collected and concentrated. The residue was dissolved in ethyl acetate and ethereal hydrogen chloride was added. The precipitate was collected to give 0.5 g (45%) of product, mp 121–122° C.

Analysis: Calculated for $C_{19}H_{23}N_2O_2 \cdot 2$ HCl$\cdot 1/2$ $H_2O$: 60.71%; C, 6.70%; H, 7.45%; N, Found: 60.99%; C, 6.63%; H, 7.41%; N.

EXAMPLE 84

N-2-chloro-4-hydroxy-5-methoxybenzyl-N'-pyridin-2-yl Piperazine

A solution of N-(4-benzyloxy-2-chloro-5-methoxy) benzyl-N'-pyridin-2-ylpiperazine (3.11 g) in dichlormethane (25 ml) was added to a suspension of ferric chloride (6.40 g) in dichloromethane (75 ml) at ambient temperature. The reaction mixture was heated under reflux for 3 hrs and allowed to cool to ambient temperature and filtered. The filter cake was washed with ethyl acetate and suspended in 10% sodium hydroxide (500 ml) and refiltered. The filtrate was neutralized with hydrochloric acid and extracted with ethyl acetate. The organic extracts were dried over anhydrous sodium sulfate, filtered, and the filtrate was concentrated. The residue was flash chromatographed (silica gel), eluting with 1% methanol/ethyl acetate. The appropriate fractions were collected and concentrated to afford 0.58 g (24%) of product. Recrystallization from ethyl acetate/heptane gave the analytical sample, mp 170–172° C.

Analysis: Calculated for $C_{17}H_{20}ClN_3O_2$: 61.17%; C, 6.04%; H, 12.59%; N, Found: 61.24%; C, 6.04%; H, 12.28%; N.

EXAMPLE 85

N-2,6-dibromo-3-hydroxy-4-methoxybenzyl-N'-2-methoxyphenyl Piperazine

Sodium hydride –80% dispersion in oil (1.0 g) was added to a solution of (2.6-dibromo-3-hydroxy-4-methoxy)benzyl bromide (3.05 g) and N-2-methoxyphenyl piperazine (1.85 g) in dichloromethane (75 ml) at ambient temperature. The reaction mixture was stirred for 24 hrs at ambient temperature, quenched with water, diluted with ethyl acetate, and washed with brine. The organic extract was dried over anhydrous sodium sulfate, filtered, and the filtrate was concentrated to give 5.22 g of product. The residue was flash chromatographed (silica gel), eluting with 10–80% ethyl acetate/heptane. The appropriate fractions were collected and concentrated to afford 3.71 g (94%) of product. Recrystallization from dichloromethane/petroleum ether gave the analytical sample, mp 178–180° C.

Analysis: Calculated for $C_{19}H_{22}Br_2N_2O_3$: 46.94%; C, 4.56%; H, 5.76%; N, Found: 46.89%; C, 4.37%; H, 5.67%; N.

EXAMPLE 86

N-2-bromo-5-hydroxy-4-methoxybenzyl-N'-2-methoxyphenyl Piperazine

Sodium hydride –80% dispersion in oil (0.40 g) was slowly added over 10 mins to a solution of 2-bromo-5-hydroxy-4-methoxybenzyl bromide (1.0 g) and 2-methoxyphenyl piperazine (0.87 g) in dichloromethane (30 ml), at ambient temperature. The reaction mixture was stirred, under nitrogen, for 24 hrs at ambient temperature, quenched with water, diluted with brine, and extracted with dichloromethane. The organic extracts were dried over anhydrous sodium sulfate, filtered, and the filtrate was concentrated. The residue was flash chromatographed (silica gel), 20–50% ethyl acetate/heptane. The appropriate fractions were collected and concentrated to afford 1.01 g (73% ) of product. Recrystallization from dichloromethane/heptane afforded the analytical sample, mp 177–179° C.

Analysis: Calculated for $C_{19}H_{23}BrN_2O_3 \cdot 1/2$ $H_2O$: 54.82%; C, 5.81%; H, 6.73%; N, Found: 55.23%; C, 5.50%; H, 6.60%; N.

EXAMPLE 87

1-[[3-Methoxy)-4-(methylaminocarbonyloxy) phenyl]methyl]-4-(2-furoyl)-piperazine Hydrochloride To a suspension of 3-(methoxy)-4-(methylaminocarbonyloxy)benzaldehyde (1.5 g), 1-(2-furoyl)piperazine (1.54 g) and dichloroethane (26 ml) was added sodium triacetoxyborohydride (2.0 g), with stirring. The reaction mixture was stirred for 3.5 hrs at ambient temperature, poured into ice/sodium carbonate solution and extracted with ethyl acetate. The extracts were washed with water, brine, dried over anhydrous sodium sulfate, filtered, and the filtrate was concentrated. The residue was dissolved in chloroform and high performance liquid chromatographedon silica gel, eluting with chloroform, 1%, 2% and 3% methanol/chloroform. The appropriate fractions were collected and concentrated. The residue was dissolved in chloroform and rechromatographed op silica gel, eluting with the same solvent system as before. The appropriate fractions were collected and concentrated to give 2.03 g (76%) of product, as the free base. The free base was dissolved in chloroform/ether and ethereal hydrogen chloride was added. The precipitate was collected and recrystallized from ethanol to give the analytical sample, mp 224–229° C. (dec).

Analysis: Calculated for $C_{19}H_{24}ClN_3O_4$: 55.68%; C, 5.90%; H, 10.25%; N, Found: 55.22%; C, 5.90%; H, 10.38%; N.

EXAMPLE 88

1-[1-(4-N,N-Dimethylcarbamoyloxy-3-methoxyphenyl)ethyl]-4-(2-fluorophenyl)piperazine Hydrochloride Hydrate To a solution of 1-[1-(4-hydroxy-3-methoxyphenyl) ethyl]-4-(2-fluorophenyl)piperazine(0.5 g) and cesium carbonate (0.5 g) in 25% acetonitrile/dichloromethane (30 ml) was added dimethylcarbamyl chloride (0.3 g), under nitrogen, with stirring. The reaction mixture stirred for 18 hrs, diluted with ethyl acetate, washed with brine, dried over anhydrous sodium sulfate, filtered, and the filtrate was concentrated. The residue was flash chromatographed (silica gel), eluting with 2% methanol/dichloromethane. The appropriate fractions were collected and concentrated. The residue was dissolved in ethyl acetate and ethereal hydrogen chloride was added. The precipitate was collected to give 0.3 g (55%) of product, mp 142–143° C.

Analysis: Calculated for $C_{22}H_{31}ClFN_3O_4$: 57.95%; C, 6.85%; H, 9.22%; N, Found: 57.66%; C, 6.49%; H, 9.05%; N.

EXAMPLE 89

1-[1-(4-Hydroxy-3-methoxyphenyl)ethyl]-4-(2-methoxyphenyl)piperazine Hemihydrate A solution of 1-[1-(4-acetoxy-3-methoxyphenyl)ethyl]-4-(2-ethoxyphenyl)piperazine (2.5 g) in 50% sodium hydroxide (5 ml) and ethanol (40 ml) was heated to 50° C. for 4 hrs, under nitrogen. The reaction mixture was diluted with ethyl acetate (150 ml), neutralized with 10% hydrochloric acid, dried over anhydrous sodium sulfate, filtered, and the filtrate was concentrated. The residue was flash chromatographed (silica gel), eluting with 2% acetone 2% methanol/dichloromethane. The appropriate fractions were collected and concentrated to provide 1.0 g (45%) of product, mp 58–59° C.

Analysis: Calculated for $C_{21}H_{21}N_2O_3 \cdot 1/2\ H_2O$: 69.02%; C, 8.00%; H, 7.66%; N, Found: 69.52%; C, 7.97%; H, 7.51%; N.

EXAMPLE 90

1-[1-(3-Methoxy-4-N-methylcarbamoyloxyphenyl)ethyl]-4-(2-fluorophenyl)piperazine Quarterhydrate To a solution of 1-[1-(4-hydroxy-3-methoxyphenyl)ethyl]-4-(2-fluorophenyl)piperazine(0.5 g) and copper (I) chloride (catalytic amount) in 25% acetonitrile/dichloromethane (30 ml) was added methyl isocyanate (0.09 g) in 25% acetonitrile/dichloromethane (30 ml), with stirring. The reaction mixture stirred for 4 hrs, diluted with ethyl acetate, washed with brine, dried over anhydrous sodium sulfate, filtered, and the filtrate was concentrated. The residue was flash chromatographed (silica gel), eluting with 1% methanol/dichloromethane. The appropriate fractions were collected and concentrated to afford 0.25 g (40%) of product, mp 61–62° C.

Analysis: Calculated for $C_{21}H_{26}FN_3O_3 \cdot 1/4\ H_2O$: 64.35%; C, 6.81%; H, 10.72%; N, Found: 64.50%; C, 6.94%; H, 10.53%; N.

EXAMPLE 91

1-[[3-(Methoxy)-4-(methylaminocarbonyloxy)phenyl]methyl]-4-(4-nitrophenyl)piperazine To a solution of 3-methoxy-4-(methylaminocarbonyloxy)benzaldehyde (1.01 g) in 1,2-dichloroethane (19.0 ml) was added 1-(4-nitrophenyl)piperazine (1.0 g), and sodium triacetoxyborohydride (1.54 g), with stirring. The reaction mixture was stirred for 3 hrs at ambient temperature, poured into ice/saturated sodium carbonate solution (100 ml) and extracted with dichloromethane. The combined organic extracts were washed with water and brine, dried over sodium sulfate, filtered, and the filtrate was concentrated. The residue was flash chromatographed (silica gel), eluting with dichloromethane, followed by 1% methanol:dichloromethane. The appropriate fractions were collected and concentrated to give 1.66 g (86%) of product. Recrystallization from ethyl acetate gave the analytical sample, mp 155–157° C.

Analysis: Calculated for $C_{20}H_{24}N_4O_5$: 59.99%; C, 6.04%; H, 13.99%; N, Found: 59.81%; C, 6.01%; H, 13.94%; N.

EXAMPLE 92

1-[3,4 Dimethoxyphenyl]methyl]-4-(2-hydroxyphenyl)-piperazine Hydrochloride

To a suspension of 3,4-dimethoxybenzaldehyde (2.0 g), 1-(2-hydroxyphenyl)piperazine (2.03 g) in dichloroethane (35 ml), was added sodium triacetoxyborohydride (2.67 g), with stirring. The reaction mixture was stirred for 2,5 hrs at ambient temperature, poured into ice/sodium carbonate solution and extracted with ethyl acetate. The extract was washed with water, brine, dried over anhydrous sodium sulfate, filtered, and the filtrate was concentrated. The residue was dissolved in dichloromethane and flash chromatographed (silica gel), eluting with dichloromethane, 1% and 2% methanol/dichloromethane. The appropriate fractions were combined and concentrated. The residue was dissolved in dichloromethane and again flash chromatographed (silica gel), eluting with dichloromethane and 1% methanol/dichloromethane. The appropriate fractions were collected and concentrated to provide 1.03 g (32.8%) of product, as the free base. The free base was dissolved in chloroform/ether. Ethereal hydrogen chloride was added. The precipitate was collected and recrystallized from ethanol to provide product, mp 245–249° C.

Analysis: Calculated for $C_{19}H_{25}ClN_2O_3$: 62.55%; C, 6.91%; H, 7.68%; N, Found: 62.65% 6.82%; H, 7.70%; N.

EXAMPLE 93

1-[[3-(Methoxy)-4-(dimethylaminocarbonyloxy)phenyl]methyl]-4-(2-chlorophenyl)piperazine Hydrochloride To a solution of 3-methoxy-4-(dimethaminocarbonyloxy)benzaldehyde (1.0 g) in 1,2-dichloroethane (9.0 ml), was added 1-(2-chlorophenyl)piperazine (0.88 g) dissolved in 1,2-dichloroethane (9.0 ml) and sodium triacetoxyborohydride (1.42 g), with stirring. The reaction mixture was stirred for 4 hrs at ambient temperature, poured into ice/saturated sodium carbonate solution (50 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica), eluting with dichloromethane/0.1%, 0.5%, and 1% methanol:dichloromethane. The appropriate fractions were collected and concentrated to give 1.37 g (75%) of product. Recrystallizationfrom 2-propanol gave the analytical sample, mp 190–193° C.

Analysis: Calculated for $C_{21}H_{26}ClN_3O_3$: 57.28%; C, 6.18%; H, 9.54%; N, Found: 57.10%; C, 6.04%; H, 9.48%; N.

EXAMPLE 94

1-[1-(4-N,N-Dimethylcarbamoyloxy-3-methoxyphenyl)ethyl]-4-(2-ethoxyphenyl)piperazine Dihydrochloride Hemihydrate To a solution of 1-[4-hydroxy-3-methoxyphenyl)ethyl]-4-(2-ethoxyphenyl)piperazine(0.42 g) and cesium carbonate (0.39 g) in 25% acetonitrile/dichloromethane (30 ml), was added dimethylcarbamyl chloride (0.26 g), under nitrogen, with stirring. The reaction mixture stirred for 18 hrs, diluted with ethyl acetate, washed with brine, dried over anhydrous sodium sulfate, filtered, and the filtrate was concentrated. The residue was flash chromatographed (silica gel), eluting with 1% acetone/1% methanol/dichloromethane. The appropriate fractions were collected and concentrated. The residue was dissolved in ethyl acetate and ethereal hydrogen chloride was added. The precipitate was collected to afford 0.2 g (60%) of product, mp 1 18–119° C.

Analysis: Calculated for $C_{24}H_{33}N_3O_4 \cdot 2HCl \cdot 1/2H_2O$: 56.58%; C, 7.12%; H, 8.25%; N, Found: 56.60%; C, 7.32%; H, 7.76%; N.

EXAMPLE 95

1-[1-(3-Methoxy-4-N-methylcarbamoyloxyphenyl) ethyl]-4-(2-ethoxyphenyl)piperazine To a solution of 1-[1-(4-hydroxy-3-methoxyphenyl) ethyl]-4-(2-ethoxyphenyl)piperazine(0.6 g) and copper (I) chloride (catalytic amount) in ethyl acetate (20 ml) was added methyl isocyanate (0.1 g), under nitrogen, with stirring. The reaction mixture stirred for 3 hrs, was diluted with ethyl acetate, washed with brine, dried over anhydrous sodium sulfate, filtered, and the filtrate was concentrated. The residue was flash chromatographed (silica gel), eluting with 1% methanol/dichloromethane. The appropriate fractions were collected and concentrated to afford 0.2 g (30%) of product, mp 64–65° C.

Analysis: Calculated for $C_{23}H_{31}N_3O_4$: 66.81%; C, 7.56%; H, 10.16%; N, Found: 66.49%; C, 7.50%; H, 9.75%; N.

EXAMPLE 96

1-[[3,4-Dimethoxy)phenyl]methyl]-4-(2-methylaminocarbonyloxyphenyl)piperazine Dihydrochloride To a suspension of 1-[[3,4-dimethoxy)phenyl]methyl]-4-(2-hydroxyphenyl)piperazine(0.3 g) and milled potassium carbonate (0.18 g) was added dry tetrahydrofuran (7 ml), under nitrogen, with stirring. The mixture was cooled in an ice bath and methyl isocyanate (59.8 mg) was added. The reaction mixture was stirred at ice bath temperature for 1.5 hrs, allowed to warm to ambient temperature, and stirred for 1 hr. The reaction mixture was cooled in an ice bath, poured into ice water, and extracted with ethyl acetate. The extracts were washed with cold 2% sodium hydroxide solution, cold brine, dried over anhydrous sodium sulfate, filtered, and the filtrate was concentrated. The residue was dissolved in chloroform and flash chromatographed (silica gel), eluting with chloroform, 1% and 2% methanol/chloroform. The appropriate fractions were collected and concentrated to provide 0.25 g (72%) of product, as the free base. The free base was dissolved in chloroform/ether. Ethereal hydrogen chloride was added. The precipitate was collected and recrystallized from ethanol to provide product, mp 163–192° C.

Analysis: Calculated for $C_{21}H_{31}ClN_3O_4$: 55.03%; C, 6.38%; H, 9.17%; N, Found: 55.21%; C, 6.33%; H, 9.04%; N.

EXAMPLE 97

4-[3-[2-Methoxy-5-(pyrrolidin-1-yl-methyl) phenoxy]prop-1-ynyl]tetrahydrothiopyran-4-ol Hydrochloride To a solution of 4-methoxy-3-propargyloxypyrrolidinomethylbenzene (4.58 g) in dry tetrahydrofuran (25 ml), cooled in an ice bath, was added, dropwise, a solution of 2.5 M n-butyllithium (7.3 ml) at a rate such that the temperature remained below 5°. The reaction mixture was stirred for 20 mins at −5 to 5°, cooled to −30 to −35° and to the solution was added dropwise a solution of tetrahydrothiopyran-4-one (2.07 g) in tetrahydrofuran (23 ml) at a rate such that the temperature remained below −30°. The reaction mixture was stirred at −35 to −30° for 0.5 hr, poured into ice/water, extracted with chloroform, and the combined chloroform extracts were washed with water, dried over anhydrous sodium sulfate, filtered, and the filtrate was concentrated. The residue was dissolved in chloroform and chromatographed (high performance liquid chromatography) on silica gel, eluting with 5% methanol/chloroform followed by 10% methanol/chloroform. The appropriate fractions were collected and concentrated to give 4.50 g (66.3%) of product, as the free base. The free base was dissolved in ether and ethereal hydrogen chloride was added. The precipitate was collected to provide the analytical sample, mp 178–1 80° C.

Analysis: Calculated for $C_{20}H_{28}ClNO_3S$: 60.36%; C, 7.09%; H, 3.52%; N, Found: 60.37%; C, 7.11%; H, 3.49%; N.

EXAMPLE 98

1-[1-(4-Hydroxy-3-methoxyphenyl)ethyl]-4-(2-chlorophenyl)piperazine Hemihydrate A solution of 1-[1-(4-acetoxy-3-methoxyphenyl)ethyl]-4-(2-chlorophenyl)piperazine(8.0 g) in 50% sodium hydroxide solution (8 ml) and 50% aqueous ethanol (50 ml) was heated for 24 hrs at 50° C., under nitrogen. The reaction mixture was diluted with ethyl acetate (150 ml), neutralized with 10% hydrochloric acid, dried over anhydrous sodium sulfate, filtered, and the filtrate was concentrated in vacuo. The residue was flash chromatographed (silica gel), eluting with 1% acetone/1% methanol/dichloromethane. The appropriate fractions were collected and concentrated to yield 4.5 g (90%) of product, mp 62–63° C.

Analysis: Calculated for $C_{19}H_{23}N_2O_2 \cdot 1/2\ H_2O$: 64.13%; C, 6.80%; H, 7.87%; N, Found: 64.01%; C, 6.58%; H, 7.69%; N.

EXAMPLE 99

N-(2-Chloro-4-[N,N-dimethylcarbamoyloxyl-5-methoxy)benzyl-N'-pyridin-2-yl-piperazine Cesium carbonate (0.51 g) was added to a solution of N-(2-chloro-4-hydroxy-5-methoxy)benzyl-N'-pyridin-2-ylpiperazine (0.35 g) and N,N-dimethylcarbamoyl chloride (0.25 ml) in dichloromethane (20 ml), and the reaction mixture was stirred for 48 hrs at ambient temperature. Water and brine (250 ml) were added, and the mixture was extracted with dichloromethane. The organic extracts were dried over anhydrous sodium sulfate, filtered, and the filtrate was concentrated in vacuo. The residue was flash chromatographed (silica gel), eluting with 25–100% ethyl acetate/heptane. The appropriate fractions were collected and concentrated to afford 0.40 g (95%) of product. Recrystallization from ethyl acetate gave the analytical sample, mp 126–127° C.

Analysis Calculated for $C_{20}H_{25}ClN_4O_3$: 59.33%; C, 6.22%; H, 13.84%; N, Found: 59.62%; C, 6.26%; H, 13.63%; N.

EXAMPLE 100

N-(2-Chloro-4-benzyloxy-5-methoxy-N'-(2-chlorophenyl)piperazine

Sodium hydride (50% dispersion-in-oil, 0.85 g) was added slowly to a suspension of 4-benzyloxy-2-chloro-5-methoxybenzyl chloride (2.0 g) and 2-chlorophenylpiperazine monohydrochloride (1.9 g) in dichloromethane (70 ml), and the reaction mixture was stirred for 24 hrs at ambient temperature. Water and brine (250 ml) were added, and the mixture was extracted with dichloromethane. The organic extracts were dried over anhydrous sodium sulfate, filtered, and the filtrate was concentrated in vacuo. The residue was flash chromatographed (silica gel), eluting with 20–60% ethyl acetate/heptane. The appropriate fractions were collected and concentrated to afford 1.94 g (62%) of product. Recrystallization from dichloromethane/heptane gave the analytical sample, mp 95–97° C.

Analysis Calculated for $C_{25}H_{26}Cl_2N_2O_2$: 65.65%; C, 5.73%; H, 6.12%; N, Found: 65,80%; C, 5.66%; H, 5.77%; N.

EXAMPLE 101

N-(2-Chloro-4-hydroxy)benzyl-N'-(2-methoxyphenyl)piperazine

Sodium triacetoxyborohydride (3.80 g) was added to a solution of 2-chloro-4-hydroxybenzaldehyde(2.15 g) and 2-methoxyphenylpiperazine(2.93 g) in dichloromethane (75 ml), at ambient temperature. The reaction mixture was stirred at ambient temperature for 72 hrs, quenched with water, diluted with brine (250 ml), and extracted with dichioromethane. The organic extracts were dried over anhydrous sodium sulfate, filtered, and the filtrate was concentrated in vacuo. The residue was flash chromatographed (silica gel), eluting with 20–50% ethyl acetate/heptane. The appropriate fractions were collected and concentrated to afford 2.34 g (51%) of product. Recrystallization from ethyl acetate/heptane gave the analytical sample, mp 186–187° C.

Analysis: Calculated for $C_{18}H_{21}ClN_2O_2$: 64.96%; C, 6.36%; H, 8.42%; N, Found: 64.78%; C, 6.35%; H, 8.29%; N.

EXAMPLE 102

N-(2-Bromo-5-[N,N-dimethylcarbamoyloxyl-4-methoxy)benzyl-N'-(2-methoxyphenyl)piperazine Cesium carbonate (0.50 g) was added to a solution of N-(2-bromo-5-hydroxy-4-methoxy)benzyl-N'-(2-methoxyphenyl)piperazine (0.42 g) and N,N-dimethylcarbamoyl chloride (0.25 ml) in (20 ml), at ambient temperature. The reaction mixture was stirred at ambient temperature for 72 hrs, quenched with water, diluted with brine (250 ml), and extracted with dichloromethane. The organic extracts were dried over anhydrous sodium sulfate, filtered, and the filtrate was concentrated in vacuo. Recrystallization of the residue from dichloromethane/heptane gave 0.31 g (73%) of product, mp 139–140° C.

Analysis: Calculated for $C_{22}H_{28}BrN_3O_4$: 55.24%; C, 5.90%; H, 8.78%; N, Found: 55.19%; C, 5.74%; H, 8.59%; N.

EXAMPLE 103

N-(3-Fluoro-4-hydroxy)benzyl-N'-(2-methoxyphenyl)piperazine

Sodium triacetoxyborohydride (2.68 g) was added portionwise over about 10 mins to a solution of 3-fluoro-4-methoxybenzaldehyde (1.50 g) and N-(2-methoxyphenyl)piperazine (2.28 g) in dichloromethane (40 ml), at ambient temperature. The reaction mixture was stirred for 48 hrs, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 20–60% ethyl acetate/heptane. The appropriate fractions were collected and concentrated to afford 3.06 g (95%) of product, mp 55–57° C.

Analysis: Calculated for $C_{19}H_{23}FN_2O_2$: 69.07%; C, 7.02%; H, 8.48%; N, Found: 68.87%; C, 7.02%; H, 8.29%; N.

EXAMPLE 104

N-(2,6-Dibromo-3-[N,N-dimethylcarbamoyloxy]-4-methoxy)benzyl-6,7-dimethoxy-1,2,3,4-tetrahydroisoquinoline Cesium carbonate (0.75 g) was added to a solution of N-(2,6-dibromo-3-hydroxy-4-methoxy)benzyl-6,7-dimethoxy-1,2,3,4-tetrahydroisoquinoline (0.75 g) and dimethylcarbamoyl chloride (0.35 ml) in dichloromethane (20 ml), at ambient temperature. The reaction mixture was stirred for 24 hrs, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 20–60% ethyl acetate/heptane. The appropriate fractions were collected and concentrated to afford 0.47 g (5 5%) of product, mp 162–163° C.

Analysis: Calculated for $C_{22}H_{26}Br_2N_2O_5$: 47.33%; C, 4.69%; H, 5.02%; N, Found: 47.24%; C, 4.33%; H, 4.83%; N.

EXAMPLE 105

1-[11-(4-Hydroxy-3-methoxyphenyl)ethyl]-4-(2-trifluoromethylphenyl)piperazine Hydrochloride A solution of 1-[1-(4-acetoxy-3-methoxyphenyl)ethyl]-4-(2-trifluoromethylphenyl)piperazine(2.8 g) in 50% sodium hydroxide solution (5 ml) and 50% aqueous ethanol (50 ml) was stirred, under nitrogen, for 24 hrs. The reaction mixture was diluted with ethyl acetate (150 ml), neutralized with 10% hydrochloric acid, dried over anhydrous sodium sulfate, filtered, and the filtrate was concentrated in vacuo. The residue was flash chromatographed (silica gel), eluting with 1% acetone/1% methanol/dichloromethane. The appropriate fractions were collected and concentrated. The residue was dissolved in ethyl acetate (150 ml), ethereal hydrogen chloride was added. The precipitate was collected and dried to give 0.4 g (16%) of product, mp 180–181° C.

Analysis: Calculated for $C_{20}H_{24}ClF_3N_2O_2$: 57.62%; C, 5.80%; H, 6.72%; N, Found: 57.48%; C, 5.80%; H, 6.64%; N.

EXAMPLE 106

1-[1-(4-N,N-dimethylcarbamoyloxy-3-methoxyphenyl)ethyl]4-(2-trifluoromethylphenyl)piperazine Hydrochloride To a solution of 1-[1-(4-hydroxy-3-methoxyphenyl)ethyl]-4-(2-trifluoromethylphenylpiperazine (0.5 g) and cesium carbonate (0.4 g) in 25% acetonitrile/dichloromethane (15 ml) was added dimethylcarbamyl chloride (0.3 g) under nitrogen, with stirring. The reaction mixture was stirred for 18 hrs and diluted with ethyl acetate (150 ml). The solution was washed with water, dried over anhydrous sodium sulfate, filtered, and the filtrate was concentrated in vacuo. The residue was flash chromatographed (silica gel), eluting with 1% methanol/dichloromethane. The appropriate fractions were collected and concentrated and treated with ethereal hydrogen chloride to provide 0.20 g (33%) of product, mp 123–124° C.

Analysis: Calculated for $C_{23}H_{29}ClN_3O_3$: 56.62%; C, 5.99%; H, 8.61%; N, Found: 56.54%; C, 5.84%; H, 8.51%; N.

EXAMPLE 107

1-[1-(4-N,N-Dimethylcarbamoyloxy-3-methoxyphenyl)ethyl]-4-(2-chlorophenyl)-piperazine To a solution of 1-[1-(4-hydroxy-3-methoxyphenyl)ethyl]-4-(2-chlorophenyl)piperazine (0.75 g) and cesium carbonate (0.70 g) in 25% acetonitrile/dichloromethane (35 ml) was added dimethylcarbamyl chloride (0.47 g), under nitrogen, with stirring. The reaction mixture was stirred for 18 hrs and diluted with ethyl acetate. The solution was washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated to afford 0.2 g (22%) of product, mp 55–56° C.

Analysis: Calculated for $C_{22}H_{28}ClN_3O_3$: 63.23%; C, 6.75%; H, 10.05%; N, Found: 63.14%; C, 6.74%; H, 9.78%; N.

EXAMPLE 108

1-[1-(3-Methoxy-4-N-methylcarbamoyloxyphenyl)ethyl]-4-(2-trifluoromethylphenyl)-piperazine Hemihydrate To a solution of 1-[1-(4-hydroxy-3-methoxyphenyl)ethyl]-,4-(2-trifluoromethylphenyl)-piperazine (0.65 g) and copper (I) chloride (catalytic quantity) in ethyl acetate (20 ml) was added methyl isocyanate (0.1 g), under nitrogen, with stirring. The reaction mixture was stirred for 3 hrs and diluted with ethyl acetate. The solution was washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated to afford 0.22 g (30%) of product, mp 61–62° C.

Analysis:

Calculated for $C_{22}H_{26}N_3O_3F_3.1/2\ H_2O$: 59.18%; C, 6.10%; H, 9.41%; N, Found: 59.28%; C, 5.84%; H, 9.46%; N.

EXAMPLE 109

1-[1-(4-Hydroxy-3-methoxyphenyl)ethyl]-4-(2-methylphenyl)piperazinehydrochloride Hemihydrate A solution of 1-[1-(4-acetoxy-3-methoxyphenyl)ethyl]-4-(2-methylphenyl)piperazine (3.2 g) in 50% sodium hydroxide solution (8 ml) and 50% aqueous ethanol (50 ml) was heated for 24 hrs, under nitrogen, at 50° C. The reaction mixture was diluted with ethyl acetate (150 ml), neutralized with 10% hydrochloric acid solution, dried over anhydrous sodium sulfate, filtered, and the filtrate was concentrated in vacuo. The residue was flash chromatographed (silica gel), eluting with 1% acetone/1% methanol/dichloromethane. The appropriate fractions were collected and concentrated. The residue was dissolved in ethyl acetate (100 ml) and treated with ethereal hydrogen chloride to provide 2.5 g (78%) of product, mp 135–136° C.

Analysis: Calculated for $C_{20}H_{27}ClN_2O_2.1/2\ H_2O$: 64.59%; C, 7.59%; H, 7.53%; N, Found: 64.67%; C, 7.39%; H, 7.45%; N.

EXAMPLE 110

1-[1-(4-N,N-Dimethylcarbamoyloxy-3-methoxyphenyl)ethyl]-4-(2-methylphenyl)-piperazine Sesquihydrochloride Hemihydrate To a solution of 1-[1-(4-hydroxy-3-methoxyphenyl)ethyl]-4-(2-methylphenyl)piperazine(1.0 g) and cesium carbonate (1.0 g) in 25% acetonitrile/dichloromethane (35 ml) was added dimethylcarbamyl chloride (0.8 g), under nitrogen, with stirring. The reaction mixture was stirred for 18 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated. The residue was treated with ethereal hydrogen chloride in ethyl acetate to afford 0.2 g (16%) of product, mp 128–129° C.

Analysis: Calculated for $C_{23}H_{31}N_3O_3.3/2\ HCl.1/2H_2O$: 59.90%; C, 7.32%; H, 9.11%; N, Found: 60.02%; C, 7.02%; H, 9.04%; N.

EXAMPLE 111

1-[14-Methoxy-3-(dimethylaminocarbonyloxy)phenyl methyl]-4-(2-chlorophenyl)piperazine Hydrochloride To a solution of 4-methoxy-(3-dimethylaminocarbonyloxy)benzaldehyde (2.0 g) in 1,2-dichloroethane (17 ml) was added 1-(2-chlorophenyl)piperazine (1.76 g) in 1,2-dichloroethane (17 ml), followed by sodium triacetoxyborohydride (2.85 g), with stirring. The reaction mixture was stirred at ambient temperature for 2 hrs, poured into saturated sodium carbonate solution (100 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica gel), eluting with dichloromethane, followed by 0.1, 0.2, 0.3, 0.4, 0.5% methanol:dichloromethane, respectively. The appropriate fractions were collected and concentrated to yield 2.86 g (79%) of product, free base. The free base was dissolved in diethyl ether and ethereal hydrogen chloride was added. The precipitate was collected, dried at ambient temperature under high vacuum and recrystallized from 2-propanol to give product, mp 214–216° C.

Analysis: Calculated for $C_{21}H_{27}Cl_2N_3O_3$: 57.28%; C, 6.18%; H, 9.54%; N, Found: 57.14%; C, 6.15%; H, 9.45%; N.

EXAMPLE 112

1-[[3-(Methoxy)-4-(dimethylaminocarbonyloxy)phenyl]methyl]-4-(2-methylphenyl)piperazine Hydrochloride To a solution of 3-(methoxy)-4-dimethylaminocarbonyloxy)benzaldehyde (1.01 g) in 1,2-dichloroethane (18 ml) was added 1-(2-tolyl)piperazine (0.80 g) and sodium triacetoxyborohydride ((1.44 g), with stirring. The reaction mixture was stirred at ambient temperature for 4.5 hrs, poured into ice/saturated sodium carbonate solution (75 ml) and extracted with dichloromethane. The combined organic extracts were washed with water and brine, dried over anhydrous sodium sulfate, filtered, and the filtrate was concentrated. The residue was dissolved in dichloromethane and flash chromatographed (silica gel), eluting with dichloromethane, followed by 0.1, 0.2, 0.5, 1% methanol:dichloromethane, respectively. The appropriate fractions were combined and concentrated. The residue was dissolved in diethyl ether and ethereal hydrogen chloride was added. The precipitate was collected, dried at ambient temperature under high vacuum and recrystallized from 2-propanol to give product mp 230–250° C. (dec).

Analysis: Calculated for $C_{22}H_{30}ClN_3O_3$: 62.92%; C, 7.20%; H, 10.01%; N, Found: 62.81%; C, 7.06%; H, 9.88%; N.

EXAMPLE 113

N-(2,6-Dibromo-3-hydroxy-4-methoxy)benzyl-6,7-dimethoxy-1,2,3,4-tetrahydroisoquinoline Sodium hydride (80% dispersion-in-oil, 0.96 g) was added to a solution of (2,6-dibromo-3-hydroxy-4-methoxy) benzyl bromide (3.0 g) and 6,7-dimethoxy-1,2,3,4-tetrahydroisoquinoline hydrochloride (2.0 g) in dichloromethane (100 ml), at ambient temperature. The reaction mixture was stirred at ambient temperature for 24 hrs, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel) eluting with 25–75% ethyl acetate/heptane. The appropriate fractions were collected and concentrated to afford 2.9 g (74%) of product, free base. A portion of the free base was dissolved in ethyl acetate, cooled to 0° C., and ethereal hydrogen chloride was added followed by diethyl ether. The precipitate was collected and recrystallized from methanol/diethyl ether to afford product, mp 159–162° C.

Analysis: Calculated for $C_{20}H_{25}Br_2ClNO_4$: 44.59%; C, 4.68%; H, 2.60%; N, Found: 44,12%; C, 4.39%; H, 2.36%; N.

EXAMPLE 114

N-(2,6-Dibromo-3-hydroxy-4-methoxy)benzyl-N'-(2-chlorophenyl)piperazine

Sodium hydride (80% dispersion-in-oil, 0.40 g) was added to a solution of (2,6-dibromo-3-hydroxy-4-methoxy) benzyl bromide (1.0 g) and N-(2-chlorophenyl)piperazine (0.88 g) in dichloromethane (30 ml), at ambient temperature. The reaction mixture was stirred at ambient temperature for 24 hrs, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 10–25% ethyl acetate/heptane. The appropriate fractions were collected and concentrated to afford 1.2 g (85%) of product, mp 155–157° C.

Analysis: Calculated for $C_{18}H_{19}Br_2ClN_2O_2$: 44.07%; C, 3.90%; H, 5.71%; N, Found: 44.12%; C, 3.73%; H, 5.61%; N.

EXAMPLE 115

N-(2-Chloro-5-hydroxy-4-methoxy)benzyl-N'-(2-chlorophenyl)piperazine

Sodium hydride (80% dispersion-in-oil, 0.60 g) was added to a solution of (2-chloro-5-hydroxy-4-methoxy) benzyl chloride (1.0 g) and N-(2-chlorophenyl) piperazinehydrochloride (1.3 g) in dichloromethane (40 ml), at ambient temperature. The reaction mixture was stirred for 24 hrs at ambient temperature, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 10–25% ethyl acetate/heptane. The appropriate fractions were collected and concentrated to afford 0.50 g (28%) of product. Recrystallization from ethyl acetate/heptane gave the analytical sample, mp 155–157° C.

Analysis: Calculated for $C_{18}H_{20}Cl_2N_2O_2$: 58.87%; C, 5.49%; H, 7.63%; N, Found: 58.98%; C, 5.43%; H, 7.50%; N.

EXAMPLE 116

N-(4-Benzyloxy-2-chloro-5-methoxy)benzyl-N'-(2-methoxyphenyl)piperazine

Sodium hydride (80% dispersion-in-oil, 0.61 g) was added to a solution of (4-benzyloxy-2-chloro-5-methoxy) benzyl chloride (2.0 g) and N-(2-methoxyphenyl)piperazine (1.6 g) in dichloromethane (50 ml), at ambient temperature. The reaction mixture was stirred for 24 hrs at ambient temperature, quenched with water, diluted with brine (250 ml), and extracted with dichloromethane. The organic extracts were dried over anhydrous sodium sulfate, filtered, and the filtrate was concentrated in vacuo. The residue was flash chromatographed (silica gel), eluting with 20–40% ethyl acetate/heptane. The appropriate fractions were collected and concentrated to afford 2.0 g (64%) of product. Trituration from dichloromethane gave the analytical sample, mp 86–88° C.

Analysis: Calculated for $C_{26}H_{29}ClN_2O_3$: 68.94%; C, 6.45%; H, 6.18%; N, Found: 69.07%; C, 6.44%; H, 5.97%; N.

EXAMPLE 117

N-(3-Fluoro-4-methoxy)benzyl-N'-(2-chlorophenyl) piperazine

Sodium triacetoxyborohydride (3.58 g) was added to a solution of 3-fluoro-4-methoxybenzaldehyde (2.04 g) and N-(2-chlorophenyl)piperazine (3.05 g) in dichloromethane (50 ml), at ambient temperature. The reaction mixture was stirred for 24 hrs at ambient temperature, quenched with water, diluted with brine (250 ml), and extracted with dichloromethane. The organic extracts were dried over anhydrous sodium sulfate, filtered, and the filtrate was concentrated in vacuo. The residue was flash chromatographed (silica gel), eluting with 10–35% ethyl acetate/heptane. The appropriate fractions were collected and concentrated to afford 3.92 g (87%) of product, free base. A portion of the free base was dissolved in ethyl acetate, cooled to 0° C., and ethereal hydrogen chloride was added. The precipitate was collected and dried in vacuo. Recrystallization from methanol/diethyl ether gave the analytical sample, mp 242–245° C.

Analysis: Calculated for $C_{18}H_{21}Cl_2N_2O$: 58.23%; C, 5.70%; H, 7.54%; N, Found: 57.79%; C, 5.60%; H, 7.36%; N.

EXAMPLE 118

N-(3-Chloro-4-hydroxy-5-methoxy)benzyl-N'-(2-chlorophenyl)piperazine

A solution of N-(4-benzyloxy-2-chloro-5-methoxy) benzyl-N'-(2-chlorophenyl)piperazine (1.70 g) in dichloromethane (25 ml) was added to a suspension of ferric chloride (3.70 g) in dichloromethane(50 ml), at ambient temperature. The reaction mixture was heated under reflux for 24 hrs, filtered, and the filtrate was washed with dichloromethane. The filter cake was suspended in 5% potassium hydroxide solution (250 ml) and stirred for 2 hrs at ambient temperature. The suspension was neutralized with hydrochloric acid and filtered. The filtrate was extracted with dichloromethane. The organic extracts were dried over anhydrous sodium sulfate, filtered, and the filtrate was concentrated in vacuo. The residue was flash chromatographed (silica gel), eluting with 20–50% ethyl acetate/heptane. The appropriate fractions were collected and concentrated to afford 0.80 g (58%) of product. Recrystallization from ethyl acetate/heptane gave the analytical sample, mp 143–145° C.

Analysis: Calculated for $C_{18}H_{20}Cl_2N_2O_2$: 58.87%; C, 5.49%; H, 7.63%; N, Found: 58.82%; C, 5.38%; H, 7.45%; N.

EXAMPLE 119

1-[[4-Methylaminocarbonyloxy)-3-)methoxy)phenyl]methyl]-4-(3-fluoropyridin-2-yl)piperazine Hydrochloride Hydrate A solution of 4-(methylaminocarbonyloxy)-3-methoxybenzaldehyde, (0.49 g), 3-(fluoropyridin-2-yl)piperazine (0.506 g) and 1,2-dichloroethane (7 ml), was added to sodium triacetoxyborohydride (0.65 g), with stirring. The reaction mixture was stirred for 2.5 hrs at ambient temperature, poured into ice/sodium carbonate and extracted with ethyl acetate. The extracts were washed with water, brine, dried over anhydrous sodium sulfate, filtered, and the filtrate was concentrated. The residue was dissolved in chloroform and flash chromatographed (silica gel), eluting with chloroform, 1% and 2% methanol/chloroform. The appropriate fractions were combined and concentrated to afford 0.79 g (90%) of product, free base. The free base was dissolved in chloroform, diluted with ether, ethereal hydrogen chloride was added. The precipitate was collected, dried at ambient temperature and recrystallized from acetonitrile to provide 0.321 g of product, mp 172–174° C.

Analysis: Calculated for $C_{29}H_{26}ClFN_4O_4 \cdot H_2O$: 53.21%; C, 6.11%; H, 13.06%; N, Found: 53.65%; C, 5.81%; H, 13.27%; N.

EXAMPLE 120

1-[[3-Methoxy-4-[1-(phenyl)ethylaminocarbonyloxylphenyl]methyl]-4-(2-fluorophenyl)piperazine Hydrochloride To a solution of 3-methoxy-4-[1-(phenyl)ethylaminocarbonyloxy]benzaldehyde(0.69 g) in 1.2-dichloroethane (10 ml) was added 1-(2-fluorophenyl)piperazine (0.42 g), followed by sodium triacetoxyborohydride (0.73 g), with stirring. The reaction mixture was stirred for 5 hrs at ambient temperature, poured into saturated sodium carbonate solution (75 ml) and extracted with dichloromethane. The extracts were washed with water and brine, dried over anhydrous sodium sulfate, filtered, and the filtrate was concentrated. The residue was dissolved in dichloromethane and flash chromatographed (silica gel), eluting with dichloromethane, followed by 0.2, 0.4, 0.6, 1.0% methanol:dichloromethane. The appropriate fractions were collected and concentrated to afford 0.61 g (57%) of product, free base. The free base was dissolved in diethyl ether and ethereal hydrogen chloride was added. The precipitate was collected and recrystallized from 2-propanol (dried under high vacuum at 78° C. for 2 hrs) to give the analytical sample, mp 204–207° C. (dec).

Analysis: Calculated for $C_{21}H_{31}ClFN_3O_3$: 64.86%; C, 6.25%; H, 8.40%; N, Found: 64.83%; C, 6.51%; H, 8.09%; N.

EXAMPLE 121

N-(2-Chloro-4-[N,N-dimethylcarbamoyloxyl]benzyl-N'-(2-methoxyphenyl)piperazine Hydrochloride Hydrate Cesium carbonate (0.85 g) was added to a solution of N(2-hyrdoxy)benzyl-N'-(2-methoxyphenyl)piperazine (0.75 g) and N,N-dimethylcarbamoyl chloride (0.40 ml) in dichloromethane (20 ml), at ambient temperature. The reaction mixture was stirred for 72 hrs at ambient temperature, quenched with water, diluted with brine (250 ml) and extracted with dichloromethane. The organic layers were dried over anhydrous sodium sulfate, filtered, and the filtrate was concentrated in vacuo. The residue was flash chromatographed (silica gel), eluting with 10–40% ethyl acetate/heptane. The appropriate fractions were collected and concentrated to afford 0.58 g (64%) of product, free base. The free base was dissolved in ethyl acetate, cooled to 0° C., and ethereal hydrogen chloride was added. Diethyl ether was added, and the precipitate was collected. Recrystallization from methanol/diethyl ether gave the analytical sample, 208–210° C.

Analysis: Calculated for $C_{21}H_{29}Cl_2N_3O_4$: 55.03%; C, 6.38%; H, 9.17%; N, Found: 55.36%; C, 5.97%; H, 9.11%; N.

EXAMPLE 122

N-(2-Chloro-4-hydroxy-5-methoxy)benzyl-N'-(2-methoxyphenyl)piperazine Hydrochloride Hydrate A solution of N-(4-benzyloxy-2-chloro-5-methoxy)benzyl-N'-(2-methoxyphenyl)piperazine (1.30 g) in dichloromethane (20 ml) was added to a suspension of ferric chloride (2.35 g) in dichloromethane (40 ml), at ambient temperature. The reaction mixture was heated under reflux for 24 hrs, filtered, and the filter cake was washed with dichloromethane. The filter cake was suspended in 5% potassium hydroxide solution (250 ml) and stirred for 2 hrs at ambient temperature. The suspension was neutralized with hydrochloric acid and filtered. The aqueous filtrate was extracted with dichloromethane. The organic layers were dried over anhydrous sodium sulfate, filtered, and the filtrate was concentrated in vacuo. The residue was flash chromatographed (silica gel), eluting with 20–100% ethyl acetate/heptane. The appropriate fractions were collected and concentrated to give 0.60 g (58%) of product, free base. The free base was dissolved in methanol, acidified with ethereal hydrogen chloride and concentrated to about 5 ml. Trituration with diethyl ether and recrystallization from methanol/diethyl ether gave the analytical sample, mp 173–175° C.

Analysis: Calculated for $C_{19}H_{26}Cl_2N_2O_4$: 54.68%; C, 6.28%; H, 6.71%; N, Found: 55.08%; C, 6.34%; H, 6.23%; N.

EXAMPLE 123

N-(3-Fluoro-4-hydroxy)benzyl-N'-(2-chlorophenyl)piperazine Hydrochloride Hemihydrate N-(3-Fluoro-4-hydroxy)benzyl-N'-2-chlorophenyl)piperazine (3.0 g) was added to 48% hydrobromic acid (45 ml), at ambient temperature. The reaction mixture was heated at 100° C. for 24 hrs, cooled to ambient temperature, diluted with water (200 ml), neutralized with potassium hydroxide and extracted with ethyl acetate. The organic layers were dried over anhydrous sodium sulfate, filtered, and the filtrate was concentrated in vacuo. The residue was flash chromatographed (silica gel), eluting with 1–5% methanol/dichloromethane. The appropriate fractions were collected and concentrated to give 2.27 g (79%) of product, free base. A portion of the free base was dissolved in methanol, cooled to 0° C., and ethereal hydrogen chloride was added. The precipitate was collected and recrystallization from methanol/diethyl ether gave the analytical sample 130–132° C.

Analysis Calculated for $C_{17}H_{19}Cl_2FN_3O.1/2$ $H_2O$: 55.75%; C, 5.50%; H, 7.65%; N, Found: 55.94%; C, 5.15%; H, 7.52%; N.

EXAMPLE 124

1-[1-(3-Methoxy-4-N-methylcarbamoyloxyphenyl) ethyl]-4-(2-chlorophenyl)piperazine Hydrochloride Hemihydrate To a solution of 1-[1-(4-hydroxy-3-methoxyphenyl) ethyl)-4-(2-chlorophenyl)piperazine (0.75 g) and copper (I) chloride in ethyl acetate (20 ml) was added methyl isocyanate (0.12 g), under nitrogen, with stirring. The reaction mixture was stirred for 3 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated. The residue was dissolved in ethyl acetate (100 ml) and acidified with ethereal hydrogen chloride. The precipitate was collected to afford 0.20 g (23%) of product, mp 141–142° C.

Analysis: Calculated for $C_{21}H_{27}ClN_3O_3Cl.1/2$ $H_2O$: 56.13%; C, 6.28%; H, 9.35%; N, Found: 56.36%; C, 6.11%; H, 9.45%; N.

EXAMPLE 125

1-[1-(4-Hydroxy-3-methoxyphenyl)ethyl]-4-(2-quinolinyl)piperazine Hemihydrate

A solution of 1-[1-(4-acetoxy-3-methoxyphenyl)ethyl]-4-(2-quinolinyl)piperazine(4.7 g) in 50% sodium hydroxide solution (8 ml) and 50% aqueous ethanol (50 ml) was heated at 50° C. for 24 hrs, under nitrogen. The reaction mixture was diluted with ethyl acetate (150 ml), neutralized with 10% hydrochloric acid and dried over anhydrous sodium sulfate, filtered, and the filtrate was concentrated in vacuo. The residue was flash chromatographed (silica gel), eluting with 1% acetone/1% methanol/dichloromethane. The appropriate fractions were collected and concentrated to afford 1.8 g (43%) of product, mp 53–54° C.

Analysis: Calculated for $C_{22}H_{25}N_3O_2O.1/2H_2O$: 70.94%; C, 7.04%; H, 11.28%; N, Found: 70.53%; C, 6.96%; H, 11.02%; N.

EXAMPLE 126

1-[1-(4-N,N-Dimethylcarbamoyloxy-3-methoxyphenyl)ethyl]-4-(2-quinolinyl)-piperazine Hemihydrate To a solution of 1-[1-(4-hydroxy-3-methoxyphenyl) ethyl]-4-(2-quinolinyl)piperazine (0.6 g) and cesium carbonate (0.5 g) in 25% acetonitrile/dichloromethane (15 ml) was added dimethylcarbamyl chloride (9.4 g), under nitrogen, with stirring. The reaction mixture was stirred for 18 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated to afford 0.3 g (46%) of product, mp 58–59° C.

Analysis: Calculated for $C_{25}H_{30}N_4O_3.1/2H_2O$: 67.70%; C, 7.04%; H, 12.63%; N, Found: 68.00%; C, 6.78%; H, 12.47%; N.

EXAMPLE 127

1-[1-(3-Metboxy-4-N-methylcarbamoyloxyphenyl) ethyl]-4-(2-quinolinyl)piperazine Dihydrochloride To a solution of 1-[1-(4-hydroxy-3-methoxyphenyl) ethyl]-4-(2-quinolinyl)piperazine (0.90 g) and copper (I) chloride in ethyl acetate (15 ml) was added methyl isocyanate (0.14 g), under nitrogen, with stirring. The reaction mixture was stirred for 3 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and evaporated. The residue was dissolved in ethyl acetate and acidified with ethereal hydrogen chloride. The precipitate was collected to afford 0.20 g (23%) of product, nip 182–183° C.

Analysis: Calculated for $C_{24}H_{30}Cl_2N_4O_3$: 58.42%; C, 6.13%; H, 11.35%; N, Found: 58.22%; C, 6.31%; H, 11.07%; N.

EXAMPLE 128

1-[1-(3-Methoxy-4-N-methylcarbamoyloxyphenyl) ethyl]-4-(2-methylphenyl)piperazine Hydrochloride Hydrate To a solution of 1-[1-(4-hydroxy-3-methoxyphenyl) ethyl]-4-(2-methylphenyl)piperazine (0.50 g) and copper (I) chloride in ethyl acetate (15 ml) was added methyl isocyanate (0.09 g), under nitrogen, with stirring. The reaction mixture was stirred for 3 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated. The residue was dissolved in ethyl acetate (100 ml) and acidified with ethereal hydrogen chloride. The precipitate was collected to give 0.20 g (23%) of product, mp 178–179° C.

Analysis: Calculated for $C_{22}H_{32}ClN_3O_4$: 60.33%; C, 7.36%; H, 9.59%; N, Found: 60.11%; C, 7.05%; H, 9.39%; N.

EXAMPLE 129

1-[1-(3-Methoxy-4-N-methylcarbamoyloxyphenyl) ethyl]-4-[2-(4-methylquinolinyl)]piperazine Hemihydrate To a solution of 1-[1-(4-hydroxy-3-methoxyphenyl) ethyl]-4-[2-(4-methyl-quinolinyl)])piperazine (1.0 g) and copper (T) chloride in ethyl acetate (20 ml) was added methyl isocanate (0.15 g), under nitrogen. The reaction Mixture was stirred for 3 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated to afford 0.3 g (27%) of product, mp 65–66° C.

Analysis: Calculated for $C_{25}H_{30}N_4O_3 \cdot 1/2\ H_2O$: 67.70%; C, 7.04%; H, 12.63%; N, Found: 67.20%; C, 6.81%; H, 12.23%; N.

EXAMPLE 130

1-[1-(4-Hydroxy-3-methoxyphenyl)ethyl]-4-[2-(4-methylquinolinyl)]piperazine Dihydrochloride A solution of 1-[1-(4-acetyl-3-methoxyphenyl)ethyl]-4-[(2-(4-methylquinolinyl)])piperazine (35 g) in 50% sodium hydroxide solution (8 ml) and 50% aqueous ethanol (50 ml) was heated for 24 hrs at 50° C., under nitrogen. The reaction mixture was diluted with ethyl acetate (150 ml), neutralized with 10% hydrochloric acid solution, dried over anhydrous sodium sulfate, filtered, and the filtrate was concentrated in vacuo. The residue was flash chromatographed (silica gel), eluting with 1% acetone/1% methanol/dichloromethane. The appropriate fractions were collected and concentrated. The residue was dissolved in ethyl acetate (100 ml) and ethereal hydrogen chloride was added. The precipitate was collected to provide 2.2 g (71%) of product, mp 155–156° C.

Analysis: Calculated for $C_{21}H_{29}Cl_2N_3O_2$: 61.33%; C, 6.49%; H, 9.33%; N, Found: 61.58%; C, 6.60%; H, 8.95%; N.

EXAMPLE 131

1-[1-(4-N,N-Dimethylcarbamoyloxy-3-methoxyphenyl)ethyl]-4-[(2-(4-methylquinolinyl)] piperazine To a solution of 1-[1-(4-hydroxy-3-methoxyphenyl) ethyl]-4-[(2-(4-methylquinolinyl]piperazine (1.0 g) and cesium carbonate (0.8 g) in 25% acetonitrile/dichloromethane (20 ml) was added dimethylcarbamyl chloride (0.6 g), under nitrogen, with stirring. The reaction mixture was stirred for 18 hrs, diluted with ethyl acetate, washed with brine, dried over anhydrous sodium sulfate, filtered, and the filtrate was concentrated in vacuo. The residue was flash chromatographed (silica gel), eluting with 1% methanol/dichloromethane. The appropriate fractions were collected and concentrated to give 0.4 g (36%) of product, mp 68–69° C.

Analysis: Calculated for $C_{26}H_{32}N_4O_3$: 69.62%; C, 7.19%; H, 12.49%; N, Found: 69.03%; C, 7.06%; H, 12.35%; N.

EXAMPLE 132

N-(3-Fluoro-4-hydroxy)benzyl-N'-(2-hydroxy) phenylpiperazine Hydrochloride

N-(3-fluoro-4-methoxy)benzyl-N'-2-(hydroxy) phenylpiperazine (2.37 g) was added to a solution of 48% hydrobromic acid (35 ml), at ambient temperature. The reaction mixture was heated at 100° C. for 24 hrs, cooled to ambient temperature, diluted with water (200 ml), neutralized with potassium hydroxide solution, and extracted with ethyl acetate. The organic layers were dried over anhydrous sodium sulfate, filtered, and the filtrate was concentrated in vacuo. The residue was flash chromatographed (silica gel), eluting with 1–2% methanol/dichloromethane. The appropriate fractions were collected and concentrated to afford 0.50 g (23%) of product, free base. The free base was dissolved in methanol, cooled to 0° C., and ethereal hydrogen chloride was added. The mixture was concentrated to about 5 ml and triturated with diethyl ether. The precipitate was collected and recrystallized from methanol/diethyl ether to give product, mp 153–155° C.

Analysis: Calculated for $C_{17}H_{20}ClFN_2O_2$: 60.27%; C, 5.95%; H, 8.27%; N, Found: 60.29%; C, 5.73%; H, 8.02%; N.

EXAMPLE 133

N-(2-Chloro-5-[N,N-dimethylcarbamoyloxy]-4-methoxy)benzyl-N'-(pyridin-2-yl)piperazine Cesium carbonate (1.1 g) was added to a solution of N-(2-chloro-5-hydroxy-4-methoxy)benzyl-N'-(pyridin-2-yl) piperazine (0.40 g) and N,N-dimethylcarbainoyl chloride (0.35 ml) in dichloromethane (15 ml), at ambient temperature. The reaction mixture was stirred for 24 hrs, quenched with water, diluted with brine (250 ml) and extracted with dichloromethane. The organic layers were dried over anhydrous sodium sulfate, filtered, and the filtrate was concentrated in vacuo. The reside was flash chromatographed (silica gel), eluting with 25–100% ethyl acetate/heptane. The appropriate fractions were collected and concentrated to afford 0.43 g (88%) of product. Recrystallization from dichloromethane/heptane gave the analytical sample, mp 203–205° C.

Analysis: Calculated for $C_{20}H_{25}ClN_4O_3$: 59.33%; C, 6.22%; H, 13.84%; N, Found: 58.97%; C, 6.16%; H, 13.37%; N.

EXAMPLE 134

N-(2-Chloro-4-[N,N-dimethylcarbamoyloxy]-5-methoxy)benzyl-N'-(2-chloro)phenylpiperazine Hydrochloride Cesium carbonate (0.40 g) was added to a solution of N-(2-chloro-4-hydroxy-5-methoxy)benzyl-N'-(2-chloro) phenylpiperazine (0.35 g) and N,N-dimethylcarbamoyl chloride (0.20 ml) in dichloromethane (15 ml) at ambient temperature. The reaction mixture was stirred for 48 hrs at ambient temperature, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 25–100% ethyl acetate/heptane. The appropriate fractions were collected and concentrated to afford 0.32 g (84%) of product, free base. The free base was dissolved in ethyl acetate, cooled to 0° C., and ethereal hydrogerichloride was added. The precipitate was collected and recrystallized from methanol/ethyl acetate to give product, mp 172–174° C.

Analysis: Calculated for $C_{21}H_{26}Cl_3N_3O_3$: 53.12%; C, 5.52%; H, 8.85%; N, Found: 53.40%; C, 5.21%; H, 8.69%; N.

EXAMPLE 135

N-(2-Chloro-5-[N,N-dimethylcarbamoyloxyl-4-methoxy)benzyl-N'-(2-chloro)phenylpiperazine Cesium carbonate (0.12 g) was added to a solution of N-(2-chloro-5-hydroxy-4-methoxy)benzyl-N'-(2-chloro) phenylpiperazine (0.10 g) and N,N-dimethylcarbamoyl chloride (0.10 ml) in dichloromethane (5 ml), at ambient temperature. The reaction mixture was stirred for 24 hrs at ambient temperature, quenched with water, diluted with brine (250 ml) and extracted with dichloromethane. The organic layers were dried over anhydrous sodium sulfate, filtered, and the filtrate was concentrated in vacuo. Recrystallization of the residue from dichloromethane/heptane gave the 0. 1 5 g (83%) of product, mp 139–1 41° C.

Analysis: Calculated for $C_{21}H_{25}Cl_2N_3O_3$: 57.54%; C, 5.75%; H, 9.59%; N, Found: 57.72%; C, 5.70%; H, 9.26%; N.

EXAMPLE 136

N-(2-Chloro-4-benzyloxy-5-methoxy-N'-(2-methyl) phenylpiperazine Hydrochloride

Sodium hydride (80% dispersion-in-oil, 0.64 g) was added slowly to a suspension of 4-benzyloxy-2-chloro-5-methoxybenzyl chloride (2.0 g) and 2-(methyl)phenylpiperazine (1.5 g) in dichloromethane (50 ml), at ambient temperature. The reaction mixture was stirred for 24 hrs at ambient temperature, quenched with water, diluted with brine (25 ml) and extracted with dichloromethane. The organic layers were dried over anhydrous sodium sulfate, filtered, and the filtrate was concentrated in vacuo. The residue was flash chromatographed (silica gel), eluting with 10–30% ethyl acetate/heptane. The appropriate fractions were collected and concentrated to afford 1.9 g (63%) of product. Recrystallization from dichloromethane/heptane gave the analytical sample, mp 91–93° C.

Analysis: Calculated for $C_{26}H_{29}ClN_2O_2$: 71.46%; C, 6.69%; H, 6.41%; N, Found: 71.26%; C, 6.65%; H, 6.07%; N.

EXAMPLE 137

N-(2-Chloro-4-IN,N-dimethylcarbamoyloxy]-5-methoxy)benzyl-N'-(2-methoxy)phenylpiperazine Hydrochloride Hydrate Cesium carbonate (0.35 g) was added to a solution of N-(2-chloro-4-hydroxy-5-methoxy)benzyl-N'-(2-methoxyphenyl)piperazine (0.30 g) and N,N-dimethylcarbamoyl chloride (0.30 ml) in dichloromethane (3×250 ml), at ambient temperature. The reaction mixture was stirred for 48 hrs at ambient temperature, quenched with water, diluted with brine (250 ml), and extracted with dichloromethane. The organic layers were dried over anhydrous sodium sulfate, filtered, and the filtrate was concentrated in vacuo. The residue was flash chromatographed (silica gel), eluting with 25–100% ethyl acetate/heptane. The appropriate fractions were collected and concentrated to give 0.31 g (86%) of product, free base. The free base was dissolved in ethyl acetate, cooled to 0° C., ethereal hydrogen chloride was added, and the solution was diluted with diethyl ether. The precipitate was collected. Recrystallization from methanol/diethyl ether gave the analytical sample, mp 189–191° C.

Analysis: Calculated for $C_{22}H_{29}Cl_2N_3O_4$: 56.17%; C, 6.21%; H, 8.93%; N, Found: 55.85%; C, 5.81%; H, 8.54%; N.

EXAMPLE 138

1-[[3-Methoxy-4-(methylaminocarbonyloxy)phenyl]methyl]-4-(4-acetylphenyl)piperazine To a solution of 3-methoxy-4-(methylaminocarbonyloxy)benzaldehyde (1.0 g) in 1,2-dichloroethane (20 ml) was added 4'-piperazinoacetophenone (0.98 g), followed by sodium triacetoxyborohydride (1.53 g), with stirring. The reaction mixture was stirred overnight at ambient temperature, poured into saturated sodium carbonate solution (75 ml) and extracted with dichloromethane. The combined organic layers were washed with water and brine, dried over anhydrous sodium sulfate, filtered, and the filtrate was concentrated. The residue was dissolved in dichloromethane and flash chromatographed (silica gel and dichloromethane), eluting with the same solvent system, followed by 1% methanol:dichloromethane. The appropriate fractions were combined and concentrated. The residue was recrystallized from ethyl acetate to give product, mp 120–123° C.

Analysis: Calculated for $C_{21}H_{25}N_3O_4$: 66.48%; C, 6.85%; H, 10.57%; N, Found: 66.24%; C, 6.74%; H, 10.46%; N.

EXAMPLE 139

1-[[3-Methoxy-4-(dimethylaminocarbonyloxy)phenyl]methyl]-4-(2-fluorophenyl)piperazine To a solution of 3-methoxy-4-(dimethylaminocarbonyloxy)benzaldehyde (1.50 g) in 1,2-dichloroethane (14 ml) was added 1-(2-fluorophenyl)piperazine (1.21 g) in 1,2-dichloroethane (13 ml) and sodium triacetoxyborohydride (2.14 g), with stirring. The reaction mixture was stirred for 4 hrs at ambient temperature, poured into saturated sodium carbonate solution (75 ml) and extracted with dichloromethane. The organic layers were combined, washed with water and brine, dried over anhydrous sodium sulfate, filtered, and the filtrate was concentrated. The residue was dissolved in dichloromethane and flash chromatographed (silica gel), eluting with dichloromethane, followed by 0.1, 0.2, 0.4, 0.5, 1, and 2% methanol:dichloromethane. The appropriate fractions were combined and concentrated to afford 2.03 g (78%) of product. Recrystallization from ethyl acetate gave the analytical sample, mp 130–133° C.

Analysis: Calculated for $C_{21}H_{26}FN_3O_3$: 65.1 0%; C, 6.76%; H, 10.85%; N, Found: 65.02%; C, 6.64%; H, 10.79%; N.

EXAMPLE 140

1-[[3-Methoxy-4-[(1,2,3,4-tetrahydroisoquinoline-2-yl)carbonyloxy]phenyl]methyl]-4-(2-fluorophenyl)-piperazine Hydrochloride To a solution of [3-methoxy-4-(1,2,3,4-tetrahydroisoquinoline-2-yl)carbonyloxy]-benzaldehyde (0.52 g) in 1,2-dichloroethane (6.6 ml) was added 1-(2-fluorophenyl)piperazine (0.30 g) followed by sodium triacetoxyborohydride (0.53 g), with stirring. The reaction mixture was stirred for 5 hrs at ambient temperature, poured into saturated sodium carbonate solution (75 ml) and extracted with dichloromethane. The combined organic layers were washed with water and brine, dried over anhydrous sodium sulfate, filtered, and the filtrate was concentrated. The residue was dissolved in dichloromethane and flash chromatographed (silica gel), eluting with dichloromethane, followed by 0.2%, 0.5% and 0.8% methanol:dichloromethane. The appropriate fractions were collected and concentrated to give 0.68 g (87%) of product, free base. The free base was dissolved in diethyl ether, and ethereal hydrogen chloride was added. The precipitate was collected to give product, mp 200–207° C.

Analysis: Calculated for $C_{28}H_{31}ClFN_3O_3$: 65.68%; C, 6.10%; H, 8.21%; N, Found: 65.45%; C, 6.11%; H, 8.11%; N.

EXAMPLE 141

1-[[3-Methoxy-4-(methylaminocarbonyloxy)phenyl]methyl]-4-(2-nitrophenyl)piperazine Hydrochloride To a solution of 3-methoxy-4-(methylaminocarbonyloxy)benzaldehyde (0.60 g) in 1,2-dichloroethane (6 ml) was added 1-(2-nitrophenyl)piperazine(0.60 g) in 1,2-dichloroethane (5.5 ml), followed by sodium triacetoxyborohydride (0.92 g), with stirring. The reaction mixture was stirred for 6 hrs at ambient temperature, poured into saturated sodium carbonate solution (75 ml) and extracted with dichloromethane. The combined organic layers were washed with water and brine, dried over anhydrous sodium sulfate, filtered, and the filtrate was concentrated. The residue was dissolved in dichloromethane and flash chromatographed (silica gel), eluting with dichloromethane, followed by 0.2, 0.5, 1.0, 2.0% methanol:dichloromethane. The appropriate fractions were collected and concentrated to give 0.78 g (68%) of product, free base. The free base was dissolved in dichloromethane, diluted with diethyl ether and ethereal hydrogen chloride was added. The precipitate was collected and recrystallized from 2-propanol to give product, mp 214–218° C.

Analysis: Calculated for $C_{20}H_{25}ClN_4O_5$: 54.98%; C, 5.77%; H, 12.82%; N, Found: 54.84%; C, 5.64%; H, 12.67%; N.

EXAMPLE 142

1-[[4-Methoxy-4-(dimethoxycarbonyloxy)phenyl] methyl]-4-(2-nitrophenyl)piperazine Hydrochloride To a solution of 3-methoxy-4-(dimethylaminocarbonyloxy)benzaldehyde (0.60 g) in 1,2-dichloroethane (5 ml) was added 1-(2-nitrophenyl)piperazine (0.56 g) dissolved in 1,2-dichloroethane (6 ml), followed by sodium triacetoxyborohydride (0.85 g), with stinging. The reaction mixture was stirred for 6 hrs at ambient temperature, poured into saturated sodium carbonate solution (75 ml) and extracted with dichloromethane. The combined organic layers were washed with water and brine, dried over anhydrous sodium sulfate, filtered, and the filtrate was concentrated. The residue was dissolved in dichloromethane and flash chromatographed (silica gel), eluting with dichloromethane, followed by 0.2, 0.5, 0.8, 1.0, and 2.0% methanol:dichloromethane. The appropriate fractions were combined and concentrated to give 0.75 g (67%) of product, free base. The free base was dissolved in dichloromethane, diluted with diethyl ether, and ethereal hydrogen chloride was added The precipitate was collected and recrystallized from 2-propanol to give product, mp 185–1 88° C.

Analysis: Calculated for $C_{21}H_{27}ClN_4O_5$: 55.94%; C, 6.04%; H, 12.42%; N, Found: 55.92%; C, 5.85%; H, 12.31%; N.

EXAMPLE 143

N-(2-Chloro-5-hydroxy-4-methoxy)benzyl-N'-(pyridin-2-yl)piperazine Hydrochloride Sodium hydride (80%, 0.90 g) was added to a solution of N-(2-chloro-5-hydroxy-4-methoxy)benzyl chloride (2.0 g) and N-(pyridin-2-yl)piperazine (1 .9 g) in dichloromethane (40 ml), at ambient temperature. The reaction mixture was stirred for 24 hrs at ambient temperature, quenched with water, diluted with brine (250 ml) and extracted with dichloromethane. The organic layers were dried over anhydrous sodium sulfate, filtered, and the filtrate was concentrated in vacuo. The residue was flash chromatographed (silica gel), eluting with 10–35% ethyl acetate/heptane. The appropriate fractions were collected and concentrated to afford 0.85 g (26%) of product, free base. The free base was dissolved in ethyl acetate, cooled to 0° C., acidified with ethereal hydrogen chloride and diluted with diethyl ether. The precipitate was collected. Recrystallization from ethanol/diethyl ether gave product, mp 220–222° C.

Analysis: Calculated for $C_{17}H_{21}Cl_2N_3O_2$: 55.14%; C, 5.72%; H, 11.35%; N, Found: 54.90%; C, 5.71%; H, 10.99%; N.

EXAMPLE 144

N-[4-(N,N-Dimethylcarbamoyloxy)-3-fluoro] benzyl-N'-(2-chlorophenyl)piperazine Hydrochloride Cesium carbonate (1.22 g) was added to a solution of N-(2-chloro-4-hydroxy-5-methoxy)benzyl-N'-(2-chlorophenyl)piperazine (1.00 g) and N,N-dimethylcarbamoyl chloride (0.60 ml) in dichloromethane (15 ml), at ambient temperature. The reaction mixture was stirred for 48 hrs at ambient temperature, quenched with water, diluted with brine (250 ml) and extracted with dichloromethane. The organic layers were dried over anhydrous sodium sulfate, filtered, and the filtrate was concentrated in macuo. The residue was flash chromatographed (silica gel), eluting with 25–100% ethyl acetate/heptane. The appropriate fractions were collected and concentrated to afford 0.90 g (74%) of product, free base. The free base was dissolved in ethyl acetate, cooled to 0° C., acidified with ethereal hydrogen chloride and diluted with diethyl ether. The precipitate was collected. Recrystallization from methanol/diethyl ether gave product, mp 235–237° C.

Analysis: Calculated for $C_{20}H_{24}Cl_2FN_3O_2$: 56.08%; C, 5.65%; H, 9.81%; N, Found: 56.04%; C, 5.49%; H, 9.61%; N.

EXAMPLE 145

N-(2-Chloro-5-hydroxy-4-methoxy)benzyl-N'-(2-methoxyphenyl)piperazine

Sodium hydride (80% suspension-in-oil, 0.60 g) was added to a solution of 2-chloro-5-hydroxybenzyl chloride (1.02 g) and 1-(2-methoxyphenyl)piperazine (1.05 g) in dichloromethane (40 ml), at ambient temperature. The reaction mixture was stirred for 48 hrs at ambient temperature, quenched with water, diluted with brine (250 ml) and extracted with dichloromethane. The organic layers were dried over anhydrous sodium sulfate, filtered, and the filtrate was concentrated in vacuo. The residue was flash chromatographed (silica gel), eluting with 20–40% ethyl acetate/heptane. The appropriate fractions were collected and concentrated to afford 0.59 (33%) of product. Recrystallization from dichloromethane/petroleum ether gave the analytical sample, mp 72–75° C.

Analysis: Calculated for $C_{19}H_{23}ClN_2O_3$: 62.89%; C, 6.39%; H, 7.72%; N, Found: 62.89%; C, 6.36%; H, 7.36%; N.

We claim:
1. A compound of the formula

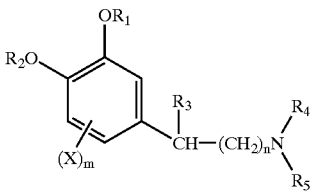

wherein:

$R_1$ is a group of the formula $CH_2C{\equiv}C{-}R_9$;

$R_2$ is hydrogen, loweralkyl, a group of the formula $CONR_6R_7$, a group of the formula $SO_2R_{10}$, a group of the formula

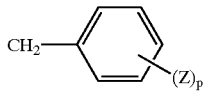

or a group of the formula $Si(R_{11})_3$;

$R_3$ is hydrogen or loweralkyl;

$R_4$ and $R_5$ taken together with the nitrogen atom to which they are attached form a group of the formula

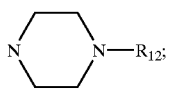

$R_6$ is hydrogen or loweralkyl;

$R_7$ is alkyl of 1 and 10 carbon atoms hydrogen or loweralkyl, a group of the formula

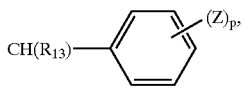

a group of the formula

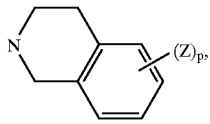

or a group of the formula

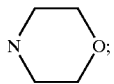

or $R_6$ and $R_7$ taken together with the nitrogen atom to which they are attached form a group of the formula

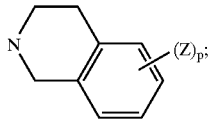

$R_9$ is hydrogen, a group of the formula $C(R_{14}R_{14'})OH$, a group of the formula

or a group of the formula

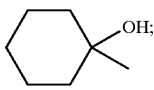

$R_{10}$ is loweralkyl;

$R_{11}$ is loweralkyl;

$R_{12}$ is loweralkyl, hydroxyloweralkyl, a group of the formula $COR_{15}$, a group of the formula

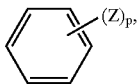

a group of the formula

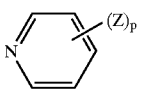

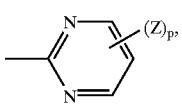

a group of the formula

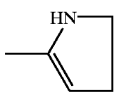

or a group of the formula

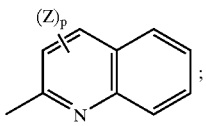

$R_{13}$ is hydrogen or loweralkyl;

$R_{14}$ is hydrogen or loweralkyl;

$R_{14}$ is hydrogen or loweralkyl;

$R_{15}$ is a group of the formula

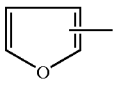

or loweralkyl;

$R_{20}$ is loweralkyl;

X is hydrogen or halogen;

Z is hydrogen, halogen, loweralkyl, hydroxyl, loweralkoxy, trifluoromethyl, nitro or cyano; $R_{20}$ CO, or a group of the formula $OCONR_6R_7$;

m is 1 or 2;

n is 0 or 1;

p is 1 or 2;

the optical isomers thereof; or the pharmaceutically acceptable salts thereof.

2. A compound according to claim 1 wherein $R_2$ is loweralkyl.

3. A compound according to claim 1 wherein $R_2$ is a group of the formula $CONR_6R_7$.

4. A compound according to claim 3 wherein $R_2$ is a group of the formula $CONR_6R_7$, $R_4$ and $R_5$ taken together with the nitrogen to which they are attached form a group of the formula

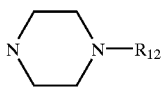

and n is 0.

5. The compound according to claim 1 which is 4-methoxy-3-propargyloxy-1-[(4-methylpiperazin-1-yl)methyl]benzene.

6. The compound according to claim 1 which is 4-[3-[2-methoxy-5-(4-methylpiperazin-1-yl-methyl)phenoxy]prop-1-ynyl]tetrahydrothiopyran-4-ol.

7. The compound according to claim 1 which is 4-methoxy-3-(propargyloxy)-1-[[4-(pyridin-2-yl)piperazin-1-yl]methyl]benzene.

8. The compound according to claim 1 which is 3-[2-methoxy-5-[[4-(pyridin-2-yl)piperazin-1-yl]methyl]phenoxy(prop-1-ynyl)tetrahydrothiopyran-4-ol.

9. A method of relieving memory dysfunction in mammals comprising administering to a mammal requiring memory dysfunction relief, a memory dysfunction relieving effective amount of a compound of claim 1.

10. A memory dysfunction relieving composition comprising an adjuvant and as the active ingredient, a memory dysfunction effective amount of a compound of claim 1.

11. A method of simultaneously treating depression and memory dysfunction in mammals suffering from memory dysfunction and depression comprising administering to a mammal suffering from memory dysfunction and requiring depression treatment, a memory dysfunction relieving and depression treatment effective amount of a compound of claim 1.

12. A simultaneous depression treating and memory dysfunction relieving composition comprising an adjuvant and as the active ingredient, a depression treating and memory dysfunction relieving effective amount of a compound of claim 1.

* * * * *